US006864375B2

(12) United States Patent
Huang et al.

(10) Patent No.: US 6,864,375 B2
(45) Date of Patent: Mar. 8, 2005

(54) HIGHLY STABLE AND EFFICIENT NONLINEAR OPTICAL CHROMOPHORES FOR ELECTRO-OPTIC POLYMERS

(75) Inventors: Diyun Huang, Seattle, WA (US); Tim Londergan, Seattle, WA (US); Galina K. Todorova, Seattle, WA (US); Jingsong Zhu, Mountlake Terrace, WA (US)

(73) Assignee: Lumera Corporation, Bothell, WA (US)

( * ) Notice: Subject to any disclaimer, the term of this patent is extended or adjusted under 35 U.S.C. 154(b) by 98 days.

(21) Appl. No.: 10/439,621

(22) Filed: May 16, 2003

(65) Prior Publication Data

US 2003/0205701 A1 Nov. 6, 2003

(Under 37 CFR 1.47)

Related U.S. Application Data

(63) Continuation of application No. 09/932,831, filed on Aug. 17, 2001.
(60) Provisional application No. 60/226,267, filed on Aug. 17, 2000.

(51) Int. Cl.[7] .................. C07D 333/38; H01C 13/00
(52) U.S. Cl. ........................ 549/61; 252/501.1
(58) Field of Search .................. 549/61; 252/501.1

(56) References Cited

U.S. PATENT DOCUMENTS

| 4,421,761 A | 12/1983 | Nagai et al. ............... 424/275 |
| 5,080,991 A | 1/1992 | Ono et al. ..................... 430/73 |
| 5,290,630 A | 3/1994 | Devonald et al. .......... 428/333 |
| 5,670,091 A | 9/1997 | Marder ....................... 252/582 |
| 5,679,763 A | 10/1997 | Jen ............................. 528/403 |
| 5,696,243 A | 12/1997 | Beckmann et al. ......... 534/753 |
| 5,783,649 A | 7/1998 | Beckmann et al. ......... 526/256 |
| 5,834,575 A | 11/1998 | Honda et al. ............... 526/256 |
| 5,859,251 A | 1/1999 | Reinhardt et al. .......... 546/255 |
| 6,051,722 A | 4/2000 | Honda et al. ............... 549/407 |
| 6,067,186 A | 5/2000 | Dalton et al. ............... 359/321 |
| 6,090,332 A | 7/2000 | Marder ....................... 264/435 |
| 6,130,339 A | 10/2000 | Tan et al. ..................... 549/50 |
| 6,197,921 B1 * | 3/2001 | Tan et al. .................... 528/380 |
| 6,197,922 B1 | 3/2001 | Möhwald et al. ........... 528/403 |
| 6,348,992 B1 | 2/2002 | Zhang et al. ............... 359/321 |
| 6,361,717 B1 | 3/2002 | Dalton et al. ............... 252/582 |
| 6,376,655 B1 | 4/2002 | Berg et al. .................. 534/573 |
| 6,393,190 B1 | 5/2002 | He et al. ..................... 385/130 |
| 6,403,809 B1 * | 6/2002 | Holmes et al. ............... 549/41 |
| 6,514,434 B1 | 2/2003 | He et al. ..................... 252/582 |

FOREIGN PATENT DOCUMENTS

| CA | 1110385 | 10/1981 |
| DE | 44 01 911 A1 | 8/1995 |
| DE | 44 16 476 A1 | 11/1995 |
| DE | 195 32 828 A1 | 3/1996 |
| EP | 32748 B1 | 8/1984 |
| EP | 0 414 185 A2 | 2/1991 |
| EP | 0 637 774 A1 | 2/1995 |
| EP | 0 729 056 A1 | 8/1996 |
| EP | 0 754 709 A1 | 1/1997 |
| JP | 61-65881 A | 4/1986 |
| JP | 2-244059 A | 9/1990 |
| JP | 3-31850 A | 2/1991 |
| JP | 08-108624 | 4/1996 |
| JP | 2000-089268 | 3/2000 |
| JP | 2000-280621 A | 10/2000 |
| JP | 2001-085713 | 3/2001 |
| JP | 2001-167885 A | 6/2001 |
| WO | WO 01/53746 | 7/2001 |
| WO | WO 01/96409 | 12/2001 |

OTHER PUBLICATIONS

Abstract of DE 195 32 828 A1, esp@cenet database, Mar. 21, 1996.
Abstract of DE 44 01 911 A1, esp@cenet database, Aug. 3, 1995.
Abstract of DE 44 16 476 A1, esp@cenet database, Nov. 16, 1995.
Abstract of EP 0 754 709 A1, esp@cenet database, Jan. 22, 1997.
Abstract of JP 08–108624, Patent Abstracts of Japan, Apr. 30, 1996.
Abstract of JP 2000–089268, Patent Abstracts of Japan, Mar. 31, 2000.
Abstract of JP 2001–085713, Patent Abstracts of Japan, Mar. 30, 2001.
Akoudad, S. et al., "Low Oxidation Potential Tetrathiafulvalene Analogues Based on 3,4–Dialkoxtthiophene π–Conjugating Spacers," *Journal of Organic Chemistry* 64: 4267–4272, 1999.
Cai, C. et al., "Donor—Acceptor–Substituted Phenylethenyl Bithiophenes: Highly Efficient and Stable Nonlinear Optical Chromophores," *Organic Letters* l(11): 1847–1849, 1999.
Chemical Abstracts Registry Database (American Chemical Society), Registry No. 501910–13–0, Apr. 2003.
Chemical Abstracts Registry Database search results regarding Registry No. 501910–13–0 database entry date, Search performed on May 19, 2003.

(List continued on next page.)

*Primary Examiner*—Deborah C Lambkin
(74) *Attorney, Agent, or Firm*—Seed IP Law Group PLLC

(57) ABSTRACT

In various embodiments, chromophores are described that include novel electron acceptors, novel electron donors, and/or novel conjugated bridges that are useful in nonlinear optical applications. In some embodiments, the present invention provides chromophore architectures wherein a chromophore contains more than one electron acceptor in electronic communication with a single electron donor, and/or more than one electron donor in electronic communication with a single electron acceptor. Also described is processes for providing materials comprising the novel chromophores and polymer matrices containing the novel chromophores. Electro-optic devices described herein contain one or more of the described electron acceptors, electron donors, conjugated bridges, or chromophores.

6 Claims, 35 Drawing Sheets

OTHER PUBLICATIONS

Chemical Catalogs Database (American Chemical Society), Accession No. 2003:2301932, Apr. 2003.

Dalton et al., "From Molecules to Opto–chips: Organic Electro–optic Materials," *J. of Materials Chemistry* 9:1905–1920, 1999.

Dalton, "Polymeric Electro–optic Materials: Optimization of Electro–optic Activity, Minimization of Optical Loss, and Fine Tuning of Device Performance," *Opt. Eng.* 39(3):589–595, Mar. 2000.

Dini and Aszodi, "Synthesis of a Dihydroxythiophene Analogue of Catechosporines," *Bioorganic & Medicinal Chemistry Letters 10*: 349–352, 2000.

Fleitz and Sutherland, "Investigating the nonlinear optical properties of molten organic materials," *Proceedings of SPIE*, vol. 3146, pp. 24–30, 1997.

Halfpenny, J. et al., "Optimisation of substitution at the 2– and 5– positions of 3,4–dialkoxythiophenes via the Mannich reaction: the influences of steric crowding, electrophile reactivity and temperature," *Journal of the Chemical Society, Perkin Transactions I*: 2595–2603, 2001.

Jen, A. et al., "Synthesis and Characterization of Highly Efficient and Thermally Stable Diphenylamino–Substituted Thiophene Stilbene Chromophores for Nonlinear Optical Applications," *Advanced Materials 9*(2): 132–135, 1997.

Jen, A.K.Y. et al., "Synthesis and Characterization of Highly Efficient, Chemically and Thermally Stable Chromophores with Chromone–Containing Electron Acceptors for NLO Applications," *Advanced Materials 11*(6): 452–455, 1999.

Jousselme, B. et al., "Enhancement of the π–electron delocalization and fluorescene efficiency of 1,6–diphenyl–1,3,5–hexatriene by covalent rigidification," *Tetrahedron Letters 41*: 5057–5061, 2000.

Kane and Gao, "Synthesis of a Series of Conjugated Enyne Polythiophenes," *Polymer Preprints 33*(1): 1064–1065, Apr. 1992.

Kane and Gao, "Synthesis of a Series of Conjugated Enyne Polythiophenes, II," *Polymer Preprints 33*(2): 192–193, Aug. 1992.

Kato, S. et al., "N–Substituted chloroacetanilides," *Chemical Abstracts*, Accession No. 1986:460516, 1986. See also JP 61–65881.

Kim et al., "Nonlinear Optical Chromophores Containing Dithienothiophene as a New Type of Electron Relay," *J. of Materials Chemistry* 9:2227–2232, 1999.

Kojima et al., "Facile Sunthesis of Thiophene Derivatives Using a Cyclopropenyl Cation," *Synthesis 10*:1193–1195, Oct. 1996.

Lee et al., "Optical Intensity Modulator Based on a Novel Electrooptic Polymer Incorporating a High $\mu\beta$ Chromophore," *IEEE J. of Quantum Electronics 36*(5): 527–532, May 2000.

Mavlankar & Rangnekar, "Synthesis of 2–(aryl/hetaryl)azo–3,4–dihydroxy–5–(4–nitrophenyl)–thiophene–1,1–dioxone derivatives and their dyeing properties," *Indian Journal of Fibre & Textile Research 16*: 282–284, Dec. 1991.

Miyaji, T. et al., "Electrophotographic photoreceptor using a charge–transporting compound as a charge–generating substance," *Chemical Abstracts*, Accession No. 1991:546598, 1991. See also JP 03–31850.

Miyazaki, H. et al., "Electrophotographic photoreceptor using new photoconductive material," *Chemical Abstracts*, Accession No. 1991:237611, 1991. See also JP 02–244059.

Nakamura, K. et al., "Organic electroluminescent device," *Chemical Abstract*, Accession No. 2001:451353, 2001. See also JP 2001–167885.

Nelson and Boyd, "Enhanced electro–optic response of layered composite materials," *Applied Physics Letters 74*(17): 2417–2419, Apr. 26, 1999.

Ng, S.C. et al., "The Synthesis and Characterisation of Fluorescent Poly(heteroaromatic oxadiazole)s," *Macromolecular Chemistry and Physics 202*(1): 8–13, 2001.

Ogiso, A. et al., "Rewritable optical recording medium including polyheterocyclic dye for high–density laser recording," *Chemical Abstracts*, Accession No. 2000:715405, 2000. See also JP 2000–280621.

Ono, N. et al., "Syntheiss of Oligo(thienylenevinylenes) Substituted with Alkoxy Groups," *Heteroatom Chemistry 12*(5): 414–417, 2001.

Raimundo et al., "Push–pull Chromophores Based on 2,2?–bi(3,4–ethylenedioxythiophene) (BEDOT) p–conjugating Spacer," *Tetrahedron Letters 42*:1507–1510, 2001.

Raimundo, J–M. et al. "Proquinoid acceptors as building blocks for the design of efficient π–conjugated fluorophores with high electron affinity," *Chemical Communications*, pp. 939–940, 2000.

Raimundo, J–M. et al., "Design and Synthesis of Push–Pull Chromophores for Second–Order Nonlinear Optics Derived from Rigidified Thiophene–Based π–Conjugating Spacers," *Journal of Organic Chemistry 67*:205–218, 2002.

Raimundo, J–M. et al., "Huge enhancement of the quadratic nonlinear optical susceptibility in push–pull chromophores based on bridged dithienylethylene spacers," *Chemical Communications*, pp. 1597–1598, 2000.

Rangnekar and Mavlankar, "Synthesis of 5–(4–arylazo/hetarylazo–phenyl)–2–hetaryl–3,4–dihydroxy–thiophene derivatives and their application on polyester fibres as disperse dyes," *Indian Journal of Fibre & Textile Research 17*: 153–157, Sep. 1992.

Rangnekar and Mavlankar, "Synthesis of Novel c–Hetero–fused Thiophene Derivatives," *Journal of Heterocyclic Chemistry 28*(5): 1449–1451, Aug.–Sep., 1991.

Reinhardt, "Highly Active Two–Photon Dyes: Design, Synthesis, and Characterization toward Application," *Chem. Mater. 10*(7):1863–1874, 1998.

Reinhardt, B.A. et al., "Optical Power Limiting in Solution Via Two–Photon Absorption: New Aromatic Heterocyclic Dyes with Greatly Improved Performance," *Proceedings of SPIE*, vol. 3146, pp. 2–11, 1997.

Roncali, J., "Synthetic Principles for Bandgap Control in Linear π–Conjugated Systems," *Chem. Rev. 97*: 173–205, 1997.

Shi et al., "Low (Sub–1–Volt) Halfwave Voltage Polymeric Electro–optic Modulators Achieved by Controlling Chromophore Shape," *Science 288*:119–122, Apr. 7, 2000.

Shu, Y–C et al., "Synthesis and Characterization of Nonlinear Optical Chromophores with Conformationally Locked Polyenes Possessing Enhanced Thermal Stability," *Chemistry of Materials 11*(6): 1628–1632, Jun. 1999.

Turbiez, M. et al., "Mixed π–conjugated oligomers of thiophene and 3,4–ethylenedioxythiophene (EDOT)," *Tetrahedron Letters 41*: 5521–5525, 2000.

Unrow and Reinhardt, "Synthesis of substituted thiophene–benobisthiazoole oligomers for molecular weight—third order NLO property correlations," *Proceeding of SPIE*, vol. 1626, pp. 450459, 1992.

Wolff, J.J., "Organic Materials for Second–Order Non–Linear Optics," *Advances in Physical Organic Chemistry 32*: 121–217, 1999.

Wu, X. et al., "Highly efficient, thermally and chemically stable nonlinear optical chromophores based on the α–perfluoroaryldicyanovinyl electron acceptors," *Chemical Communications*, pp. 2391–2392, 1999.

Das et al., *Chemical Abstracts*, CA 132:42429, 1999.

Kaneko et al., *Chemical Abstracts*, CA 131:20257, 1999.

Nishimoto et al., *Chemical Abstracts*, CA 126:218690, 1997.

Kafuku et al., *Chemical Abstracts*, CA 122:108888, 1995.

Chiba et al., *Chemical Abstracts*, CA 122:58182, 1995.

Hagiwara et al., *Chemical Abstracts*, CA 118:201736, 1993.

* cited by examiner

HIGHLY STABLE AND EFFICIENT NONLINEAR OPTICAL CHROMOPHORES FOR ELECTRO-OPTIC POLYMERS

CROSS-REFERENCE TO RELATED APPLICATIONS

This application is a continuation of U.S. application Ser. No. 09/932,821, filed Aug. 17, 2001 (now pending); which application claims the benefit of U.S. Provisional Patent Application No. 60/226,267, filed Aug. 17, 2000, which is incorporated herein by reference in its entirety.

BACKGROUND OF THE INVENTION

1. Technical Field

The field of invention is design, synthesis, use, and devices based on advanced nonlinear optical (NLO) materials.

2. Description of the Related Art

All patents, patent applications, and publications cited within this application are incorporated herein by reference to the same extent as if each individual patent, patent application or publication was specifically and individually incorporated by reference.

The development of chromophores demonstrating non-linear optical (NLO) properties and the uses thereof, including waveguides incorporating the chromophores and the preparation thereof, and the development of organic polymeric matrices to contain the chromophores, and optical devices incorporating the chromophores/waveguides as well as methods of preparing same, are active areas of research. Disclosures related to these areas have appeared in numerous Patents including the following recently issued U.S. Pat. Nos.: 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,408,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514,799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091; 5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,966,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,322; and 6,091,879. The entire disclosure of these patents is hereby incorporated herein by reference for all purposes.

Despite the attention given to this area, there is a pressing need for improved chromophores that can be used in electro-optic applications and related uses. The present invention is directed to fulfilling this need and providing uses, devices, and communication systems based on non-linear optically active chromophores.

SUMMARY OF THE INVENTION

In various aspects, chromophores comprise of novel electron acceptors (A), novel electron donors (D), and/or novel conjugated bridges (p). The chromophores have non-linear optical properties, i.e., are NLO chromophores.

In one aspect, a thiophene-containing chromophore has the structure

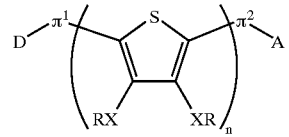

wherein, independently at each occurrence, D is an electron donating group having low electron affinity relative to the electron affinity of A; $\pi^1$ is absent or a bridge that provides electronic conjugation between D and the thiophene ring; $\pi^2$ is absent or a bridge that provides electronic conjugation between A and the thiophene ring; A is an electron accepting group having high electron affinity relative to the electron affinity of D; X is O or S; R is alkyl, aryl, heteroalkyl or heteroaryl; and n is 1, 2, 3 or 4.

Specific D groups that may be incorporated into a chromophore include, without limitation, D groups of the following structures,

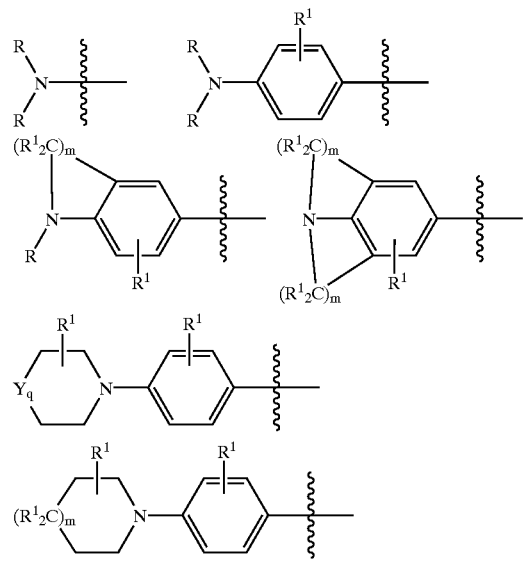

-continued

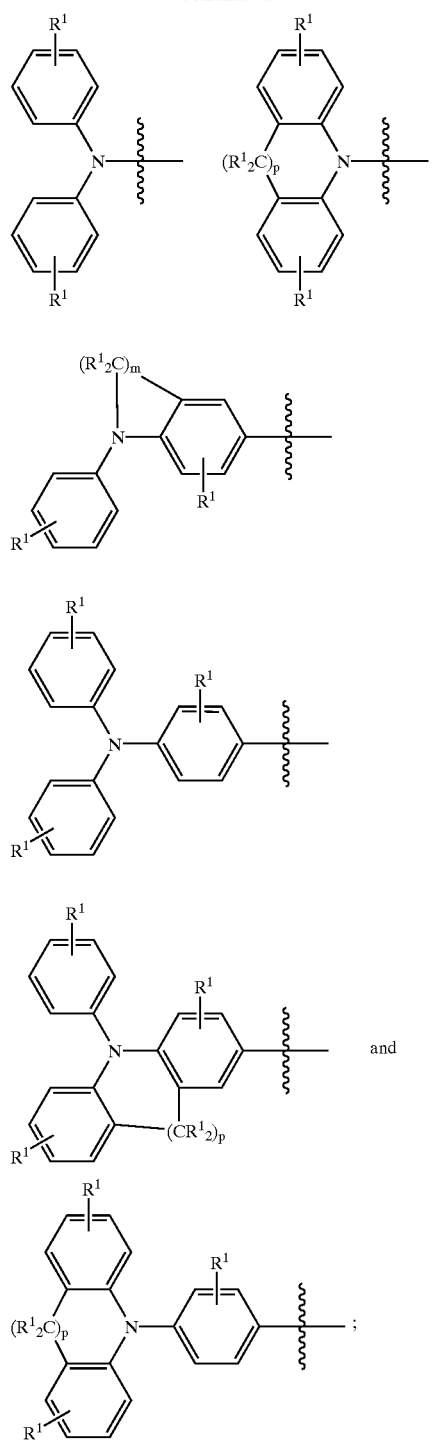

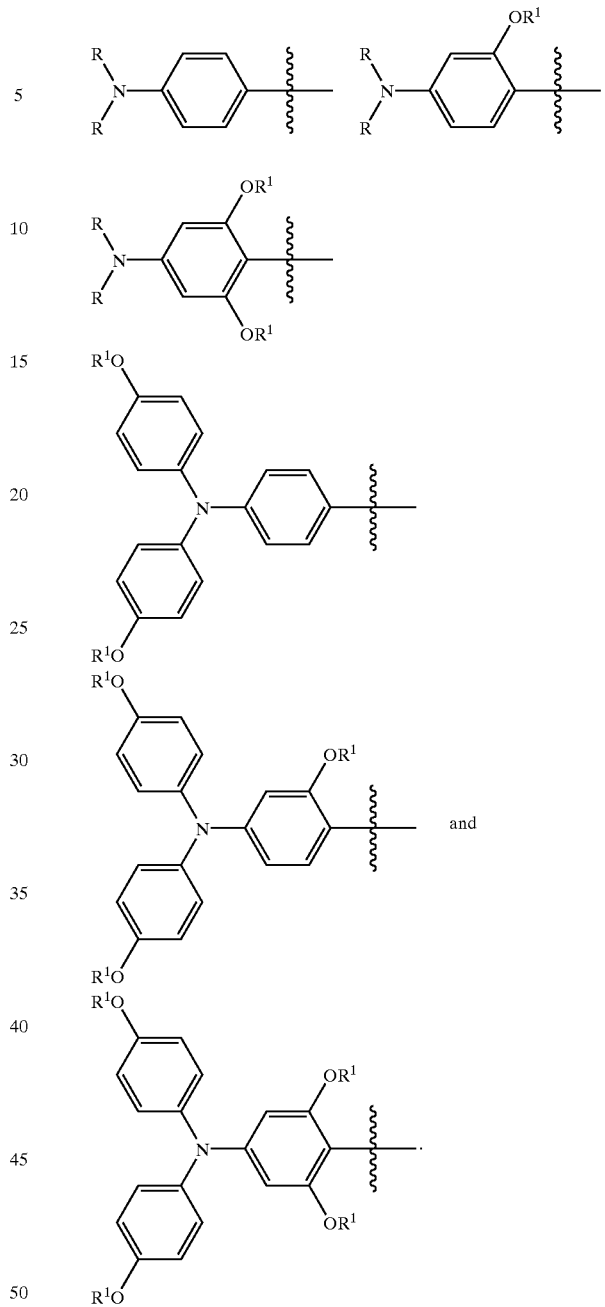

wherein, independently at each occurrence, R is alkyl, aryl or heteroalkyl; $R^1$ is hydrogen, alkyl, aryl or heteroalkyl; Y is O, S or Se; m is 2, 3 or 4; p is 0, 1 or 2; and q is 0 or 1. In one embodiment, R contains 1–12 carbons; $R^1$ is hydrogen or contains 1–12 carbons; Y is O or S; m is 2, 3 or 4; p is 0, 1 or 2; and q is 0 or 1. Some preferred D groups that may be present in a chromophore according to the present invention are of the structures:

In one aspect of the invention, the chromophore contains both $\pi^1$ and $\pi^2$ groups, i.e., the $\pi^1$ and $\pi^2$ groups are not absent from the chromophore. One or both of $\pi^1$ and $\pi^2$ may be, independently at each occurrence, of the structure

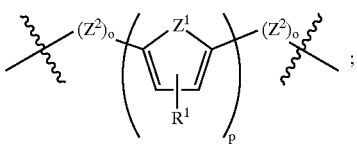

wherein, independently at each occurrence, $Z^1$ is O, S, Se, $NR^1$, $C(R^1)_2$ or —$C(R^1)$=$C(R^1)$—; p is 0, 1 or 2; o is 0, 1 or 2; o+p is at least 1; $R^1$ is hydrogen, alkyl, aryl or heteroalkyl;

$Z^2$ is

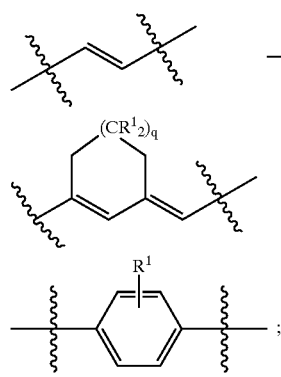

and q is 0 or 1.

Some specific structures for $\pi^1$ and $\pi^2$ are:

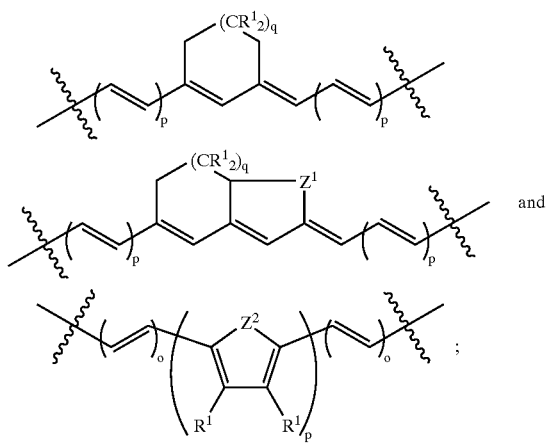

wherein, independently at each occurrence, $R^1$ is hydrogen, alkyl, aryl or heteroalkyl; $Z^1$ is O, S, Se, $NR^1$, $C(R^1)_2$ or —$C(R^1)=C(R^1)$—; p is 0, 1 or 2; o is 0, 1 or 2; o+p is at least 1; and q is 0 or 1. In one aspect each of $\pi^1$ and $\pi^2$ are —CH=CH—.

Some specific A groups that may be incorporated into chromophores according to the present invention are:

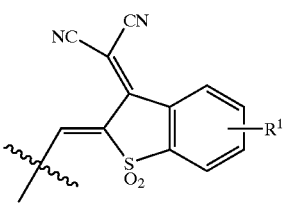

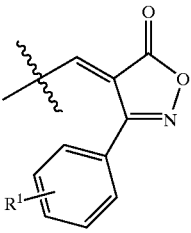
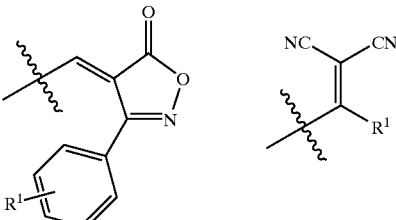

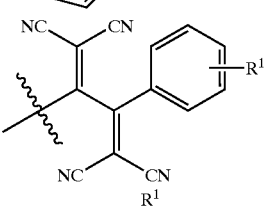

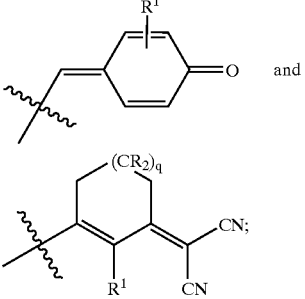

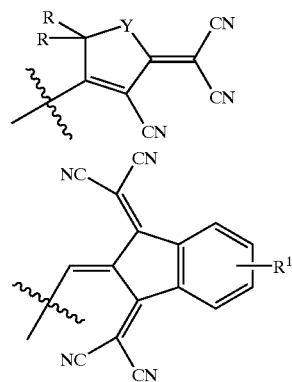

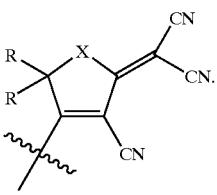

wherein, independently at each occurrence, R is alkyl, aryl or heteroalkyl; $R^1$ is hydrogen, alkyl, aryl or heteroalkyl; Y is O, S or Se; and q is 0 or 1. Optionally, R contains 1–12 carbons; $R^1$ is hydrogen or contains 1–12 carbons; Y is O or S; and q is 0 or 1. A specifically preferred A group is of the formula

In various aspects of the invention, R is alkyl, and/or aryl, and/or heteroalkyl, and/or heteroaryl, including each and every combination thereof. Optionally, R is hydrophobic, while alternatively R is hydrophilic. Optionally, an R group is saturated, while alternatively an R group is unsaturated. The R group may have, in various aspects of the invention, 1–6 carbons, or 7–12 carbons, or 13–22 carbons.

The value of n may be 1, or 2, or 3, or 4, or each and every combination thereof, e.g., 2 or 3. In one aspect, X is O, while in another aspect X is S.

In one chromophore according to the present invention, $\pi^1$ and $\pi^2$ are

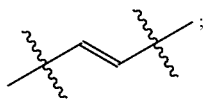
and A is
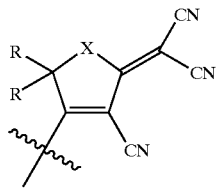
wherein R is independently at each occurrence alkyl, aryl or heteroalkyl.
Thus, in one aspect, a thiophene-containing chromophore has of the structure
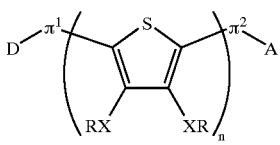
wherein, independently at each occurrence, D is selected from the group consisting of
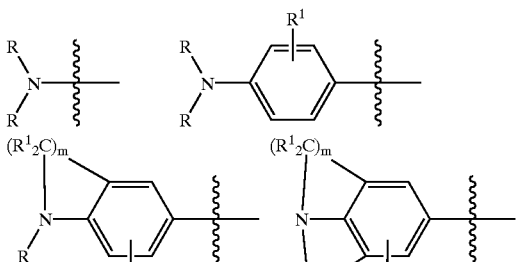
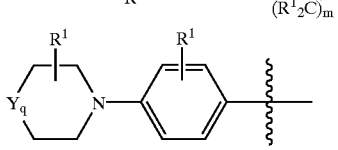
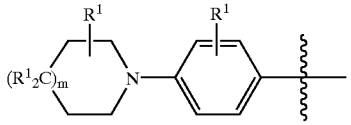
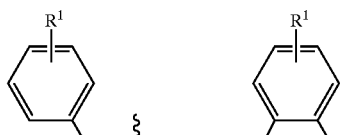
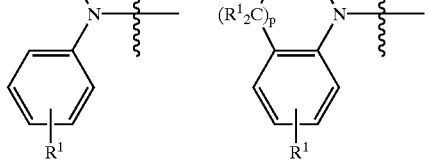
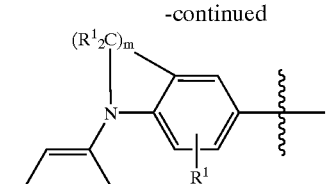
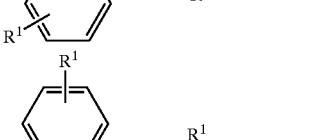
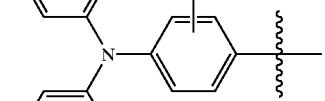
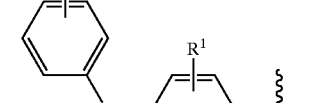
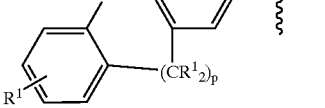
and
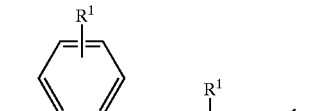
$\pi^1$ and $\pi^2$ are independently
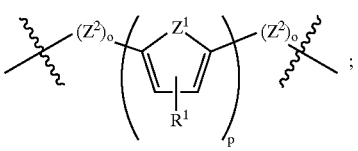
A is selected from the group consisting of
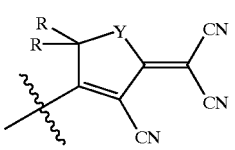
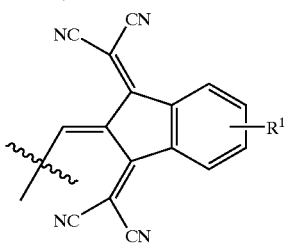

-continued

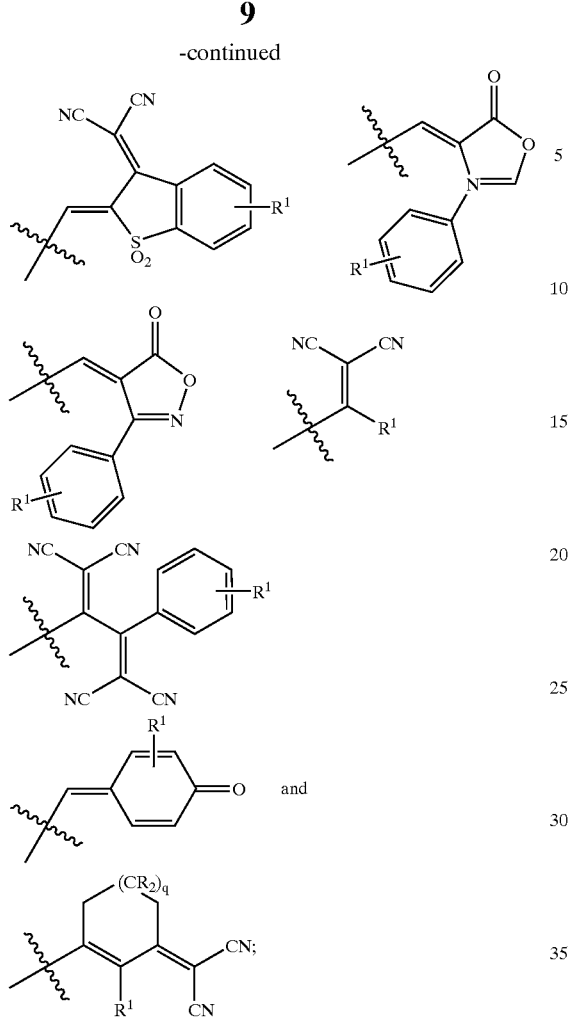

X is O or S; R is alkyl, aryl or heteroalkyl; n is 1, 2, 3 or 4; $R^1$ is hydrogen, alkyl, aryl or heteroalkyl; Y is O, S or Se; $Z^1$ is O, S, Se, $NR^1$, $C(R^1)_2$ or $—C(R^1)=C(R^1)—$;

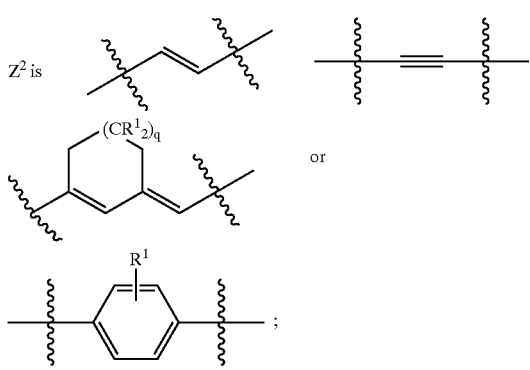

q is 0 or 1; p is 0, 1 or 2; o is 0, 1 or 2; o+p is at least 1; and m is 2, 3 or 4.

In another chromophore according to the present invention, D is selected from:

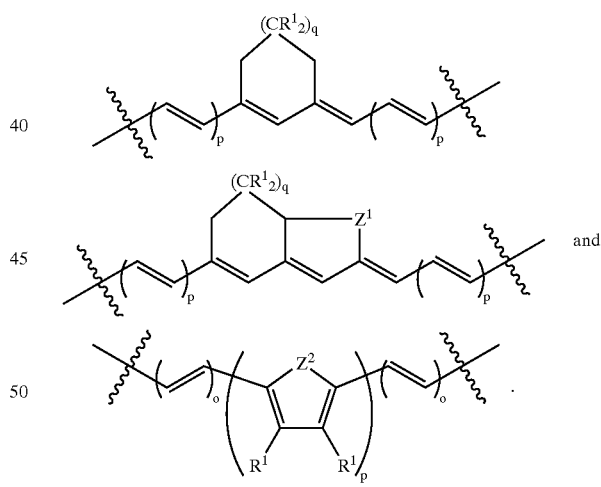

and π is selected from:

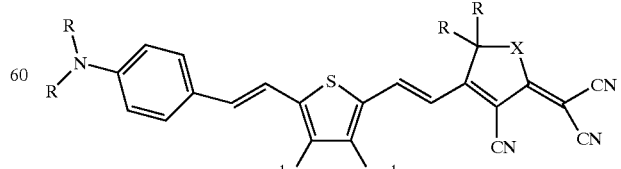

In another aspect, a chromophore has the structure wherein, independently at each occurrence, R is alkyl, aryl or heteroalkyl; $R^1$ is alkyl, aryl or heteroalkyl; and X is O or S. For example, R may be —(CH$_2$)$_w$OH, —(CH$_2$)$_w$OR$^1$, —(CH$_2$)$_w$SH, —(CH$_2$)$_w$CO$_2$Et, —(CH$_2$)$_w$CO$_2$H, —(CH$_2$)$_w$NH$_2$, —(CH$_2$)$_w$CN, —(CH$_2$)$_w$halogen, or —COC$_6$H$_4$OCF=CF$_2$ where w is an integer selected from 1–12; and R$^1$ may be hydrogen, R, perfluoroalkyl, SiR$_3$, Si(CH$_3$)$_2$t-Bu, or Si(i-Pr)$_3$.

In another aspect, a chromophore has the structure

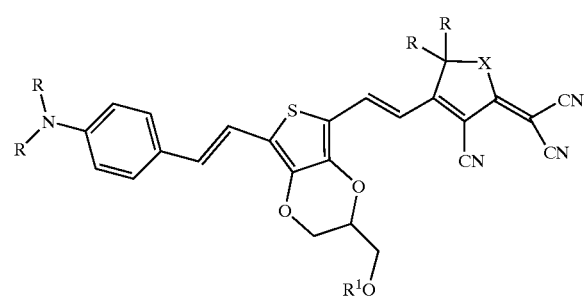

wherein, independently at each occurrence, R is alkyl, aryl or heteroalkyl; R$^1$ is alkyl, aryl or heteroalkyl; and X is O or S. For example, R may be —(CH$_2$)$_w$OH, —(CH$_2$)$_w$OR$^1$, —(CH$_2$)$_w$SH, —(CH$_2$)$_w$CO$_2$Et, —(CH$_2$)$_w$CO$_2$H, —(CH$_2$)$_w$NH$_2$, —(CH$_2$)$_w$CN, —(CH$_2$)$_w$halogen, or —COC$_6$H$_4$OCF=CF$_2$ where w is an integer selected from 1–12; and R$^1$ may be hydrogen, R, perfluoroalkyl, SiR$_3$, Si(CH$_3$)$_2$t-Bu, or Si(i-Pr)$_3$.

In another aspect, a chromophore has a structure

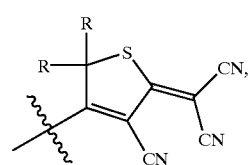

wherein, independently at each occurrence, D is an electron donating group having low electron affinity relative to the electron affinity of π is absent or a bridge that provides electronic conjugation between D and the double bond adjacent to π; and R is alkyl, aryl, heteroalkyl or heteroaryl.

In another aspect, a chromophore has the structure wherein R is alkyl, aryl, or heteroalkyl and R$^1$ is hydrogen, alkyl, aryl or heteroalkyl.

In another aspect, a chromophore has the structure

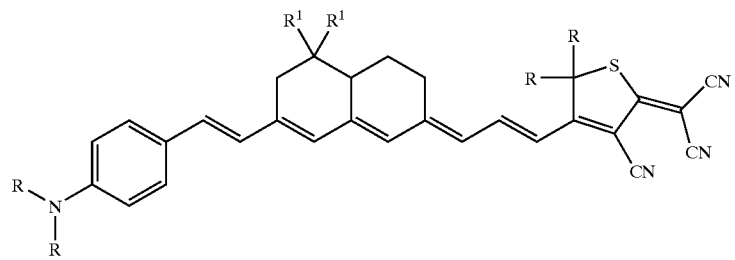

wherein R is alkyl, aryl, or heteroalkyl and R$^1$ is hydrogen, alkyl, aryl or heteroalkyl.

In another aspect, a chromophore is made by any of the processes illustrated in any of the FIGS. 4A, 4B, 5A, 6A, 7C, 8A, 9A, 10A, 11A, 12A, 13A, 14A, 15A, 16A, 17, 19, 20, 21, 22, 23, 24, and 25.

In another aspect according to the present invention, chromophores or components thereof are provided as shown in any of the FIGS. 1A, 1B, 2A, 2B, 3A, 3B, 4A, 4B, 4C, 5A, 5B, 6A, 6B, 7A, 7B, 7C, 8A, 8B, 9A, 9B, 10A, 10B, 11A, 11B, 12A, 12B, 13A, 13B, 14A, 14B, 15A, 15B, 16A, 16B, 17, 19, 20, 21, 22, 23, 24, and 25.

In another aspect, a composition of matter comprises

E—L$_n$ wherein E is a chromophore according to the present invention as set forth herein; L comprises a chemically reactive group that is crosslinkable; and n=1–24. For example, L may represent a thermally crosslinkable trifluorovinylether group. In a composition of matter including E—L$_n$, in one aspect, at least one of D, π, or A of the chromophore is covalently bound to a polymer. Optionally, D, π, or A is further substituted with halogen, alkyl, aryl, or heteroalkyl. The chromophore may be non-covalently incorporated into a crosslinkable polymer matrix, or the chromophore may be covalently incorporated into a crosslinked polymer matrix.

According to the present invention a process can comprise sequentially 1) incorporating a chromophore according to the present invention as described herein, into a polymer matrix; 2) maintaining the polymer matrix at a selected temperature to allow effective chromophore mobility; and 3) applying an electric field sufficient to induce an effective amount of dipole alignment of the chromophore in the polymer matrix. A further optional step includes heating the composition to a selected temperature sufficient to affect crosslinking. Embodiments of the present invention also provide compositions of matter prepared by these processes.

The chromophores according to the present invention may be incorporated into many useful devices e.g., electro-optic devices, waveguides, optical switches, optical modulators, optical couplers, optical router, and generally into communications systems. These devices, or other devices containing chromophores according to the present invention may be used in a method of data transmission wherein light is transmitted through a composition of matter comprising a chromophore according to the present invention. Thus, the present invention provides, in one aspect, a method of telecommunication comprising transmitting light through a composition of matter comprising a chromophore according to the present invention. Such transmission may be accomplished, according to the inventive methods, by directing light through or via a composition of matter comprising a chromophore according to the present invention. Thus, embodiments of the present invention provide, in one aspect, a method of routing light through an optical system comprising transmitting light through or via a composition of matter comprising a chromophore according to the present invention.

In another aspect, an interferometric optical modulator or switch comprises a modulator or switch incorporating an electrooptic polymer or dendrimer. In one embodiment, the modulator or switch includes 1) an input waveguide; 2) an output waveguide; 3) a first leg having a first end and a second end, the first leg being coupled to the input waveguide at the first end and to the output waveguide at the second end; and 4) a second leg having a first end and a second end, the second leg being coupled to the input waveguide at the first end and to the output waveguide at the second end, wherein at least one of the first and second legs comprises a composition of matter comprising a chromophore according to the present invention. The modulator or switch may further comprise an electrode positioned to produce an electric field across the first or second waveguide. While the exemplified modulator or switch is based on a Mach-Zender type of structure, other modulator or switch structures, such as Y-branch structures, evanescent coupling structures, or controlled loss structures, may be within the scope of the invention.

According to the invention, an optical router comprises a plurality of switches, wherein each switch comprises: 1) an input; 2) an output; 3) a first waveguide extending between the input and the output; and 4) a second waveguide aligned to the first waveguide and positioned for evanescent coupling to the first waveguide; wherein at least one of the first and second waveguides comprises a chromophore according to the present invention. Optionally, the plurality of switches is arranged in an array of rows and columns.

These and other aspects according to the present invention are additionally described below.

BRIEF DESCRIPTION OF THE DRAWINGS

FIG. 2B, independently at each occurrence, R is alkyl, aryl or heteroalkyl; $R^1$ is hydrogen, alkyl, aryl or heteroalkyl; Y is O, S or Se; and q is 0 or 1; wherein each of alkyl, aryl and heteroaryl is defined herein.

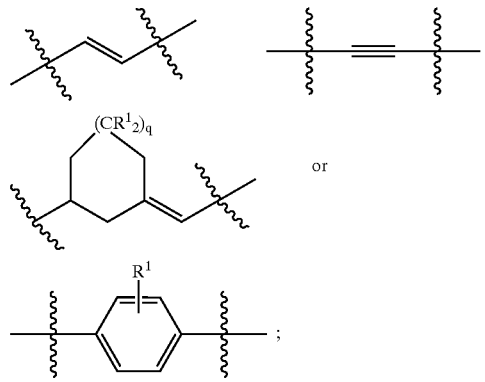

Figure 3A:
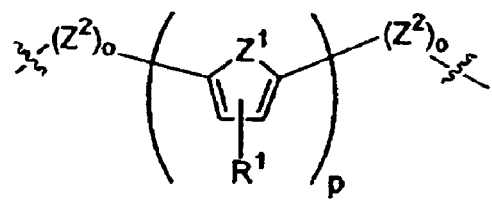
FIGS. 3A and 3B illustrates p-bridges that may be incorporated into a chromophore where, in FIG. 3A independently at each occurrence, $Z^1$ is O, S, Se, $NR^1$, $C(R^1)_2$ or —$C(R^1)$=$C(R^1)$—; p is 0, 1 or 2; o is 0,1 or 2; o+p is at least 1; $R^1$ is hydrogen, alkyl, aryl or heteroalkyl; $Z^2$ is
Figure 3B:
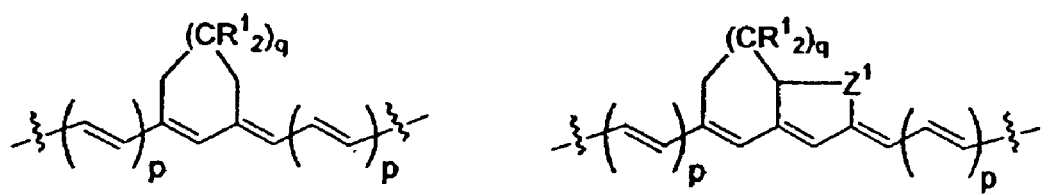
Figure 3B:
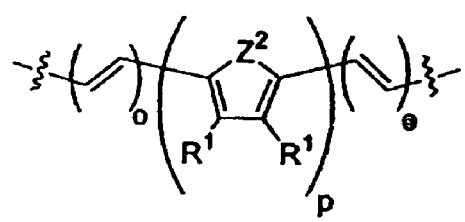

and q is 0 or 1; and in FIG. 3B independently at each occurrence, $R^1$ is hydrogen, alkyl, aryl or heteroalkyl; $Z^1$ is O, Se, $NR^1$, $C(R^1)_2$ or —$C(R^1)$=$C(R^1)$—; p is 0, 1 or 2; o is 1, 2 or 3; o+p is at least 1; and q is 0 or 1.

FIGS. 4A, 4B, 4C, 5A, 5B, 6A, 6B, 7A, 7B, 7C, 8A, 8B, 9A, 9B, 10A, 10B, 11A, 11B, 12A, 12B, 13A, 13B, 14A, 14B, 15A, 15B, 16A, and 16B, each illustrates either general synthetic schemes for preparing chromophores according to the present invention, or specific chromophores according to the present invention.

Figure 17:
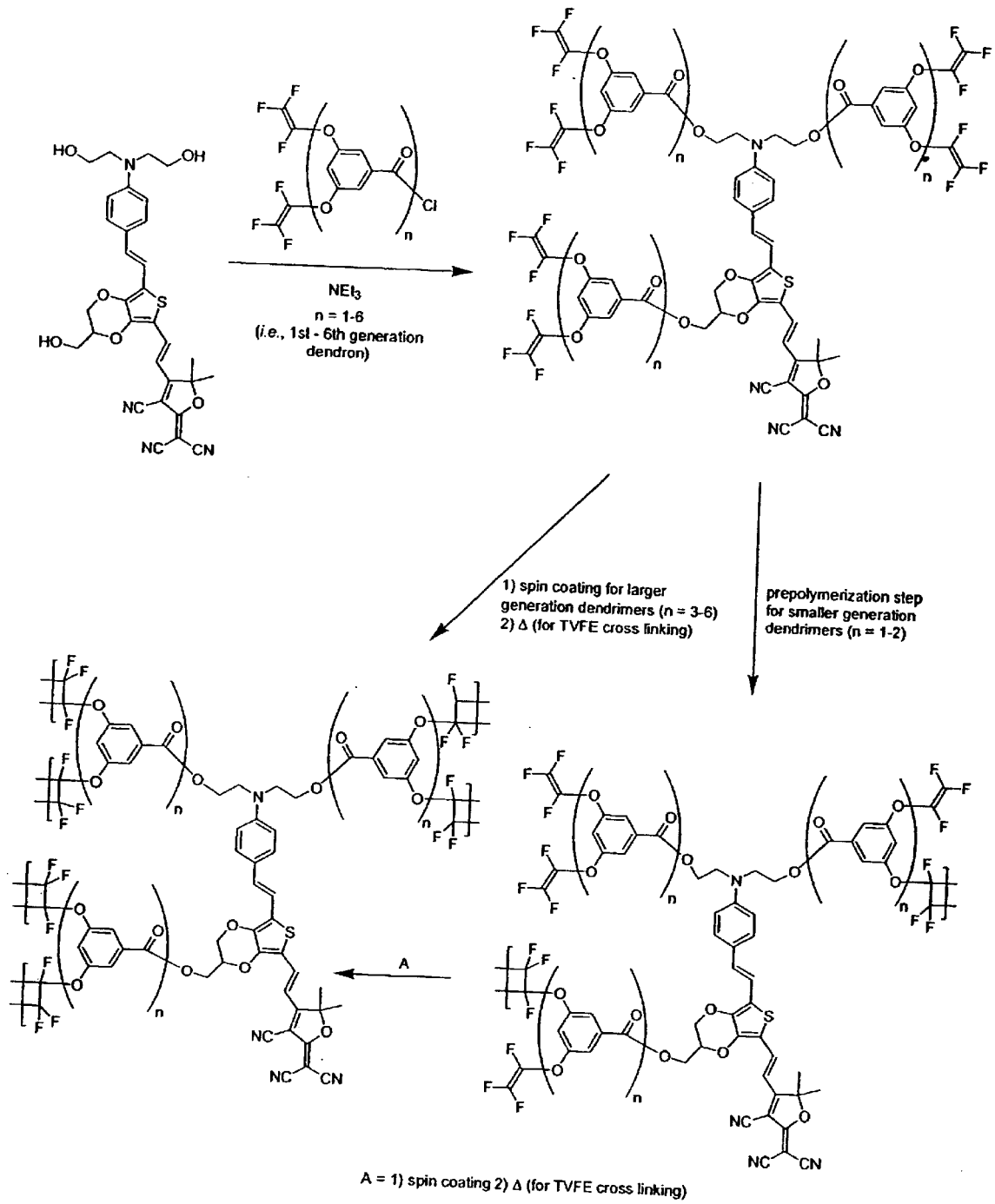

FIG. 17 illustrates a method for preparing a polymer matrix including a chromophore.

Figure 18:
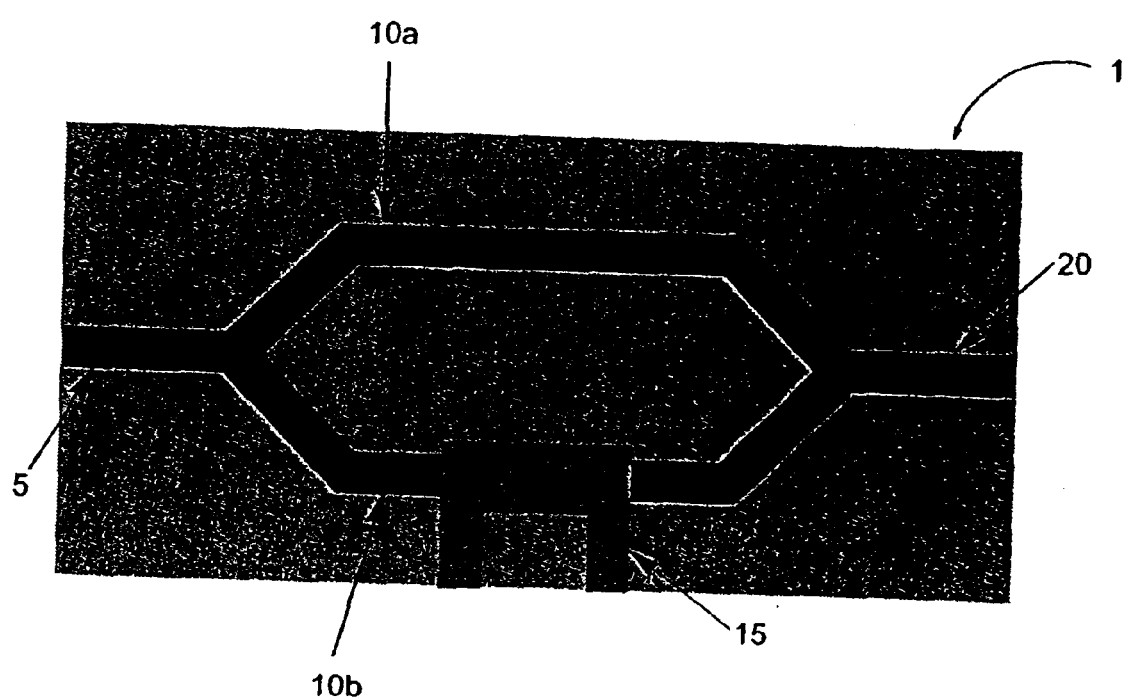

FIG. 18 illustrates a Mach Zehnder modulator (1) having an input (5), an output (20), two legs (10a, 10b) that are both coupled to the input and output, and an electrode (15) positioned near one of the legs.

FIGS. 19, 20, 21, 22, 23, 24, and 25 each illustrates specific examples of preparing chromophores according to the present invention, as described more fully herein.

DETAILED DESCRIPTION OF THE INVENTION

Definitions

In general, all technical and scientific terms used herein have the same meaning as commonly understood to one of ordinary skill in the art to which this invention belongs, unless clearly indicated otherwise. When an element is cited, all of the element's isotopes are implicitly included (e.g., "hydrogen" stands for hydrogen, deuterium, and tritium). If an isotope is identified explicitly, it is represented by a superscript of the atomic number immediately preceding the symbol (i.e., deuterium is "$^2$H" not "D"). For clarification, listed below are definitions for certain terms used herein to describe embodiments according to the present invention. These definitions apply to the terms as they are used throughout this specification, unless otherwise clearly indicated.

As used herein the singular forms "a", "and", and "the" include plural referents unless the context clearly dictates otherwise. For example, "a group" refers to one or more of such groups, while "a chromophore" includes a particular chromophore as well as other family members and equivalents thereof as known to those skilled in the art.

Both substituent groups and molecular moieties are sometimes represented herein with symbols (e.g., R, $R^1$, $\pi$, $\pi^1$, $\pi^2$, D, and A). When the phrase "independently at each occurrence" is used herein in reference to a symbol, that symbol may represent different actual substituent groups or molecular moieties every time the symbol appears in a formula. For example, in the structure

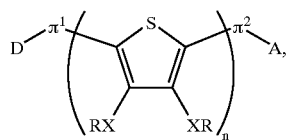

which contains two X groups within each of n repeating units, and X is, i.e., represents, O or S, then the two X groups may be O and O, or O and S, or S and O, or S and S, within a repeating unit, and the selection within one repeating unit is not dependent or related to the selection in a second or third, etc. repeating unit. In other words, "independently at each occurrence" means that what X represents at any one occurrence is completely independent of what X represents at any other occurrence, so long as X represents an atom or moiety within the definition of what may represent. Every symbol, whether the same or different from another symbol, may represent any of the options provided in the definition for the symbol, and this representation is independently selected every time that symbol appears. Thus, when a structure is provided followed by the phrase "wherein, independently at each occurrence", this phrase is meant to indicate that every symbol used in connection with the structure, or within any substructure contained within a structure or substructure, is selected without regard to the selection of the same symbol or a different symbol at any other occurrence of a symbol within that structure or a substructure thereof.

In the chemical structures provided herein, a ring may be shown having a line (the bisecting line) drawn across one of the lines that form the ring, where the bisecting line is connected to a symbol. For example, the following phenol structure has a bisecting line connected to the symbol R.

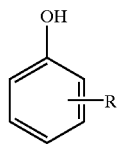

In this situation, the symbol may be bonded to any atom that forms the ring, if that atom is not otherwise shown to be bonded to any particular non-hydrogen substituent. Thus, in the above example of the phenolic compound, the R group may be bonded to as many as five carbons, as shown in the following structure.

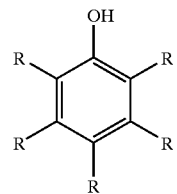

However, it is not necessary that an R group replace each hydrogen on the ring. The R group need not replace any of the hydrogen atoms, or an R group may replace one, or two, or three, or four, or five of the hydrogens, limited only by the total number of hydrogens bonded to the ring atoms. Thus, the phenolic structure shown above "wherein R independently at each occurrence is methyl or hydrogen" would correspond to phenol as wells as several methyl substituted phenols including 2-methyl phenol, 3-methyl phenol, 3,4-dimethylphenol, 2,4,6-trimethylphenol, etc.

"Chromophore" refers to any molecule, aggregate of molecules, or macromolecular structure that absorbs light. Thus, a chromophore can mean a single molecule that absorbs light, an aggregate or macromolecule containing only one absorbing molecule, or an aggregate or macromolecule containing more than one absorbing molecule.

"Electro-optic" (EO) pertains to having optical properties of a material alterable by an electric field.

"Electronic" pertains to electrons in a molecule or on an atom.

"Electric" pertains to electricity and electrical phenomena arising from applied voltages or other signals.

"Temporal stability" refers to long-term retention of a particular property. Temporal stability may be affected by any factor that modifies changes in either intermolecular order or intramolecular chemical structure.

A donor (represented in chemical structures by "D" or "D'''" where n is an integer) is an atom or group of atoms that has a low oxidation potential, wherein the atom or group of atoms can donate electrons to an acceptor "A" through a π-bridge. The donor (D) has a lower electron affinity that does the acceptor (A), so that the chromophore is generally polarized, with relatively less electron density on the donor (D). Typically, a donor group contains at least one heteroatom that has a lone pair of electrons capable of being in conjugation with the p-orbitals of an atom directly attached to the heteroatom such that a resonance structure can be drawn that moves the lone pair of electrons into a bond with the p-orbital of the atom directly attached to the heteroatom to formally increase the multiplicity of the bond between the heteroatom and the atom directly attached to the heteroatom (i.e., a single bond is formally converted to double bond, or a double bond is formally converted to a triple bond) so that the heteroatom gains formal positive charge. The p-orbitals of the atom directly attached to the heteroatom may be vacant or part of a multiple bond to another atom other than the heteroatom. The heteroatom may be a substituent of an atom that has pi bonds or may be in a heterocyclic ring. Exemplary donor groups include but are not limited to $R_2N$—, RX— and the structures shown in FIG. 1A, where R is alkyl (as defined herein), aryl (as defined herein), and heteroaryl (as defined herein), X is O, S, Se, or Te, and n is 1 or 2. Additional exemplary donors are shown in FIG. 1B, wherein independently at each occurrence, R is alkyl, aryl or heteroalkyl; $R^1$ is hydrogen, alkyl, aryl or heteroalkyl; Y is O, S or Se; m is 2, 3 or 4; p is 0, 1 or 2; and q is 0 or 1; wherein each of alkyl, aryl and heteroaryl is defined herein.

Further exemplary donors are illustrated in FIGS. 4A, 4B, 4C, 5A, 5B, 6A, 6B, 7A, 7B, 7C, 8A, 8B, 9A, 9B, 10A, 10B, 11A, 11B, 12A, 12B, 13A, 13B, 14A, 14B, 15A, 15B, 16A, 16B, 19, 20, 21, 22, 23, 24, and/or 25. The total number of heteroatoms and carbons in a donor group is about 30, and the donor group can be substituted further with alkyl (as defined herein), aryl (as defined herein), and heteroaryl (as defined herein). The "donor" and "acceptor" terminology is well known and understood in the art of the present invention. See, e.g., U.S. Pat. Nos. 5,670,091, 5,679,763, and 6,090,332.

Figure 2A:
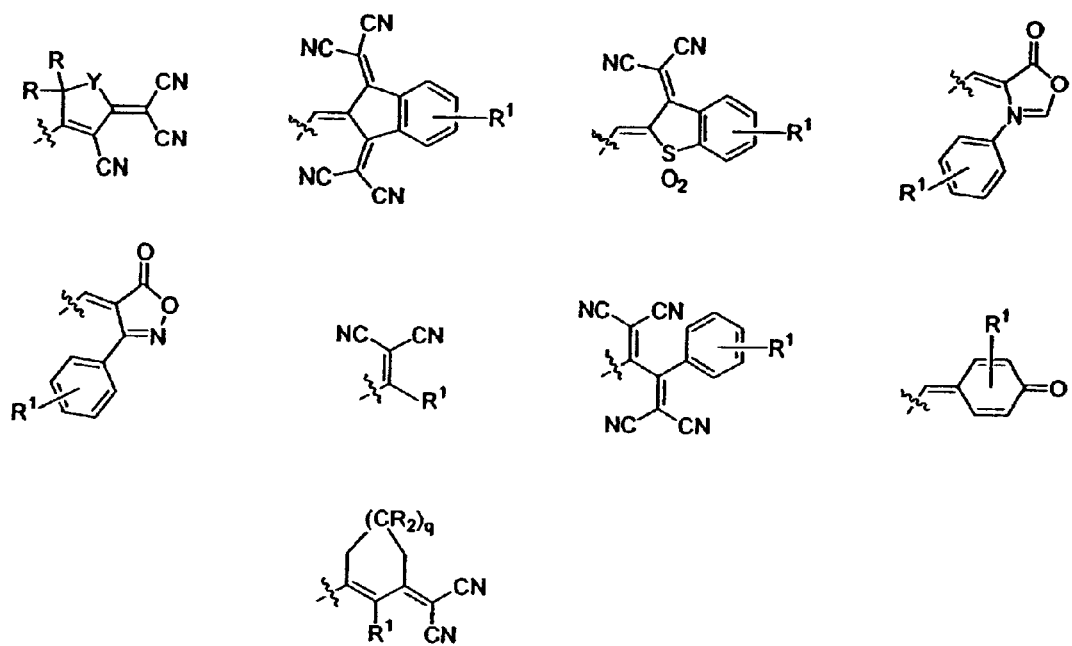
FIGS. 2A and 2B illustrate acceptor moieties (A) that may be incorporated into a chromophore where, in FIG. 2A independently at each occurrence, R is alkyl, aryl, and heteroaryl, X is O, S, Se, or Te, and n is 1 or 2.
Figure 2B:
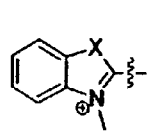
Figure 2B:
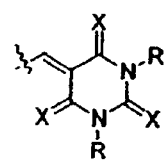
Figure 2B:
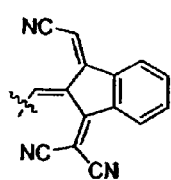
Figure 2B:
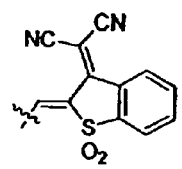
Figure 2B:
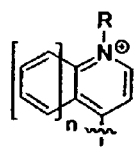
Figure 2B:
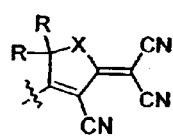
Figure 2B:
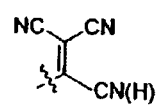
Figure 2B:
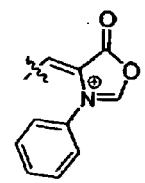
Figure 2B:
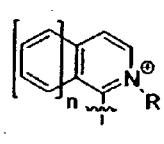
Figure 2B:
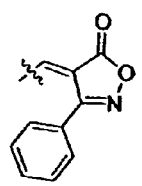
Figure 2B:
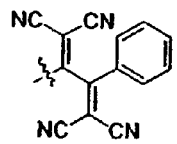
Figure 2B:
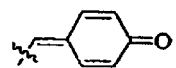

An acceptor (represented in chemical structures by "A" or "A'ⁿ" where n is an integer) is an atom or group of atoms that has a low reduction potential, wherein the atom or group of atoms can accept electrons from a donor through a π-bridge. The acceptor (A) has a higher electron affinity that does the donor (D), so that the chromophore is generally polarized, with relatively more electron density on the acceptor (D). Typically, an acceptor group contains at least one electronegative heteroatom that is part of a pi bond (a double or triple bond) such that a resonance structure can be drawn that moves the electron pair of the pi bond to the heteroatom and concomitantly decreases the multiplicity of the pi bond (i.e., a double bond is formally converted to single bond or a triple bond is formally converted to a double bond) so that the heteroatom gains formal negative charge. The heteroatom may be part of a heterocyclic ring. Exemplary acceptor groups include but are not limited to —$NO_2$, —CN, —CHO, COR, $CO_2R$, —$PO(OR)_3$, —SOR, —$SO_2R$, —$SO_3R$ and the structures shown in FIG. 2A where R is alkyl (as defined herein), aryl (as defined herein), and heteroaryl (as defined herein), X is O, S, Se, or Te, and n is 1 or 2. Additional exemplary acceptor structures are shown in FIG. 2B wherein, independently at each occurrence, R is alkyl, aryl or heteroalkyl; $R^1$ is hydrogen, alkyl, aryl or heteroalkyl; Y is O, S or Se; and q is 0 or 1. Further exemplary acceptors are illustrated in FIGS. 4A, 4B, 4C, 5A, 5B, 6A, 6B, 7A, 7B, 7C, 8A, 8B, 9A, 9B, 10A, 10B, 11A, 11B, 12A, 12B, 13A, 13B, 14A, 14B, 15A, 15B, 16A, 16B, 19, 20, 21, 22, 23, 24, and/or 25. The total number of heteroatoms and carbons in a acceptor group is about 30, and the acceptor group can be substituted further with alkyl (as defined herein), aryl (as defined herein), and heteroaryl (as defined herein). The "donor" and "acceptor" terminology is well known and understood in the art of the present invention. See, e.g., U.S. Pat. Nos. 5,670,091, 5,679,763, and 6,090,332.

A "π-bridge" or "electronically conjugated bridge" (represented in chemical structures by "π" or "π'ⁿ" where n is an integer) is comprised of an atom or group of atoms through which electrons can be delocalized from an electron donor (defined below) to an electron acceptor (defined below) through the orbitals of atoms in the bridge. Such groups are very well known in the art. Typically, the orbitals will be p-orbitals on double ($sp^2$) or triple (sp) bonded carbon atoms such as those found in alkenes, alkynes, neutral or charged aromatic rings, and neutral or charged heteroaromatic ring systems. Additionally, the orbitals can be p-orbitals on atoms such as boron or nitrogen. Additionally, the orbitals may be p, d or f organometallic orbitals or hybrid organometallic orbitals. The atoms of the bridge that contain the orbitals through which the electrons are delocalized are referred to here as the "critical atoms." The number of critical atoms in a bridge can be a number from 1 to about 30. The critical atoms may be substituted with any organic or inorganic group. The substituent may be selected with a view to improving the solubility of the chromophore in a polymer matrix, to enhancing the stability of the chromophore, or to any other purpose. Exemplary p-bridges are illustrated in FIGS. 3A and 3B where, in FIG. 3A independently at each occurrence, $Z^1$ is O, S, Se, $NR^1$, $C(R^1)_2$ or —$C(R^1)$=$C(R^1)$—; p is 0, 1 or 2; o is 0,1 or 2; o+p is at least 1; $R^1$ is hydrogen, alkyl, aryl or heteroalkyl; $Z^2$ is

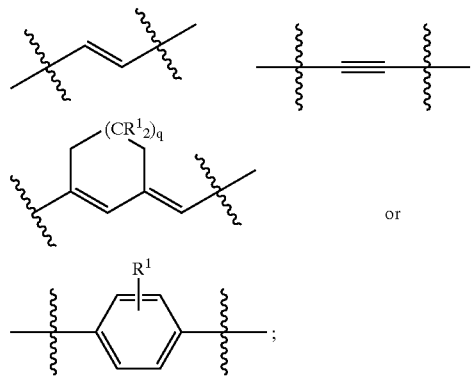

and q is 0 or 1; and in

FIG. 3B independently at each occurrence, $R^1$ is hydrogen, alkyl, aryl or heteroalkyl; $Z^1$ is O, S, Se, $NR^1$, $C(R^1)_2$ or —$C(R^1)$=$C(R^1)$—; p is 0, 1 or 2; o is 1, 2 or 3; o+p is at least 1; and q is 0 or 1. Additional exemplary π-bridges are illustrated in FIGS. 1A, 1B, 2A, 2B, 3A, 3B, 4A, 4B, 4C, 5A, 5B, 6A, 6B, 7A, 7B, 7C, 8A, 8B, 9A, 9B, 10A, 10B, 11A, 11B, 12A, 12B, 13A, 13B, 14A, 14B, 15A, 15B, 16A, 16B, 17, 19, 20, 21, 22, 23, 24, and/or 25. In one embodiment, substituents on the critical atoms are selected from: "alkyl" as defined below, "aryl" as defined below, or "heteroalkyl" as defined below. One or more atoms, with the exception of hydrogen, on alkyl (defined below), aryl (defined below), or heteroalkyl (defined below) substituents of critical atoms in the bridge may be bonded to atoms in other alkyl (defined below), aryl (defined below), or heteroalkyl (defined below) substituents to form one or more rings.

"Donor coupling" or "π bridge and/or donor coupling" refers to the synthetic chemical step or steps that achieves covalent attachment of a first chemical group containing a donor to a second selected chemical structure. The step may be divided into multiple steps, wherein the first step covalently attaches a π bridge that is also reactive and the second step covalently attaches a donor group. Typically, the coupling involves either reacting a π bridge or donor group containing a carbonyl with a selected chemical structure containing at least one acidic proton, or reacting a π bridge or donor group containing at least one acid proton with a selected chemical structure containing a reactive carbonyl group. Suitable donor coupling reactions are well known to those of ordinary skill in the art.

"Acceptor coupling" or "π bridge and/or acceptor coupling" refers to the synthetic chemical step or steps of covalently attaching a first chemical group containing an acceptor to a second selected chemical structure. The step maybe divided into multiple steps, wherein the first step covalently attaches a π bridge that is also reactive and the second step covalently attaches an acceptor group. Typically, the coupling involves either reacting a π bridge or acceptor group containing a carbonyl with a selected chemical structure containing at least one acidic proton or reacting a π bridge or acceptor group containing at least one acid proton with a selected chemical structure containing a reactive carbonyl group. Suitable acceptor coupling reactions are well known to those of ordinary skill in the art.

A dendron is a branched substituent that has regularly repeating subunits. A dendrimer is a macromolecular structure that contains a "core" surrounded by one or more dendrons. Often in the art, the terms dendron and dendrimer are used interchangeably. One or more dendrons may be attached to a chromophore according to the present invention.

As used herein, "R" or "R′″" where n is an integer refers to a substituent on an atom or a group of atoms (e.g., a ring). Unless otherwise specifically assigned, —R represents any single atom or any one of the substituent groups defined below. When there is more than one —R in a molecule, the "—R" may independently at each occurrence refer to a single atom or any one of the substituent groups defined below.

The following definitions apply to substituent groups. A given substituent group can have a total number of carbons atoms ranging from 1 to about 200:

1. "Alkyl" is a saturated or unsaturated, straight or branched, cyclic or multicyclic aliphatic (i.e., non-aromatic) hydrocarbon group containing from 1 to about 30 carbons. The hydrocarbon group has, in various embodiments: zero branches (i.e., is a straight chain), one branch, two branches, or more than two branches; and/or is saturated or is unsaturated (where an unsaturated alkyl group may have one double bond, two double bonds, more than two double bonds, and/or one triple bond, two triple bonds, or more than three triple bonds); and/or a cyclic structure or is acyclic. Exemplary alkyl groups include $C_1$alkyl (i.e., —$CH_3$ (methyl)), $C_2$alkyl (i.e., —$CH_2CH_3$ (ethyl), —$CH=CH_2$ (ethenyl) and —$C\equiv CH$ (ethynyl)) and $C_3$alkyl (i.e., —$CH_2\ _2CH_3$ (n-propyl), —$CH(CH_3)_2$ (i-propyl), —$CH=CH—CH_3$ (1-propenyl), —$C\equiv C—CH_3$ (1-propynyl), —$CH_2$—$CH=CH_2$ (2-propenyl), —$CH_2$—$C\equiv CH$ (2-propynyl), —$C(CH_3)=CH_2$ (1-methylethenyl), —$CH(CH_2)_2$ (cyclopropyl), and adamantly. The term "alkyl" also includes groups where at least one of the hydrogens of the hydrocarbon group is substituted with at least one of the following: alkyl; "aryl" as defined below; or "heteroalkyl" as defined below. One or more of the atoms in an alkyl group, with the exception of hydrogen, can be bonded to one or more of the atoms in an adjacent alkyl group, aryl group (aryl as defined below), or heteroalkyl group (heteroalkyl as defined below) to form one or more ring;

2. "Aryl" is a monocyclic or polycyclic aromatic ring system or a heteroaromatic ring system containing from 3 to about 30 carbons. The ring system may be monocyclic or fused polycyclic (e.g., bicyclic, tricyclic, etc.). Preferred heteroatoms are nitrogen, oxygen, sulfur, and boron. In various embodiments, the monocyclic aryl ring is C5–C10, or C5–C7, or C5–C6, where these carbon numbers refer to the number of carbon atoms that form the ring system. A C6 ring system, i.e., a phenyl ring, is a preferred aryl group. A C4-S ring system (i.e., a thiophene) is another preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group. The term "aryl" also includes groups where at least one of the hydrogens of the aromatic or heteroaromatic ring system is substituted further with at least one of the following: alkyl; halogen; or heteroalkyl (as defined below). One or more of the atoms in an aryl group, with the exception of hydrogen, can be bonded to one or more of the atoms in an adjacent alkyl group, aryl group, or heteroalkyl group (heteroalkyl as defined below) to form one or more rings;

3. "Heteroalkyl" or "Heteroaryl" is an alkyl or aryl group (as defined herein) wherein one or more, including all, of the carbon atoms or hydrogen atoms is replaced with a heteroatom. Preferred heteroatoms are nitrogen, oxygen, sulfur, silicon, and halogen. A heteroatom may, but typically does not, have the same number of valence sites as the carbon or hydrogen atom it replaces. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon will be deleted. Likewise, if carbon is replaced with halogen (valence of one), then three (i.e., all) of the hydrogens formerly bonded to the replaced carbon must be deleted. Examples of heteroalkyls derived from alkyls by replacement of carbon or hydrogen with heteroatoms is shown immediately below. Exemplary heteroalkyl groups are methoxy (—$OCH_3$), amines (—$CH_2NH_2$), nitriles (—CN), carboxylic acids (—$CO_2H$), other functional groups, and heteroatom-containing dendrons. The term "heteroalkyl" also includes groups where at least one of the hydrogens of carbon or a heteroatom of the heteroalkyl may be substituted with at least one of the following: alkyl; aryl; and heteroalkyl. One or more of the atoms in a heteroalkyl group, with the exception of hydrogen, can be bonded to one or more of the atoms in an adjacent alkyl group, aryl group, or heteroalkyl group to form one or more rings.

| Alkyl | Heteroalkyl |
|---|---|

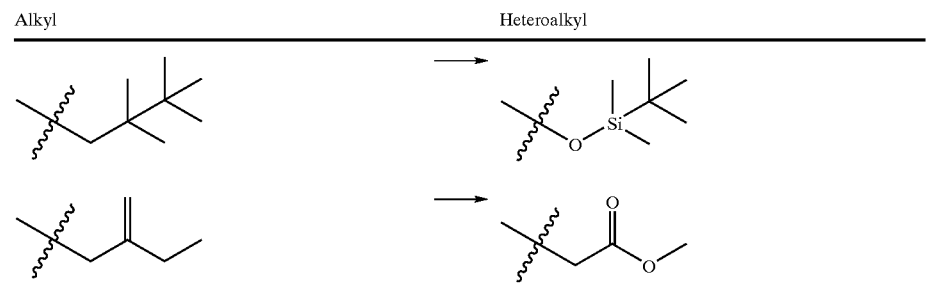

| Alkyl | Heteroalkyl |
|---|---|

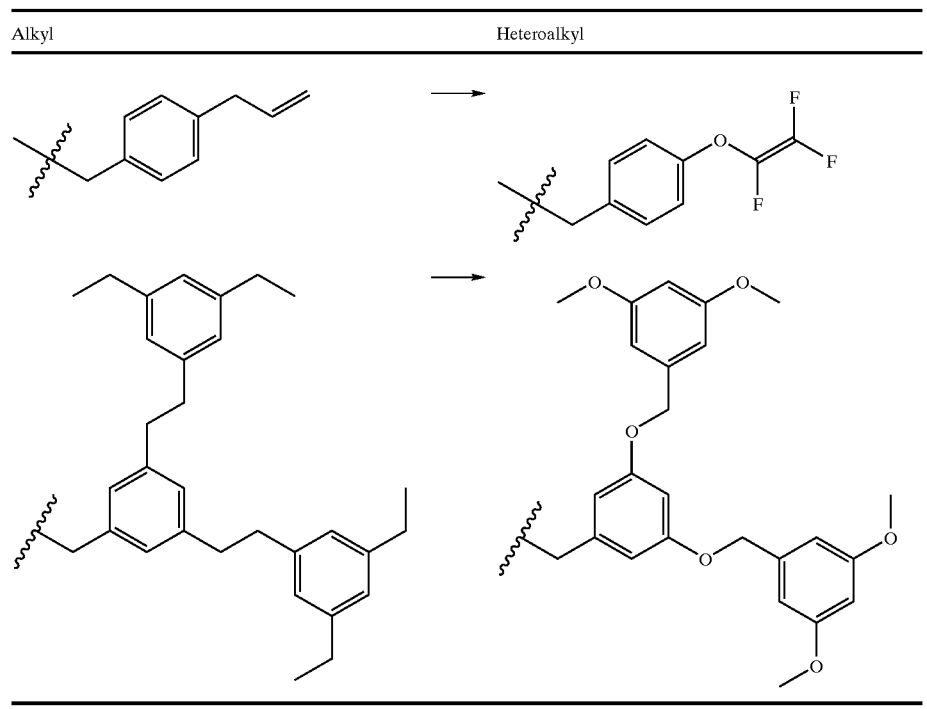

The substituent list that follows is not meant to limit the scope of the definitions above or the inventions described below, but rather merely contains examples of substituents within the definitions above: 1) (alkyl) —$CH_3$, -i-Pr, -n-Bu, -t-Bu, -i-Bu, —$CH_2CH$=$CH_2$ (allyl) —$CH_2C_6H_5$ (benzyl); 2) (heteroalkyl) —$X_{(0-1)}(CH_2)_{(0-12)}(CF_2)_{(0-12)}(CH_2)_{(0-12)}CH_pZ_q$ (where X includes —O, —S, —$CO_2$— (ester), Z=halogen, p=0–3, q=0–3, and p+q=3) and branched isomers thereof, —$X_{(0-1)}(CH_2)_{(0-12)}(CF_2)_{(0-12)}(CH_2)_{(0-12)}Z$ (where X includes —O, —S, —$CO_2$— (ester), Z includes —OH, —$NH_2$, —$CO_2H$ and esters and amides thereof, —COCl, and —NCO) and branched isomers thereof, —$OCFCF_2$ (TFVE), —$Si(CH_3)_3$ (TMS), —$Si(CH_3)_2$(t-Bu) (TBDMS), —$Si(C_6H_5)$ (TPS), —$Si(C_6F_5)_3$, and dendrons such as illustrated in the dendrimers discussed in Bosman et al., Chem. Rev. 1999, 99, 1665–1688; 3) (aryl) —$C_6H_5$ (phenyl), p-, o-, and/or m-substituted phenyl (with substituents independently selected from —$CH_3$, -i-Pr, -n-Bu, -t-Bu, -i-Bu, —$X_{(0-1)}(CH_2)_{(0-1)}(CF_2)_{(0-12)}(CH_2)_{(0-12)}CH_pZ_q$ (where X includes —O, —S, —$CO_2$— (ester), Z=halogen, p=0–3, q=0–3, and p+q=3) and branched isomers thereof, —$X_{(0-1)}(CH_2)_{(0-12)}(CF_2)_{(0-12)}(CH_2)_{(0-12)}Z$ (where X includes —O, —S, —$CO_2$— (ester), Z includes —OH, —$NH_2$, —$CO_2H$ and esters and amides thereof, —TFVE, —COCl, and —NCO) and branched isomers thereof, —$Si(CH_3)_3$ (TMS), —$Si(CH_3)_2$(t-Bu) (TBDMS), —$CH_2CH$=$CH_2$ (allyl), and TFVE) and dendrons as illustrated in the dendrimers discussed in Bosman et al., Chem. Rev. 1999, 99, 1665 or U.S. Pat. No. 5,041,516.

Overview

Historically, an NLO chromophore (also known as a "push-pull" chromophore) comprises three fundamental building blocks represented by the general formula D-π-A. The D-π-A arrangement is critical to achieve large second order NLO effects, and the molecular figure of merit for NLO molecules, which is the first molecular electronic hyperpolarizability (β, sometimes given as $\mu\beta$, where $\mu$ is the dipole moment of the chromophore), can be tuned and optimized by changing the electronic properties of any one of D, π, or A, see Gorman and Marder Proc. Natl. Acad. Sci, USA 1993, 90, 11297. Molecular NLO effects can be translated into bulk EO activity in a material by aligning molecules in one direction by applying an electric field.

Generally, for a given D-π-A chromophore, any one of D, π, or A can be derivatized with groups that do not significantly alter the electronic properties of the chromophore. Such derivatization may be important, for example, in order either to translate high molecular $\mu\beta$ into high EO activity of the bulk material or to increase temporal stability related to relaxation of the aligned dipoles, see Dalton et al., J. Mater. Chem. 1999, 9, 1905–1920. Thus, a high $\mu\beta$ chromophore can be derivatized to, for example: modify its solubility in a polymer matrix; allow its covalent attachment to other molecules or polymers; and spatially hinder intermolecular interactions with other chromophores. In various other aspects according to the present invention provides new design and synthesis of chromophore-containing matrices, including the processing thereof into EO materials. For instance, the chromophores according to the present invention may include chemical groups that impart steric bulk and/or solubility properties that enhance performance and/or processing into a matrix.

The embodiments disclosed herein are generally directed to chromophore-containing electro-optic (EO) materials that promise the development of marketability, good device quality, and high performance. Materials for EO device applications preferably have the following properties:
1. Large electro-optic coefficient;
2. High optical transparency at operational frequency (low absorption loss);
3. High optical quality (determined by homogeneity of polymer films);
4. Good mechanical properties such as flexibility; and
5. Long term temporal stability of EO activity.

In one aspect, chromophores are comprised of new electron donor groups (D), new π-bridges or substructures thereof (π), and/or new electron acceptor groups (A).

In another aspect, chromophores incorporate chemical groups that modify the properties of the chromophores. For instance, the chromophores according to the present invention may incorporate a group that enhances the solubility of the chromophore in a matrix, particularly a polymeric matrix. As another example, the chromophore may incorporate a group that imparts certain desirable steric demands to the chromophore.

The chromophores may include a substituent group that affects the spatial relationship of a chromophore to another chromophore. Desirably, the substituent group will impede a chromophore from getting too close to another chromophore; such substituent groups are typically bulky alkyl or heteroalkyl groups. Dendrons are preferred bulky substituent groups, and can be incorporated into any chromophore that includes an aliphatic or aromatic alcohol functional group, see U.S. Pat. No. 5,041,516. Moreover, one skilled in the art would recognize that there are other functional groups that may be included in a chromophore and that can be utilized to covalently attach dendrons to the chromophore, where such functional groups include amines, carboxylic acids, alkyl bromides, isocyantes, and isothiocyantes. Separating the chromophores from one another can reduce intermolecular electrostatic interaction between the chromophores, consequently reducing optical loss arising from light scattering, and also increase the poling efficiencies.

In another aspect, the chromophores have been designed to modify the number of active hydrogens adjacent to the chromophore donor, acceptor, and/or π-bridge (e.g., allylic and benzylic hydrogens). Active hydrogens provide reactive sites for photochemical processes and are desirably eliminated from chromophores. Not only are those sites prone to radical attack, but they also can easily generate radicals upon exposure to light irradiation. Furthermore, allylic hydrogen(s) can participate in an "ene" reaction with singlet oxygen, see Nicholas J. Turro, *Modern Molecular Photochemistry*, University Science Books, Mill Valley, Calif., 1991.

In another aspect, the chromophores incorporate five membered-rings that restrict the torsional freedom of donors and acceptors with respect to π-bridges. In some embodiments, five-membered rings, rather than six-membered rings, are desirably incorporated into chromophores to provide better p-orbital overlap over an extended conjugation system. Six membered polyenes such as isophorone have structural conformations that can lead to somewhat twisted π-conjugation.

In another aspect, chromophores incorporate bulky side groups such as adamantane. Positioning such bulky groups on bridges can create quasi-spherical molecular structures, which can highly reduce chromophore-chromophore electrostatic interactions. Furthermore, one skilled in the art would recognize that dendrons can be readily incorporated onto donors, acceptors, and π-bridges, making NLO dendrimers.

In another aspect, chromophores have reduced absorption within the 750–800 nm region for application at 1300 nm and 1550 nm. Conventional electron acceptors have multiple electron withdrawing groups (such as 3 CN groups on FTC acceptor) that exert both inductive and resonant effect on electron density delocalization of chromophore. One or more (but typically not all) of those groups can be substituted by with a $CF_3$ group that only has an inductive effect.

DETAILED DESCRIPTION OF THE PREFERRED EMBODIMENTS

In one aspect, chromophores are structured according to the formula D1:

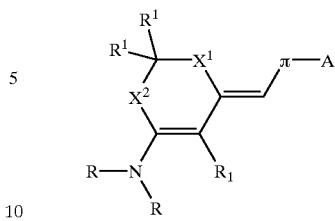

D1 wherein, independently at each occurrence, $X^1$=O or S; $X^2$=O, S, or a single bond; R is alkyl, aryl, or heteroalkyl; $R^1$ is hydrogen, alkyl, aryl, or heteroalkyl; π is a bridge that provides electron conjugation to the A group, and A is an organic electronic acceptor group having high electron affinity relative to the remainder of the chromophore. Either the p or A group can be substituted with one or more halogen, alkyl, aryl, or heteroalkyl substituents.

Figure 4A:
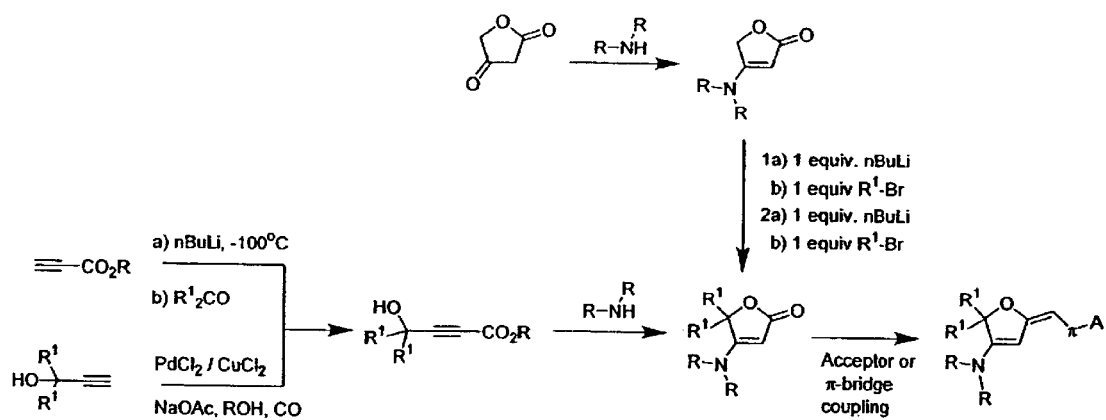
Figure 4B:
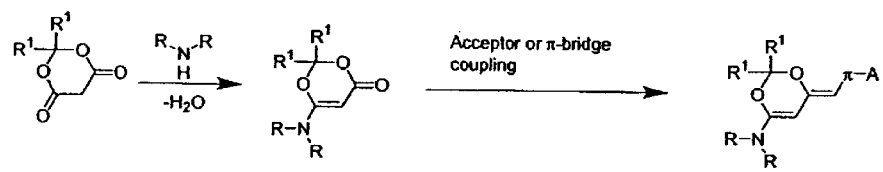

Chromophores according to formula D1 may be prepared as outlined in FIGS. 4A and 4B using reactions that are known to those skilled in the art, see *Tet. Lett.* 1987, 28, 1857; *J. Am. Chem. Soc.* 1986, 108, 800; *J. Org. Chem.* 1987, 52, 2378; *Chem. Hetero. Comp.* (NY) 2000, 35(10), 1150; *Synthesis* 1977, 12, 869; *Mendeleev Comm.* 2001, 1, 17; and *Tet. Lett.* 1988, 29(13), 1489. In one approach, chromophores of formula D1 may be prepared as shown in FIG. 4A by condensing a secondary amine with either a ketone or ester, or by condensing a secondary amine with a γ-hydroxy alkynylester to produce an β-aminounsaturated ester. The resulting β-aminounsaturated ester may optionally be alkylated adjacent to the amino nitrogen when $X^2$ is a single bond and $X^1$ is O or S, in order to incorporate $R^1$ groups into the molecule. Thereafter, selected π bridges and acceptors may be incorporated into the chromophore. Essentially the same procedure may be followed with diesters as shown in FIG. 4B.

Figure 4C:
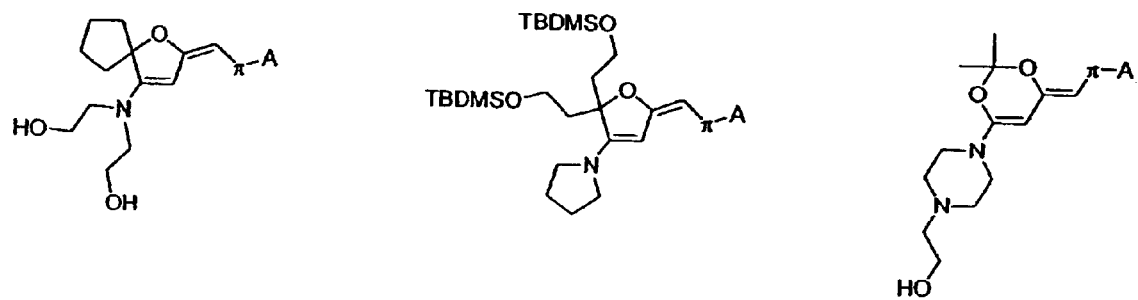

FIG. 4C shows examples of D1 chromophores, which are not meant to limit the scope of the invention, that may be prepared by the methods shown in FIG. 4A. One skilled in the art would recognize that there are many different variants of D1 chromophores that could be prepared by the methods in FIG. 4A without deviating from the scope of the invention.

In another aspect, chromophores which have 5- or 6-membered ring-locked π bridges that contain no reactive allylic hydrogens according to the formula B1

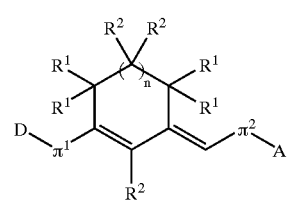

B1 wherein, independently at each occurrence, $π^1$ is absent or a bridge that provides electronic conjugation between D and the remainder of the molecule; $π^2$ is absent or a bridge that provides electronic conjugation between A and the remainder of the molecule; $R^1$ is halogen, alkyl, aryl, or heteroalkyl; $R^2$ is hydrogen, halogen, alkyl, aryl, or heteroalkyl; n=0 or 1; D is an electron donating group having low electron affinity relative to the electron affinity of A; and A is an electron accepting group having high electron affinity relative to the electron affinity of D.

Figure 5A:
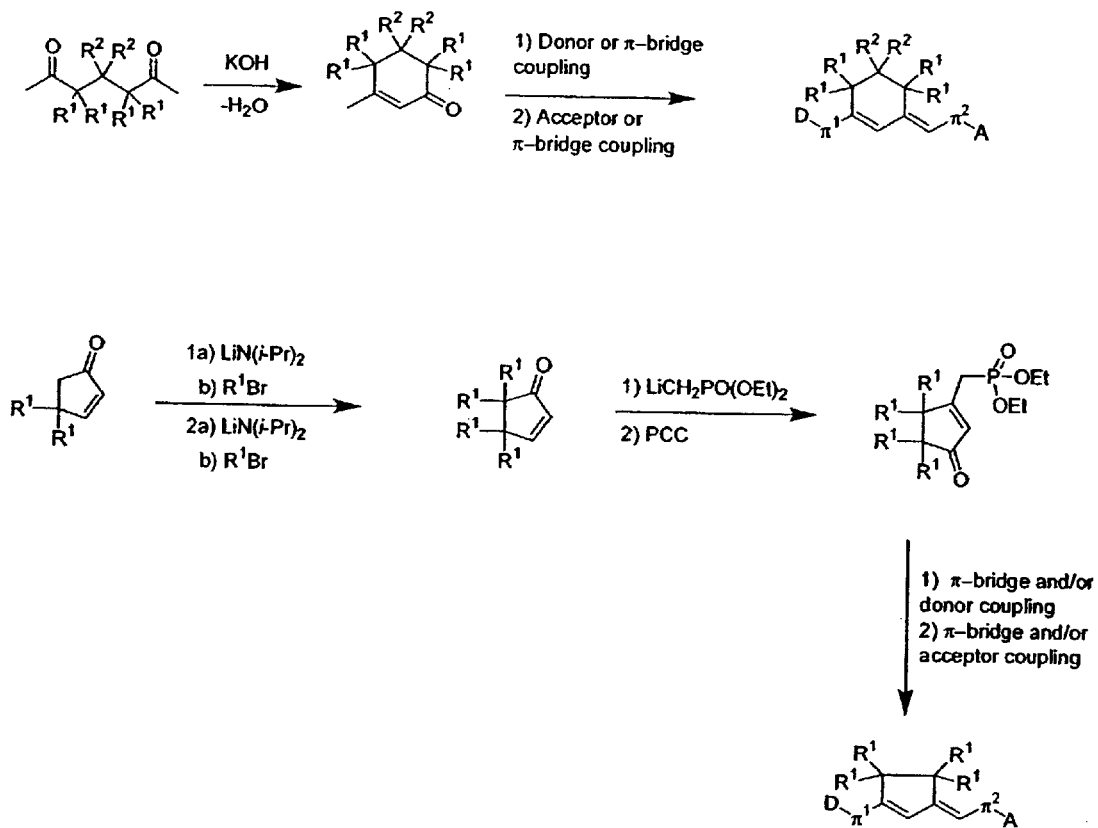
Figure 5B:
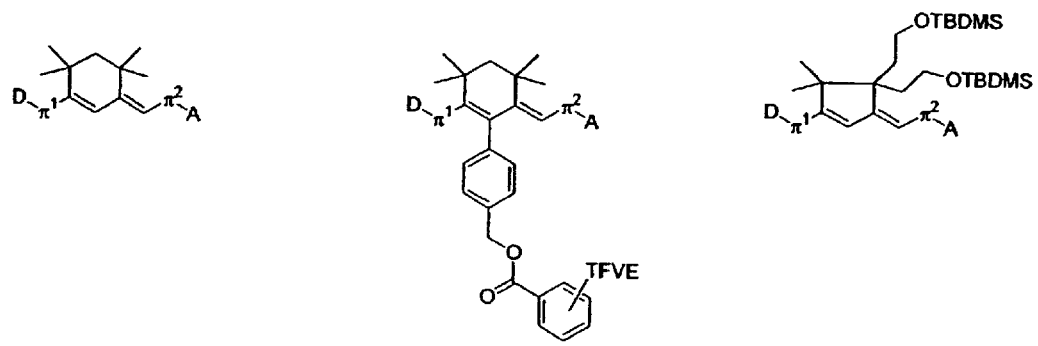

Chromophores according to formula B1 may be prepared using reactions that are known to those skilled in the art, see Chem. Ber. 1985, 118(2), 704; J. Chem. Soc., Perkins Trans. 2 1996, 1455; Tet. Lett. 1989, 30(9), 1033; J. Am. Chem. Soc. 1988, 110, 4625, J. Org. Chem. 1977, 42, 2520; J. Am. Chem. Soc. 1980, 102, 5866; Acc. Chem. Res. 1979, 12, 61; Synthesis 1983, 429; Tet. Lett. 2000, 41(5), 763; Org. Lett. 1999, 1(3), 391; J. Org. Chem. 1990, 55(6); 1909, J. Chem. Soc. B 1969, 4, 449. For example, as shown in FIG. 5A, 1) base induced cyclization or alkylation of cyclopentene derivatives; 2) when n=0, addition of a methyl phosphonate ester followed by oxidative isomerization; 3) π bridge and/or donor coupling; and 4) π bridge and/or acceptor coupling. Shown in FIG. 5B are examples of B1 chromophores, which are not meant to limit the scope of the invention, that may be prepared by the methods shown in FIG. 5A. One skilled in the art would recognize that there are many different variants of B1 chromophores that could be prepared by the methods in FIG. 5A without deviating from the scope of the invention.

In another aspect, chromophores contain 5- or 6-membered ring-locked heterocyclic π bridges according to formula B2:

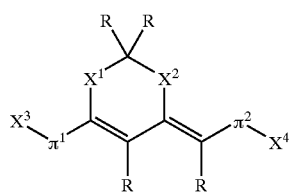

B2 wherein, independently at each occurrence, $\pi^1$ is absent or a bridge that provides electronic conjugation between $X^3$ and the remainder of the molecule; $\pi^2$ is absent or a bridge that provides electronic conjugation between $X^4$ and the remainder of the molecule; either $X^3$ is D and $X^4$ is A or $X^3$ is A and $X^4$ is D; D is an electron donating group having low electron affinity relative to the electron affinity of A; A is an electron accepting group having high electron affinity relative to the electron affinity of D; $X^1$ is O or S; $X^2$ is O, S, a single bond, or $CR_2$; R is hydrogen, alkyl, aryl, or heteroalkyl; and $X^3$, $X^4$, $\pi^1$, and $\pi^2$ can be further substituted with halogen, alkyl, aryl, and heteroalkyl.

Figure 6A:
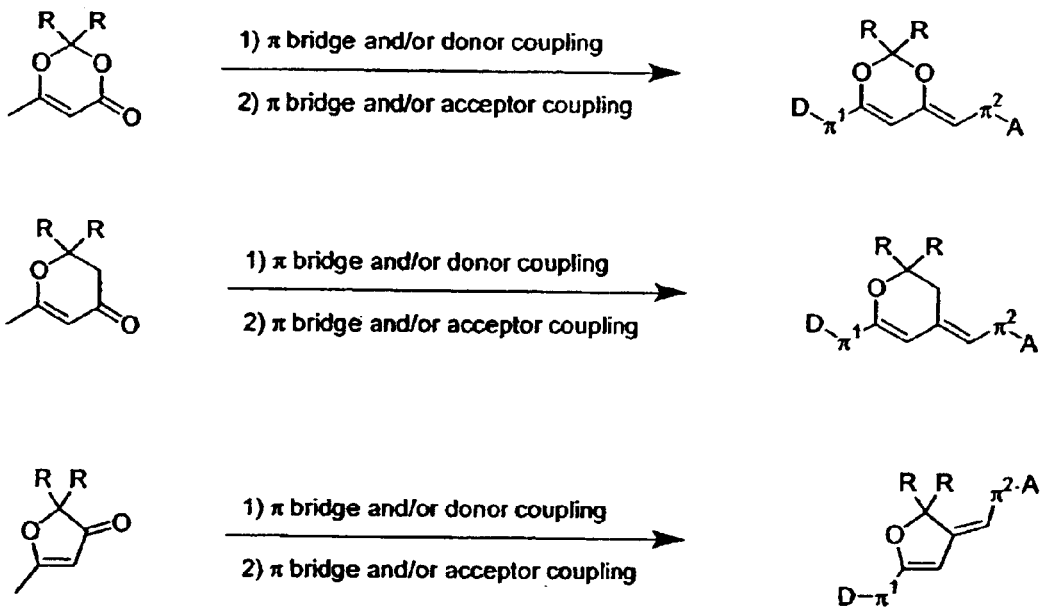
Figure 6B:
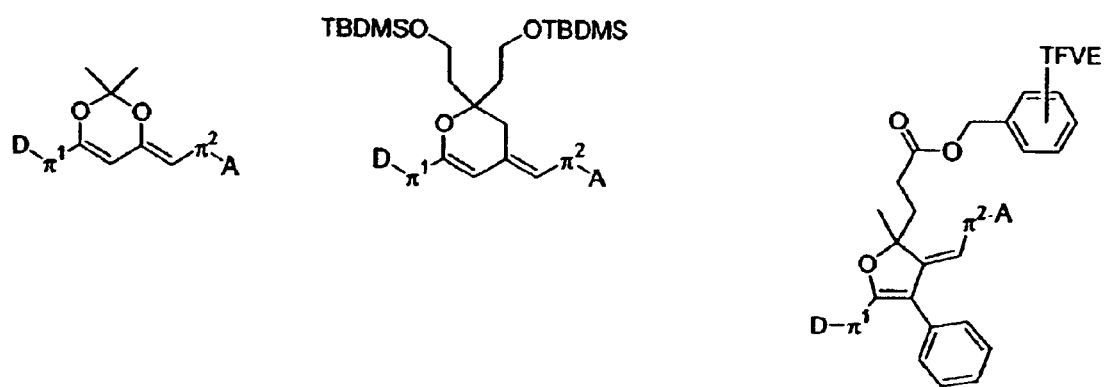

Chromophores according to formula B2 may be prepared using reactions that are known to those skilled in the art, see Syn Lett. 1995, 503; J. Org. Chem. 1988, 53(9), 2011; Syn. Comm. 1988, 18(9), 949; Helv. Chim. Acta. 1991, 74(1), 27. For example, as shown in FIG. 6A: 1) π bridge and/or donor may be coupling to a selected unsaturated cyclic ketone or ester, followed by 2) π bridge and/or acceptor coupling. Shown in FIG. 3B are examples of B2 chromophores, which are not meant to limit the scope of the invention, that may be prepared by the methods shown in FIG. 6A. One skilled in the art would recognize that there are many different variants of B2 chromophores that could be prepared by the methods in FIG. 6A without deviating from the scope of the invention.

In another aspect, the invention provides chromophores comprising thiophene π bridges where these bridges to not contain allylic protons, as shown in formula B3:

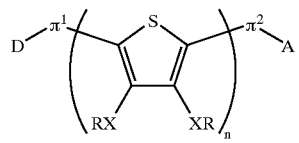

B3 wherein, independently at each occurrence, $\pi^1$ is absent or a bridge that provides electronic conjugation between D and the remainder of the molecule; $\pi^2$ is absent or a bridge that provides electronic conjugation between A and the remainder of the molecule; D is an electron donating group having low electron affinity relative to the electron affinity of A; A is an electron accepting group having high electron affinity relative to the electron affinity of D; X is O or S; R is alkyl, aryl, or heteroalkyl; n=1–4; and any one of $\pi^1$, $\pi^2$, D, or A can be further independently substituted with halogen, alkyl, aryl, or heteroalkyl. In B3, the two R groups may, again independently at each opportunity, join together to form a heterocyclic ring including the two "X" groups to which the two R groups are bonded.

Figure 7A:
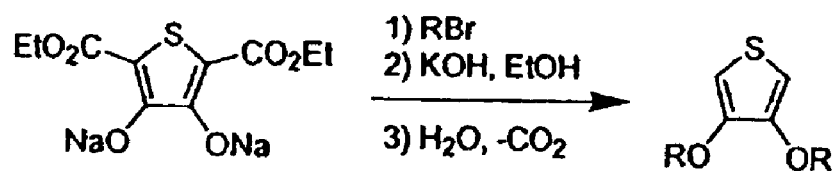
Figure 7B:
Figure 7B:
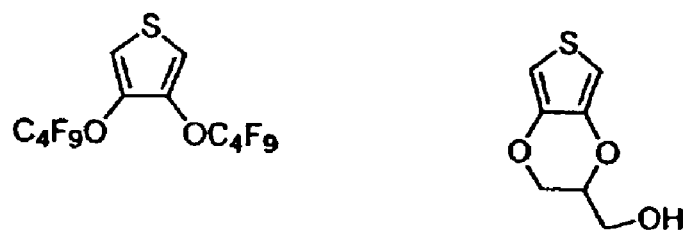
Figure 7C:
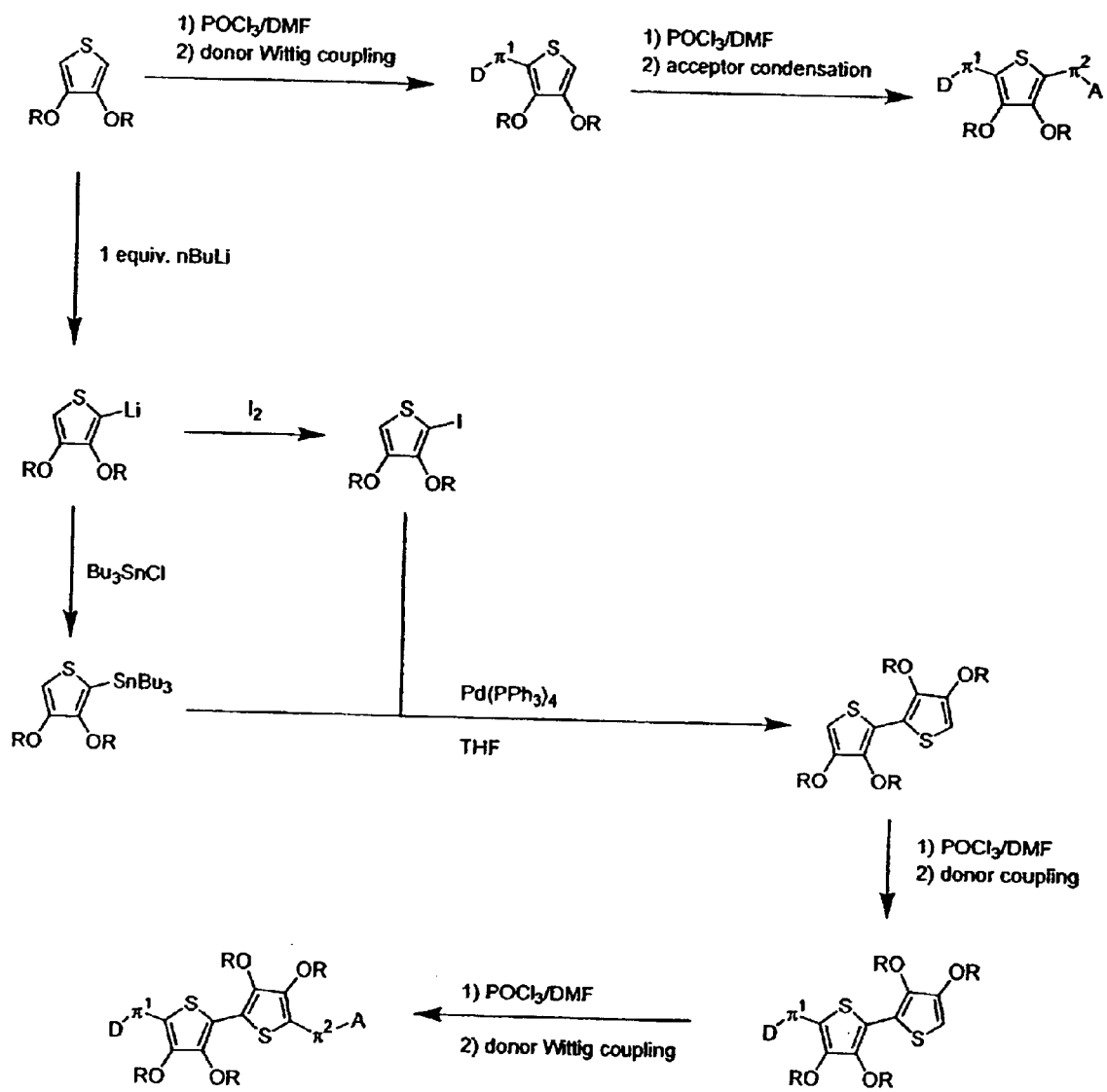

Chromophores according to formula B3 may be prepared using reactions that are known to those skilled in the art, see Synth. Comm. 1996, 26(11), 2205; Tel. Lett. 2001, 42, 1507; J. Am. Chem. Soc. 2001, 123(19), 4643; Chem. Mater. 1996, 8(11), 2659; J. Chem. Soc. Perkins Trans. 1 1997, 1957; Chem. Comm. 2000, 17, 1597. For instance, as shown in FIG. 7A, chromophores of formula B3 may be prepared by: 1) when n=1, formylation of the dialkoxythiophene and coupling of a π bridge and/or donor; and 2) formylation and coupling of a π bridge and/or acceptor. Chromophores where n=2, 3, or 4 may be prepared by using well known methodology in oligothiophenes synthesis as shown in FIG. 7C, by: 1) conversion of the lithiated dialkoxythiophene to both an iodide and a Stille tin reagent; 2) Stille coupling of the tin reagent with the iodide; 3) formylation and coupling of a π bridge and/or donor; and 4) formylation and coupling of a π bridge and/or acceptor. Shown in FIG. 7B are examples of dialkoxy thiophenes, which are not meant to limit the scope of the invention, that may be used to prepare B3 chromophores by the methods shown in FIG. 7A. One skilled in the art would recognize that there are many different variants of B3 chromophores that could be prepared by the methods in FIG. 7A without deviating from the scope of the invention.

In another aspect, the invention provides chromophores comprising fused thienylthiophene π bridges according to the formula B4:

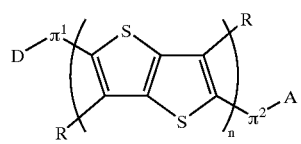

B4 wherein, independently at each occurrence, $\pi^1$ is absent or a bridge that provides electronic conjugation between D and the remainder of the molecule; $\pi^2$ is absent or a bridge that provides electronic conjugation between A and the remainder of the molecule; D is an electron donating group having low electron affinity relative to the electron affinity of A; A is an electron accepting group having high electron affinity relative to the electron affinity of D; R is independently at each occurrence halogen, alkyl, aryl, or heteroalkyl; n=1–4; and any one of $\pi^1$, $\pi^2$, D, or A can be further independently substituted with one or more halogen, alkyl, aryl, or heteroalkyl.

Figure 8A:
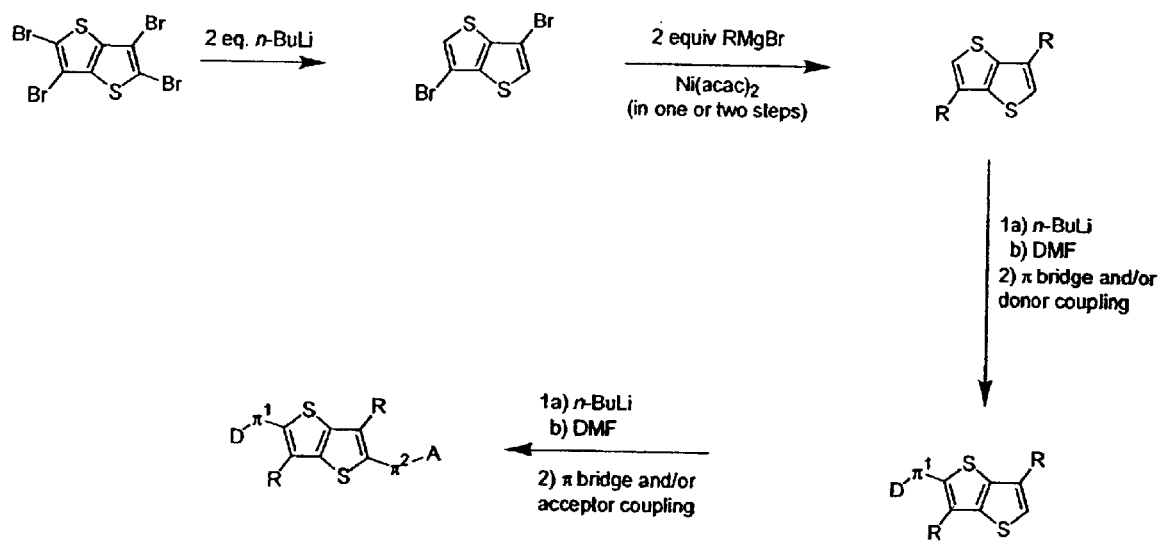
Figure 8B:
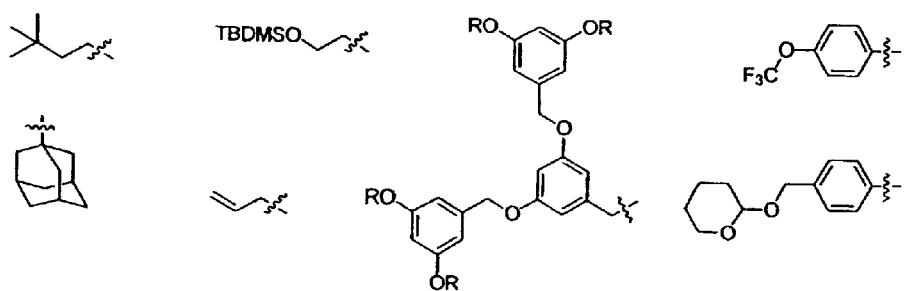

Chromophores according to formula B4 may be prepared using reactions that are known to those skilled in the art, see *J. Chem. Soc. Perkins Trans* 1 1997, 22, 3465; *J. Chem. Soc. Perkins Trans.* 2 1996, 1377; *Heterocycles* 1994, 38(1), 143; *J. Org. Chem.* 1975, 40(23), 3384. For example, as shown in FIG. 8A, chromophores of formula B4 may be prepared by: 1) bromine lithium exchange at the most active alpha position; 2) metal catalyzed cross coupling of functionalized or bulky groups to the fused thiophene; 3) formylation at one of the active alpha positions followed π bridge and/or acceptor coupling; and 4) formylation at the remaining alpha position and π bridge and/or acceptor coupling. Shown in FIG. 8B are exemplary structures, which are not meant to limit the scope of the invention, that may be incorporated in the bridge in the metal catalyzed cross coupling step. One skilled in the art would recognize that there are many possible variants of B4-containing chromophores within the scope of the current invention that could be synthesized by methods like those disclosed in FIG. 8A.

In another aspect, the invention provides chromophores comprising ring locked bithiophene π bridges according to the formula B5:

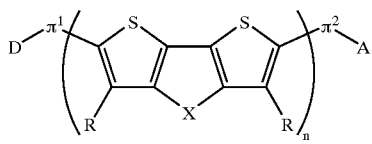

B5 wherein, independently at each occurrence, $\pi^1$ is absent or a bridge that provides electronic conjugation between D and the remainder of the molecule; $\pi^2$ is absent or a bridge that provides electronic conjugation between A and the remainder of the molecule; D is an electron donating group having low electron affinity relative to the electron affinity of A; A is an electron accepting group having high electron affinity relative to the electron affinity of D; X is O, S, Se or $CR_2$; R is hydrogen, halogen, alkyl, aryl, of heteroalkyl; n=1–4; and any one of $\pi^1$, $\pi^2$, D, or A can be further independently substituted with one or more halogen, alkyl, aryl, or heteroalkyl.

Figure 9A:
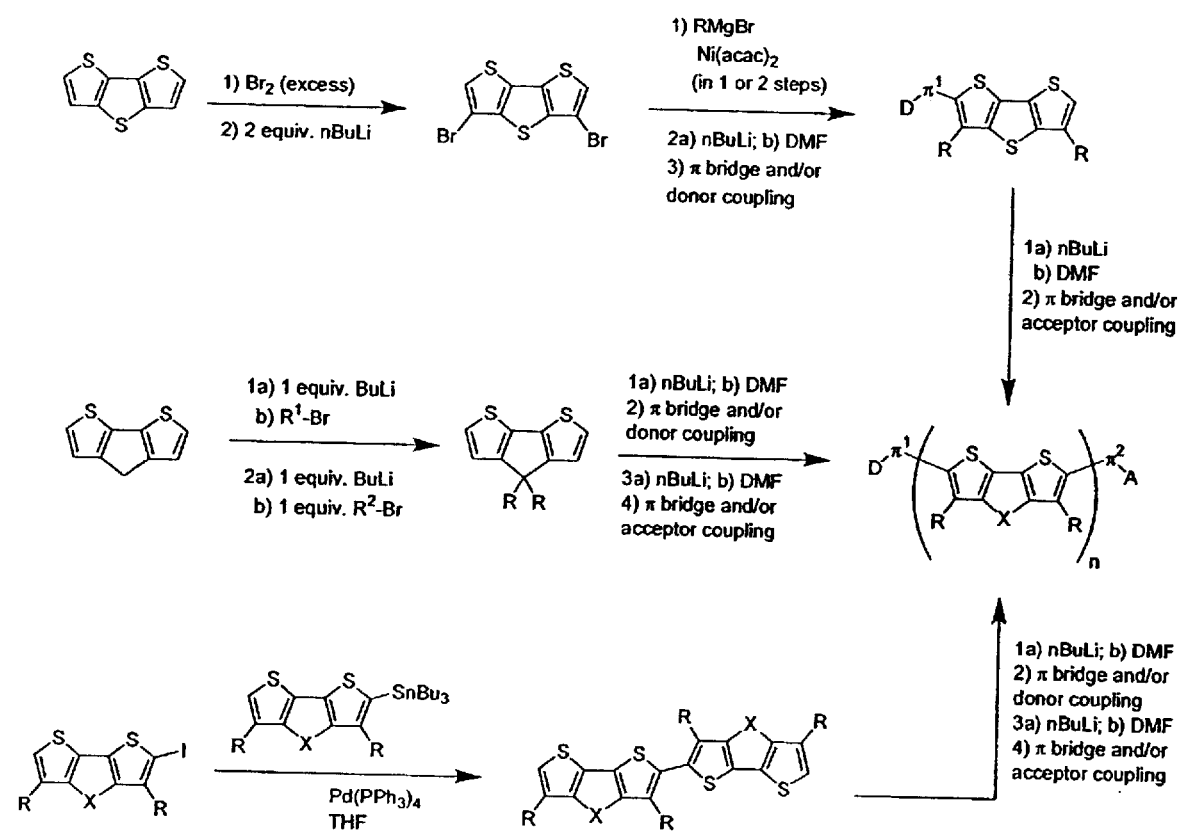
Figure 9B:
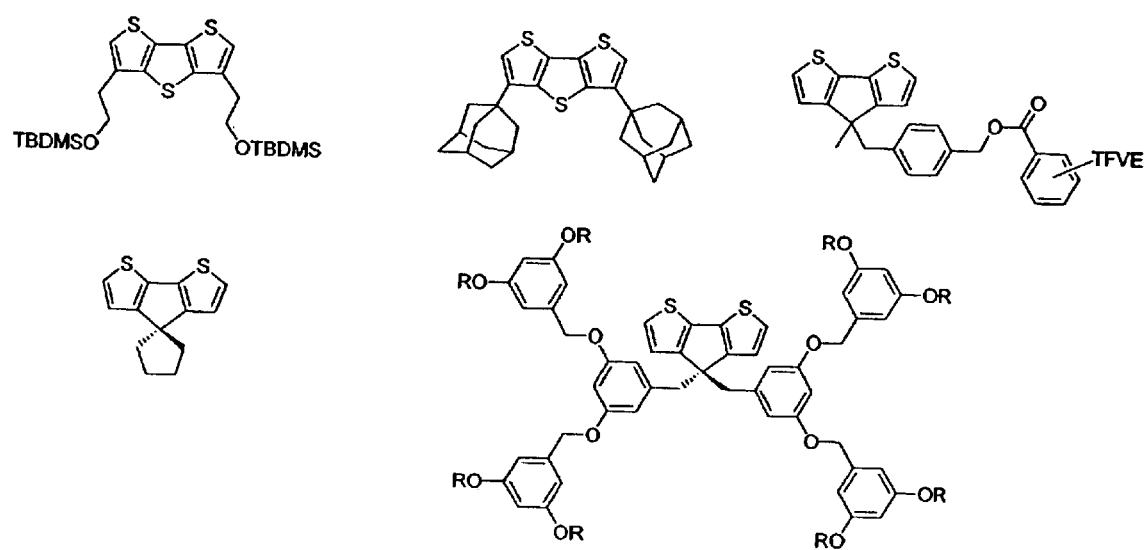

Chromophores according to formula B5 may be prepared using reactions that are known to those skilled in the art, see *J. Chem. Soc. Perkins Trans* 2 1992, 5, 765; *J. Org. Chem.* 1971, 36(12), 1645; *J. Mater. Chem.* 1999, 9(9), 2227; *Tet.* 1999, 55, 14985; *Macromolecules* 1994, 27(7), 1938. For example, as shown in FIG. 9A, chromophores of formula B5 may be prepared by: 1) (for X=O, S, or Se and n=1) bromination of the bithiophene followed bromine-lithium exchange at the most active alpha positions; 2) metal catalyzed cross coupling of selected alkyl groups, formylation, and π bridge and/or donor coupling; 3) formylation and π bridge and/or acceptor coupling; 4) (for X=$CR_2$ and n=1) alkylation of the dithienyl cyclopentadiene; 5) formylation, π bridge and/or donor coupling, formylation, and π bridge and/or acceptor coupling; 6) (for X=O, S, Se, or $CR_2$ and n=2–4) Stille cross coupling of an iodo and a trialkyltin reagent (both being prepared by the methods shown in FIG. 7A from appropriate intermediates in FIG. 9A); and formylation, π bridge and/or donor coupling, formylation, and π bridge and/or acceptor coupling. Shown in FIG. 9B are exemplary structures, which are not meant to limit the scope of the invention, that may be incorporated in the bridge in the metal catalyzed cross coupling step or alkylation step. One skilled in the art would recognize that there are many possible variants of B5-containing chromophores within the scope of the current invention that could be synthesized by methods like those disclosed in FIG. 9A.

In another aspect, the invention provides chromophores comprising ring locked heterocyclic π bridges according to the formula B6:

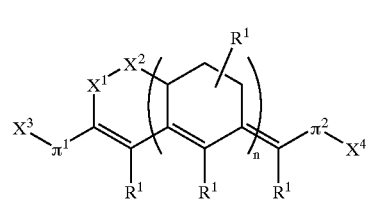

B6 wherein, independently at each occurrence, $\pi^1$ is absent or a bridge that provides electronic conjugation between $X^3$ and the remainder of the molecule; $\pi^2$ is absent or a bridge that provides electronic conjugation between $X^4$ and the remainder of the molecule; either $X^3$ is D and $X^4$ is A or $X^3$ is A and $X^4$ is D; D is an electron donating group having low electron affinity relative to the electron affinity of A; A is an electron accepting group having high electron affinity relative to the electron affinity of D; $X^1$ is O, S, Se, a single bond, or $CR_2$; $X^2$ is $CR_2$ or, when $X^1$ is O, S, Se, or $CR_2$, a single bond; R is alkyl, aryl, or heteroalkyl; $R^1$ is independently at each occurrence hydrogen, alkyl, aryl, or heteroalkyl; n=1–4; and any one of $\pi^1$, $\pi^2$, $X^3$, or $X^4$ can be further independently substituted with one or more halogen, alkyl, aryl, or heteroalkyl.

Figure 10A:
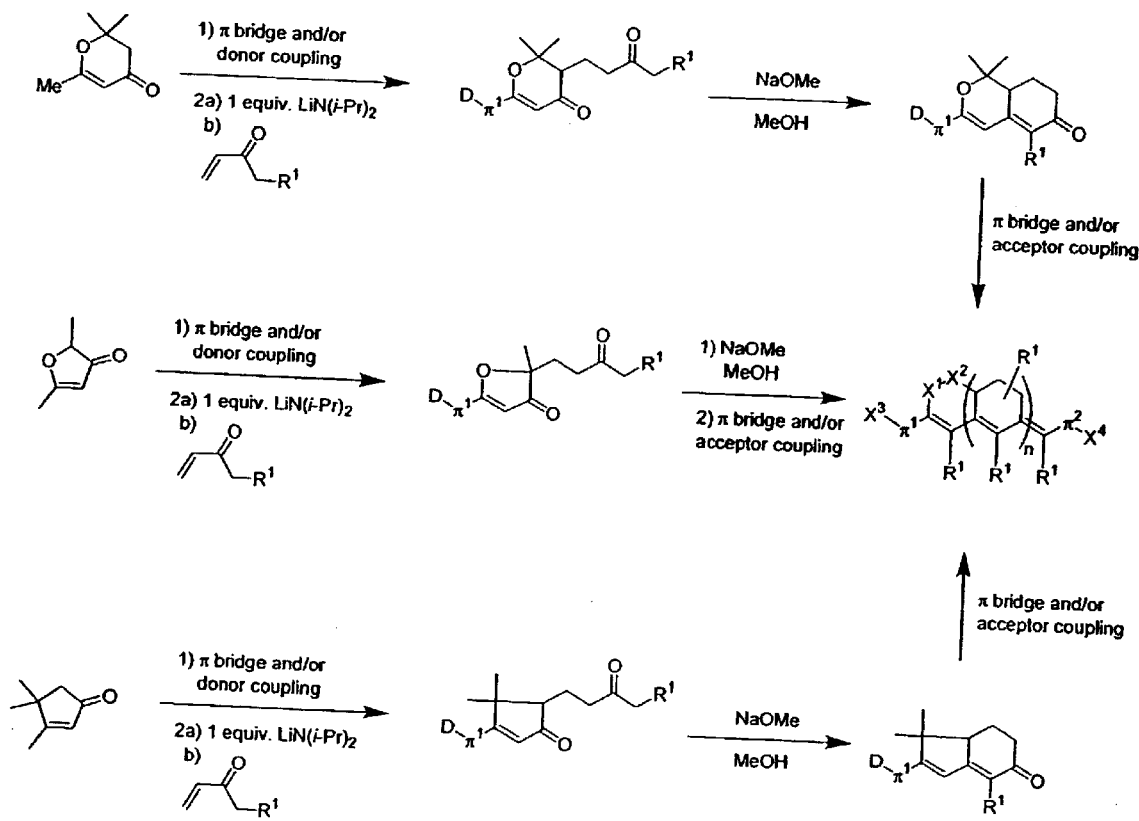
Figure 10B:
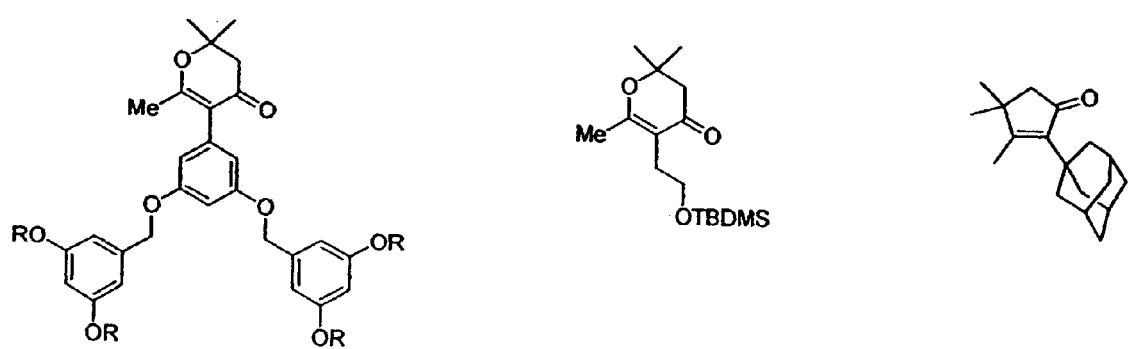

Chromophores according to formula B6 may be prepared using reactions that are known to those skilled in the art, see *Syn. Comm.* 1988, 18(9), 949; *Helv. Chim. Acta.* 1991, 74(1), 27; *Synlett* 1995, 503; *Tet.* 1976, 32, 3; *Syn.* 1976, 177; *Tet. Lett.* 1993, 34(47), 7641; *J. Chem. Soc. Perkins Trans* 1 1998, 1(6), 1139; *Chem. Lett.* 1987, 1007. For example, chromophores of formula B6 may be prepared as shown in FIG. 10A by: 1) formation of the lithium enolate followed by Michael addition to a selected ketone; 2) base induced annulation condensation; 3) π bridge and/or donor coupling; and 4) π bridge and/or acceptor coupling. Shown in FIG. 10B are exemplary structures, which are not meant to limit the scope of the invention, that may be incorporated in the bridge. One skilled in the art would recognize that there are many possible variants of B6-containing chromophore structures within the scope of the current invention that could be synthesized by methods like those disclosed in FIG. 10A.

In another aspect, the invention provides chromophores comprising sterically congested π bridges according to the formula B7:

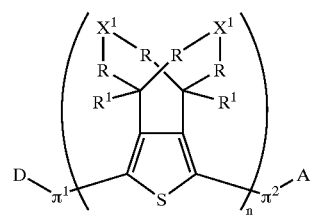

B7 wherein, independently at each occurrence, $\pi^1$ is absent or a bridge that provides electronic conjugation between D and the remainder of the molecule; $\pi^2$ is absent or a bridge that provides electronic conjugation between A and the remainder of the molecule; D is an electron donating group having low electron affinity relative to the electron affinity of A; A is an electron accepting group having high electron affinity relative to the electron affinity of D; $X^1$ is an alkyl linker, an aryl linker, a heteroalkyl linker, or is absent; R is alkyl, aryl, heteroalkyl; the identity of $R^1$ depends on the identity of $X^1$ such that (a) if $X^1$ is an alkyl linker, an aryl linker or a heteroalkyl linker then $R^1$ is hydrogen, alkyl, aryl or heteroalkyl, but (b) if $X^1$ is absent then $R^1$ is alkyl, aryl or heteroalkyl; n=1–4; and any one of $\pi^1$, $\pi^2$, D, or A can be further independently substituted with one or more halogen, alkyl, aryl, or heteroalkyl.

Figure 11A:
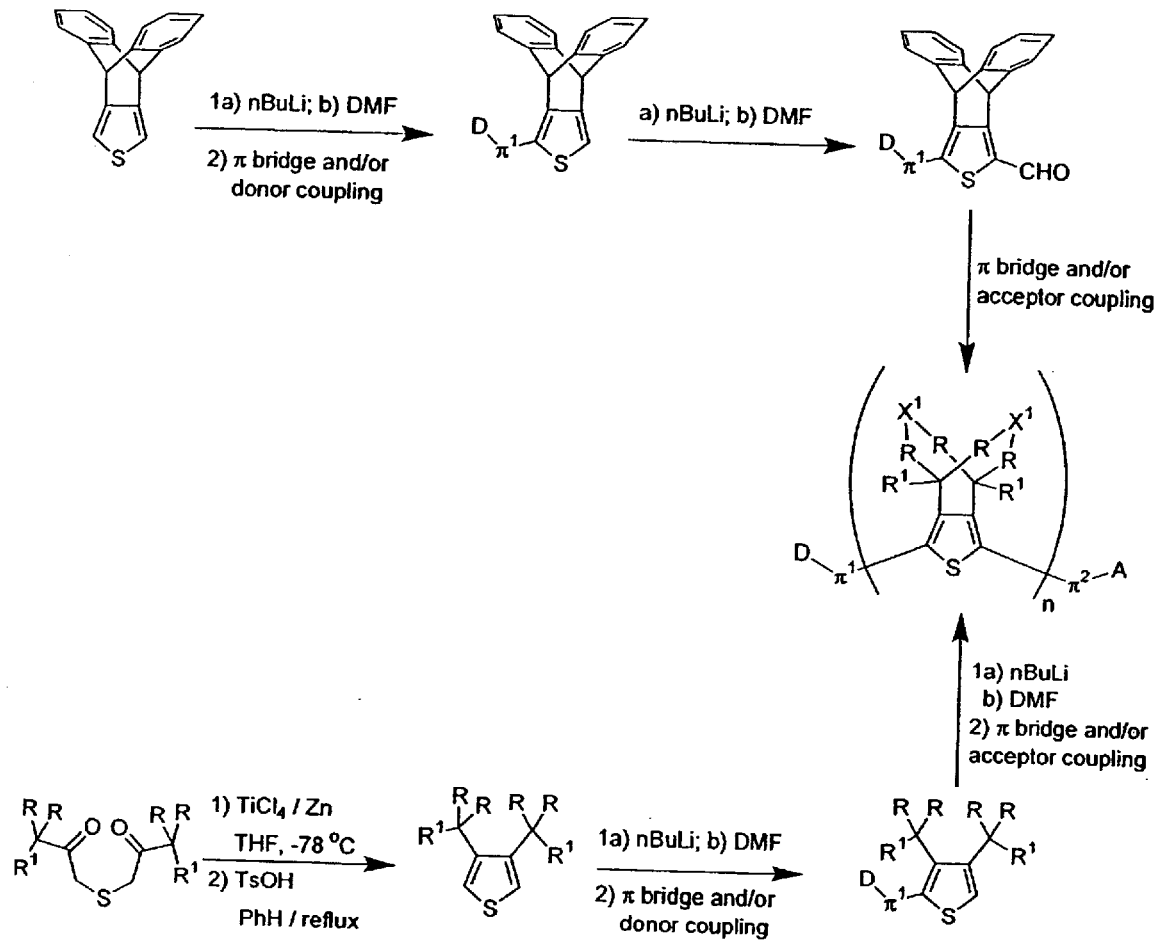
Figure 11B:
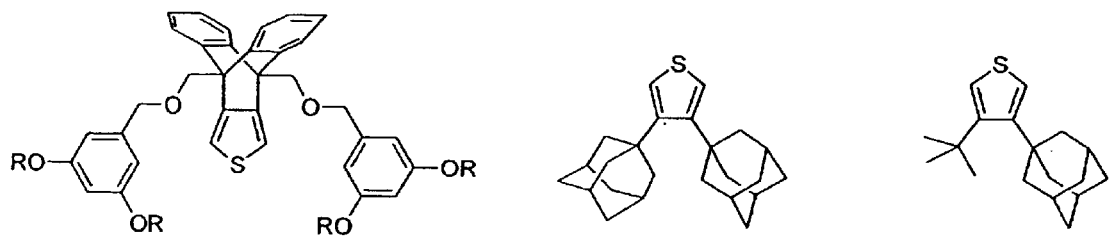

Chromophores according to formula B6 may be prepared using reactions that are known to those skilled in the art, see *J. Org. Chem.* 1997, 62(7), 1940; *Macromolecules* 2000, 33(1), 4069; *J. Org. Chem.* 1998, 63(15), 4912. For example, chromophores of formula B6 may be prepared by method shown in FIG. 11A, by: 1) (for $X^1$=a linker) formylation and π bridge and/or donor coupling; 2) formylation; 3) π bridge and/or acceptor coupling; 4) (for $X^1$=nothing) McMurry-like intramolecular coupling of di(β-keto) sulfides followed by acid catalyzed double elimination of water; 5) formylation and π bridge and/or donor coupling; and 6) formylation and π bridge and/or acceptor coupling. Shown in FIG. 11B are exemplary structures, which are not meant to limit the scope of the invention, that may be incorporated in the bridge. One skilled in the art would recognize that there are many possible variants of B7-containing chromophore structures within the scope of the current invention that could be synthesized by methods like those disclosed in FIG. 11A.

Thus, various embodiments of the present invention are:

A second chromophore comprising a 5- or 6-membered ring-locked π bridge containing no reactive allylic hydrogens according to the formula B1:

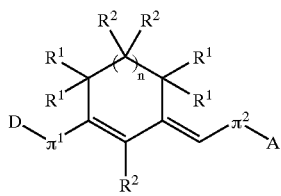

B1 wherein $\pi^1$ and $\pi^2$ are independently optional; $R^1$ is independently at each occurrence halogen, alkyl, aryl, or heteroalkyl; $R^2$ is independently at each occurrence hydrogen, halogen, alkyl, aryl, or heteroalkyl; and n=0 or 1.

A third chromophore containing 5- or 6-membered ring-locked heterocyclic π bridges according to the general formula B2:

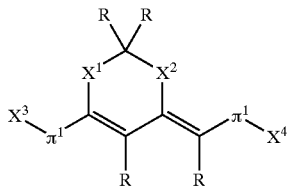

B2 wherein $\pi^1$ and $\pi^2$ are independently optional; either $X^3$ is D and $X^4$ is A or $X^3$ is A and $X^4$ is D; $X^1$ is O or S; $X^2$ is O, S, a single bond, or $CR_2$; R is independently at each occurrence hydrogen, alkyl, aryl, or heteroalkyl; and $X^3$, $X^4$, $\pi^1$, and $\pi^2$ can be further substituted with halogen, alkyl, aryl, and heteroalkyl.

A fourth chromophore comprising thiophene π bridges containing no allylic protons according to the formula B3:

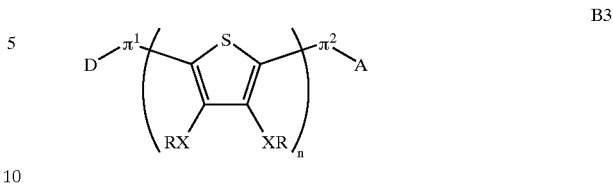

B3 wherein $\pi^1$ and $\pi^2$ are independently optional; X is independently at each occurrence O or S; R is independently at each occurrence alkyl, aryl, of heteroalkyl; n=1–4; and any one of $\pi^1$, $\pi^2$, D, or A can be further independently substituted with halogen, alkyl, aryl, or heteroalkyl.

A fifth chromophore comprising fused thiophene π bridges according to the formula B4:

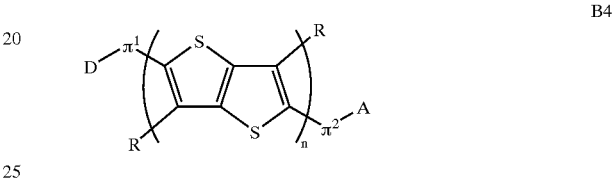

B4 wherein $\pi^1$ and $\pi^2$ are independently optional; R is independently at each occurrence halogen, alkyl, aryl, or heteroalkyl; n=1–4; and any one of, $\pi^1$, $\pi^2$, D, or A can be further independently substituted with one or more halogen, alkyl, aryl, or heteroalkyl.

A sixth chromophore comprising locked bithiophene π bridges according to the formula B5:

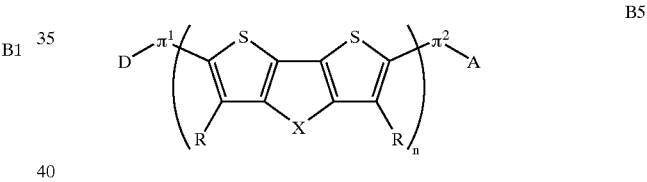

B5 wherein $\pi^1$ and $\pi^2$ are independently optional; X is O, S, Se or $CR_2$; R is independently at each occurrence hydrogen, halogen, alkyl, aryl, of heteroalkyl; n=1–4; and any one of $\pi^1$, $\pi^2$, D, or A can be further independently substituted with one or more halogen, alkyl, aryl, or heteroalkyl.

A seventh chromophore comprising fused heterocyclic π-bridges according to the formula B6:

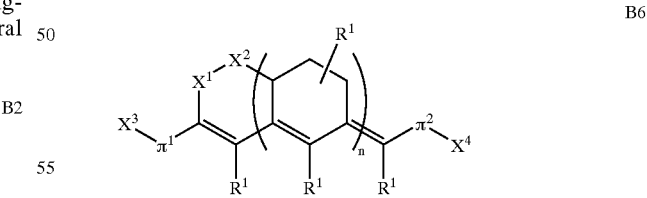

B6 wherein $\pi^1$ and $\pi^2$ are independently optional; $X^1$ is O, S, Se, a single bond, or $CR_2$; $X^2$ is $CR_2$ or, when $X^1$ is O, S, Se, or $CR_2$, a single bond; either $X^3$ is D when $X^4$ is A or $X^3$ is A when $X^4$ is D; R is independently at each occurrence alkyl, aryl, or heteroalkyl; $R^1$ is independently at each occurrence hydrogen, alkyl, aryl, or heteroalkyl; n=1–4; and any one of $\pi^1$, $\pi^2$, $X^3$, or $X^4$ can be further independently substituted with one or more halogen, alkyl, aryl, or heteroalkyl.

An eighth chromophore comprising a sterically congested π-bridge according to the formula B7:

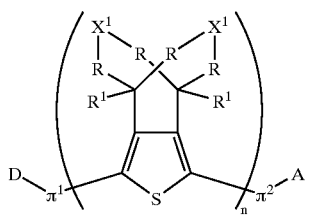

wherein $\pi^1$ and $\pi^2$ are independently optional; $X^1$ is independently at each occurrence an alkyl linker, an aryl linker, a heteroalkyl linker, or nothing; R is independently at each occurrence alkyl, aryl, heteroalkyl; $R^1$ is independently at each occurrence, when $X^1$=nothing, alkyl, aryl, or heteroalkyl with the additional proviso that $R^1$ can be hydrogen if $X^1$=an alkyl, aryl, or heteroalkyl linker; n=1–4; and any one of $\pi^1$, $\pi^2$, D, or A can be further independently substituted with one or more halogen, alkyl, aryl, or heteroalkyl.

In another aspect the invention provides chromophores comprising locked heterocyclic ring vinylidene acceptors according to formula A1:

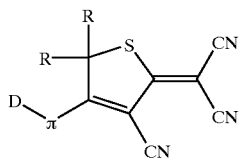

wherein, independently at each occurrence, π is absent or a bridge that provides electronic conjugation between D and the remainder of the molecule; D is an electron donating group having low electron affinity relative to the remainder of the molecule; R is alkyl, aryl, or heteroalkyl; and π or D can be further independently substituted with one or more halogen, alkyl, aryl, or heteroalkyl. Additionally, to sulfur in the ring can be oxidized to SO or $SO_2$.

Figure 12A:
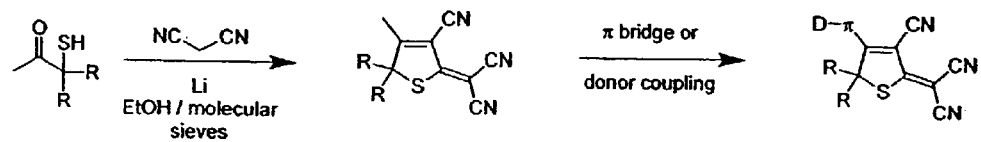
Figure 12B:
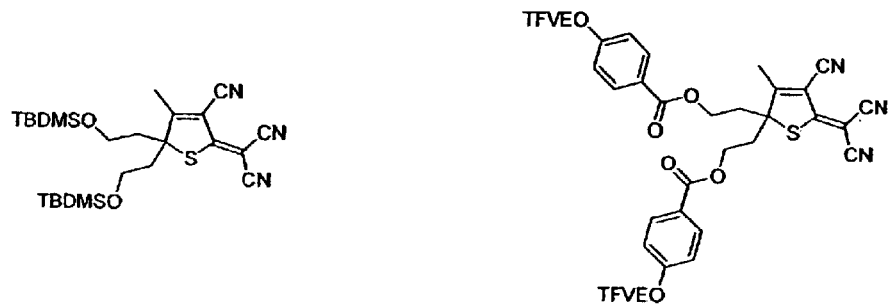

Chromophores according to formula A1 may be prepared using reactions that are known to those skilled in the art, see *Inorg. Chem.* 1998, 37, 5722. For example, a chromophore of formula A1 may be prepared as illustrated in FIG. 12A by: 1) condensation of 2 equivalents of malononitrile with an alpha thioketone; and 2) π bridge and/or donor coupling. Shown in FIG. 12B are exemplary structures, which are not meant to limit the scope of the invention, that are additional embodiments of the current invention. One skilled in the art would recognize that there are many possible variants of A1 chromophores within the scope of the current invention that could be synthesized by methods like those disclosed in FIG. 12A.

Thus, in further embodiments, the present invention provides:

A ninth chromophore comprising a locked heterocyclic ring vinylidene acceptors according to formula A1:

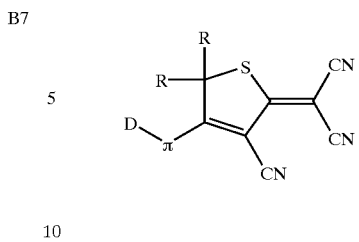

wherein, independently at each occurrence, π is absent or a bridge that provides electronic conjugation between D and the remainder of the molecule; D is an electron donating group having low electron affinity relative to the remainder of the molecule; R is alkyl, aryl, or heteroalkyl; and π or D can be further independently substituted with one or more halogen, alkyl, aryl, or heteroalkyl.

Various additional aspects according to the present invention are chromophores having a D-π-A connectivity; additionally, in other aspects according to the present invention are chromophores with multiple donors and acceptors wherein the connectivity can be represented by D-π($-\pi^1$-A)$_2$, (D-$\pi^1$-)$_2$π-A, and (D-$\pi^1$-)$_2$π($-\pi^2$-A)$_2$.

Another aspect according to the present invention is chromophores represented by the D-π($-\pi^1$-A)$_n$ connectivity according to the formula MAC:

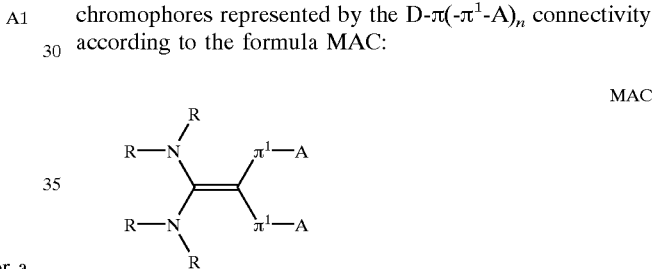

wherein, independently at each occurrence, $\pi^1$ is absent or a bridge that provides electronic conjugation between A and the remainder of the molecule; A is an electron accepting group having high electron affinity relative to the electron affinity of the remainder of the molecule; R is alkyl, aryl, or heteroalkyl; and π and/or A may be further substituted with halogen, alkyl, aryl, or heteroalkyl.

Figure 1A:
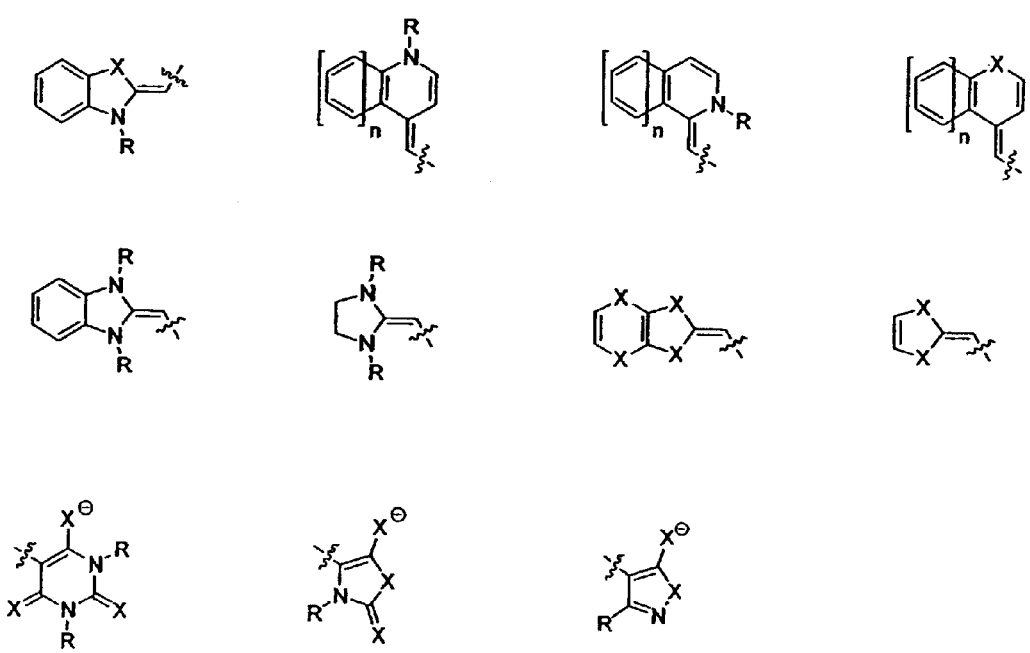
FIGS. 1A and 1B illustrate exemplary donor moieties (D) that may incorporated into a chromophore where, in FIG. 1A independently at each occurrence, R is alkyl, aryl, or heteroaryl, X is O, S, Se, or Te, and n is 1 or 2; and in FIG. 1B independently at each occurrence, R is alkyl, aryl or heteroalkyl; $R^1$ is hydrogen, alkyl, aryl or heteroalkyl; Y is O, S or Se; m is 2, 3 or 4; p is 0, 1 or 2; and q is 0 or 1; wherein each of alkyl, aryl and heteroaryl is defined herein.
Figure 1B:
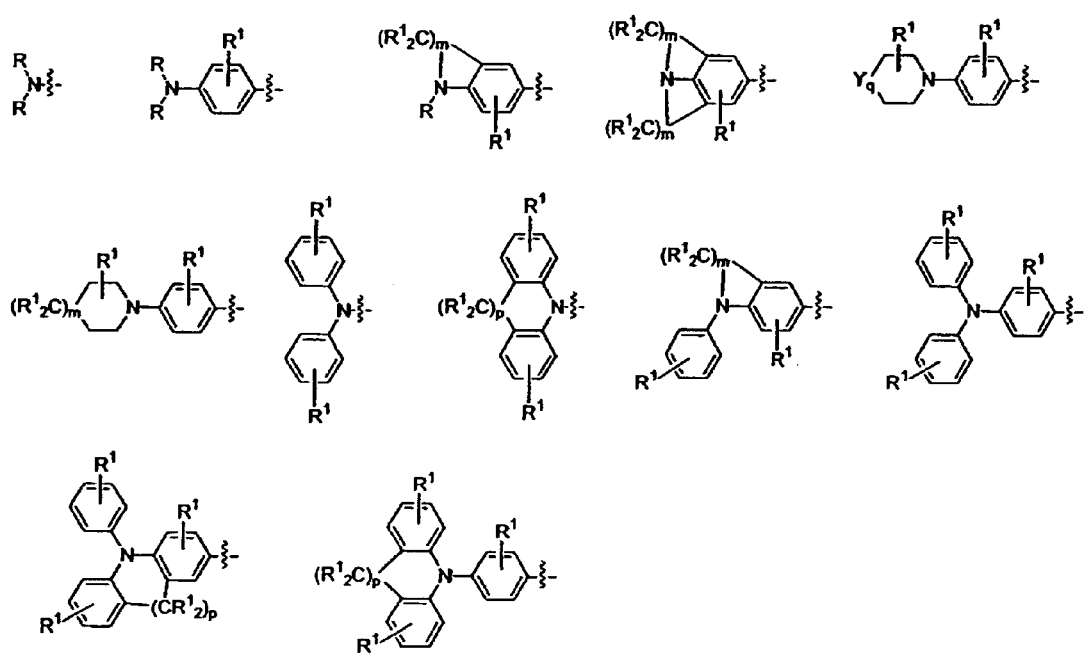
Figure 13A:
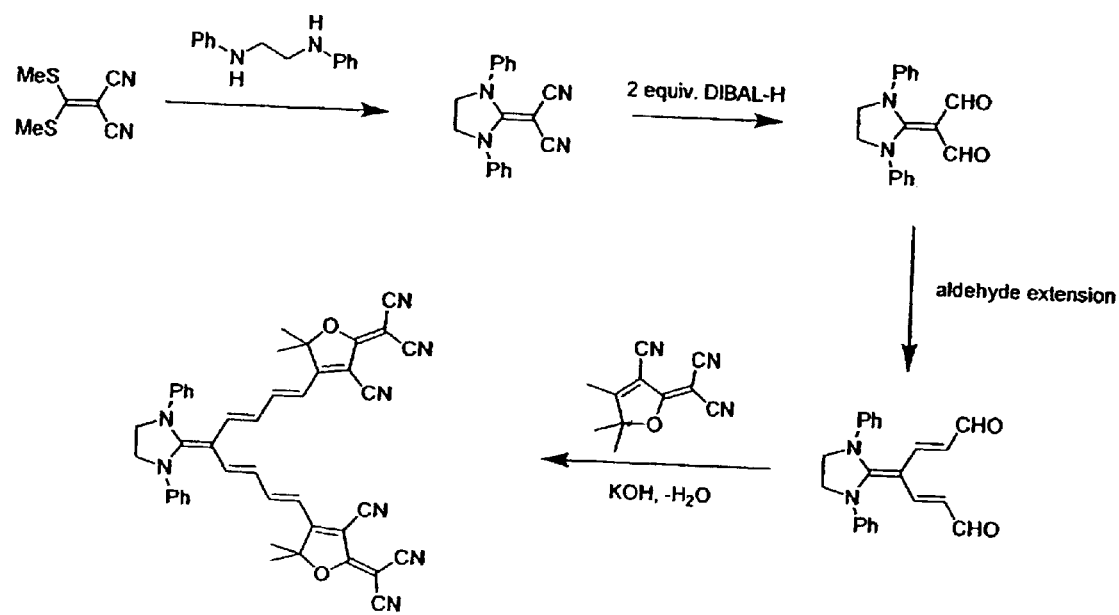
Figure 13B:
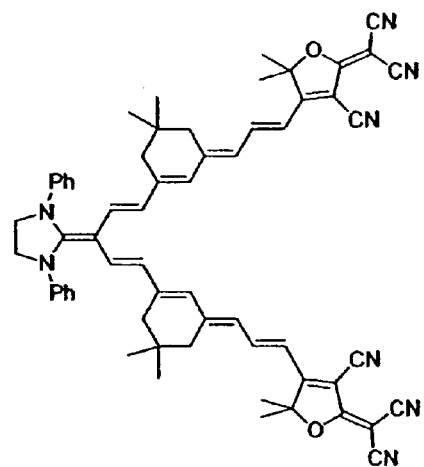
Figure 13B:
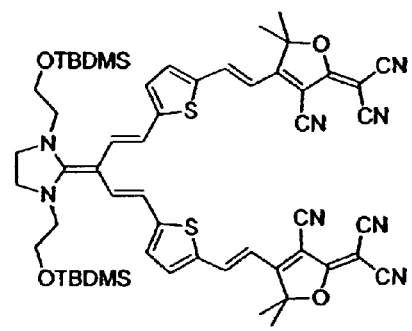
Figure 13B:
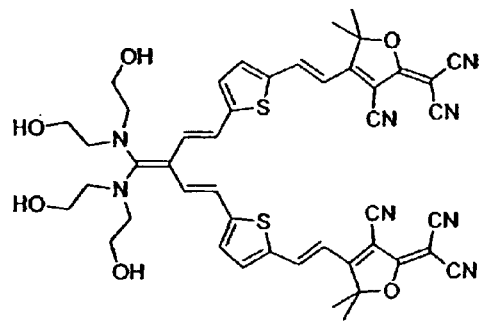
Figure 13B:
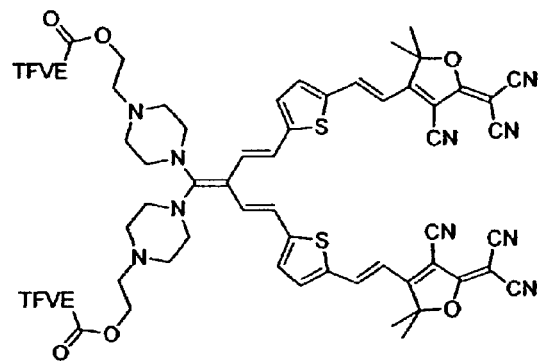

Chromophores according to formula MAC may be synthesized using reactions like those shown in FIG. 13A, by: 1) double nucleophilic displacement of methyl sulfide with amines, which is also shown in FIG. 1A; 2) double reduction of the corresponding dinitrile to the dialdehyde; 3) optional aldehyde extension; and 4) coupling of a selected acceptor. Shown in FIG. 13B are exemplary structures, which are not meant to limit the scope of the invention, that are additional embodiments of the current invention. One skilled in the art would recognize that there are many possible variants of MAC chromophores within the scope of the current invention that could be synthesized by methods like those disclosed in FIG. 13A.

Another aspect according to the present invention is chromophores of (D-$\pi^1$-)$_n$π-A connectivity according to the formula MDC:

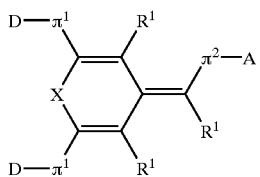

MDC wherein, independently at each occurrence, $\pi^1$ is absent or a bridge that provides electronic conjugation between D and the remainder of the molecule; $\pi^2$ is absent or a bridge that provides electronic conjugation between A and the remainder of the molecule; D is an electron donating group having low electron affinity relative to the electron affinity of A; A is an electron accepting group having high electron affinity relative to the electron affinity of D; $R^1$ is hydrogen, halogen, alkyl, aryl, or heteroalkyl; X is a single bond, O, S, Se, $NR^2$ wherein $R^2$ is independently at each occurrence alkyl, aryl, or heteroalkyl, or $C(R^3)_2$ wherein $R^3$ is independently at each occurrence hydrogen, alkyl, aryl, or heteroalkyl; and any of $\pi$, $\pi^1$, D, or A independently at each occurrence can be further substituted with halogen, alkyl, aryl, or heteroalkyl.

Figure 14A:
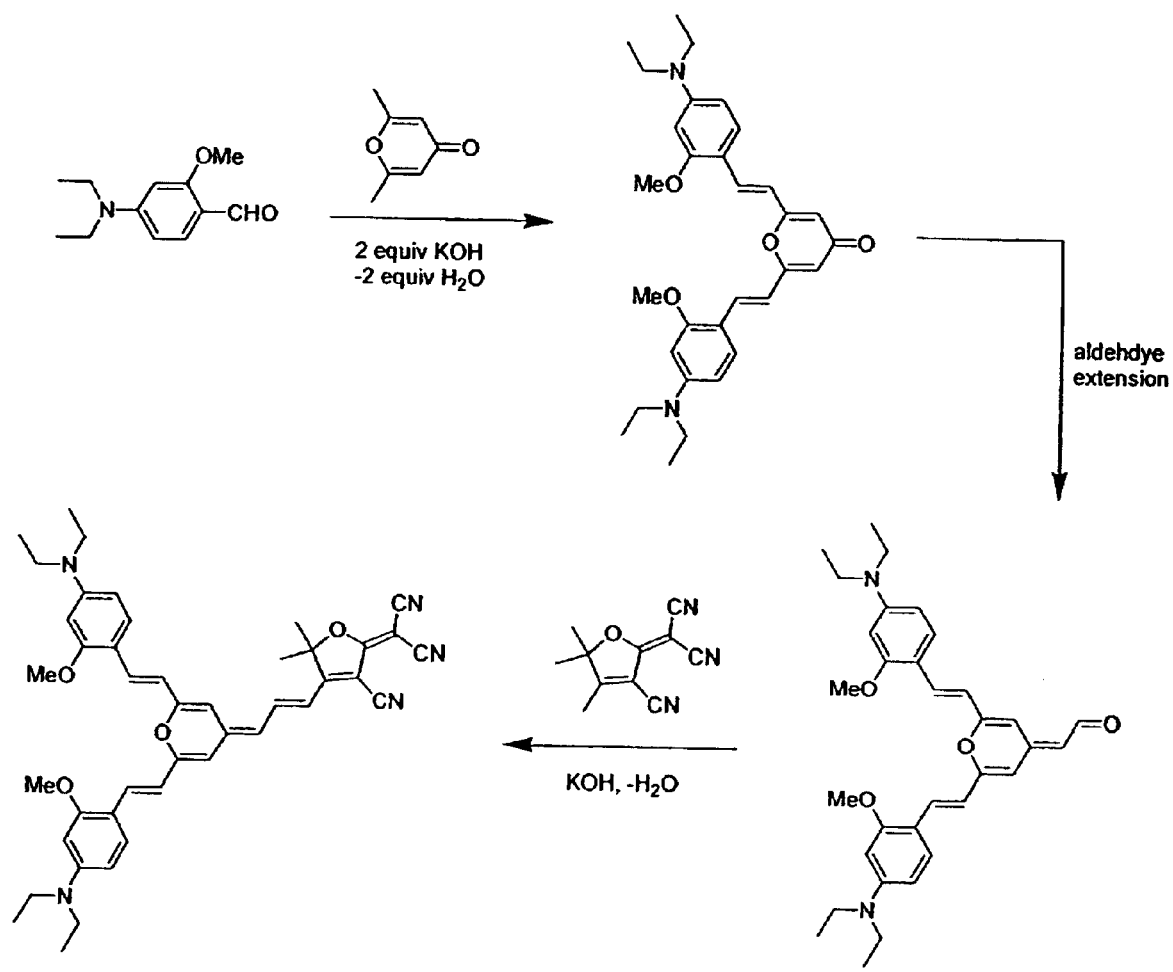
Figure 14B:
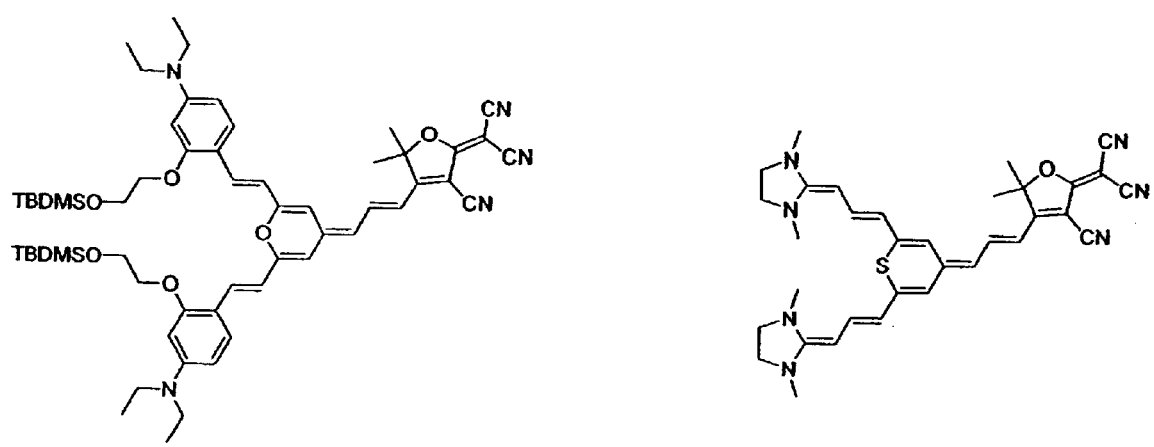

Chromophores according to formula MDC may be synthesized using reactions like those shown in FIG. 14A, by, for instance: 1) double condensation of a selected aldehyde with doubly acidic π bridges; 2) optional aldehyde extension; and 3) coupling of a selected acceptor. Shown in FIG. 14B are exemplary structures, which are not meant to limit the scope of the invention, that are additional embodiments of the current invention. One skilled in the art would recognize that there are many possible variants of MDC chromophores within the scope of the current invention that could be synthesized by methods like those disclosed in FIG. 14A.

Another aspect according to the present invention is chromophores of $(D-\pi^1-)_n\pi(-\pi^2-A)_m$ connectivity according to the formula MDAC:

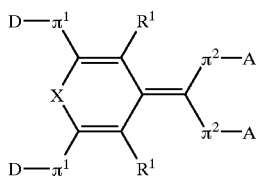

MDAC wherein, independently at each occurrence, $\pi^1$ is absent or a bridge that provides electronic conjugation between D and the remainder of the molecule; $\pi^2$ is absent or a bridge that provides electronic conjugation between A and the remainder of the molecule; D is an electron donating group having low electron affinity relative to the electron affinity of A; A is an electron accepting group having high electron affinity relative to the electron affinity of D; $R^1$ is hydrogen, halogen, alkyl, aryl, or heteroalkyl; X is a single bond, O, S, Se, $NR^2$ wherein $R^2$ is independently at each occurrence alkyl, aryl, or heteroalkyl, or $C(R^3)_2$ wherein $R^3$ is independently at each occurrence hydrogen, alkyl, aryl, or heteroalkyl; and any of $\pi^1$, $\pi^2$, D, or A independently at each occurrence can be further substituted with halogen, alkyl, aryl, or heteroalkyl.

Figure 15A:
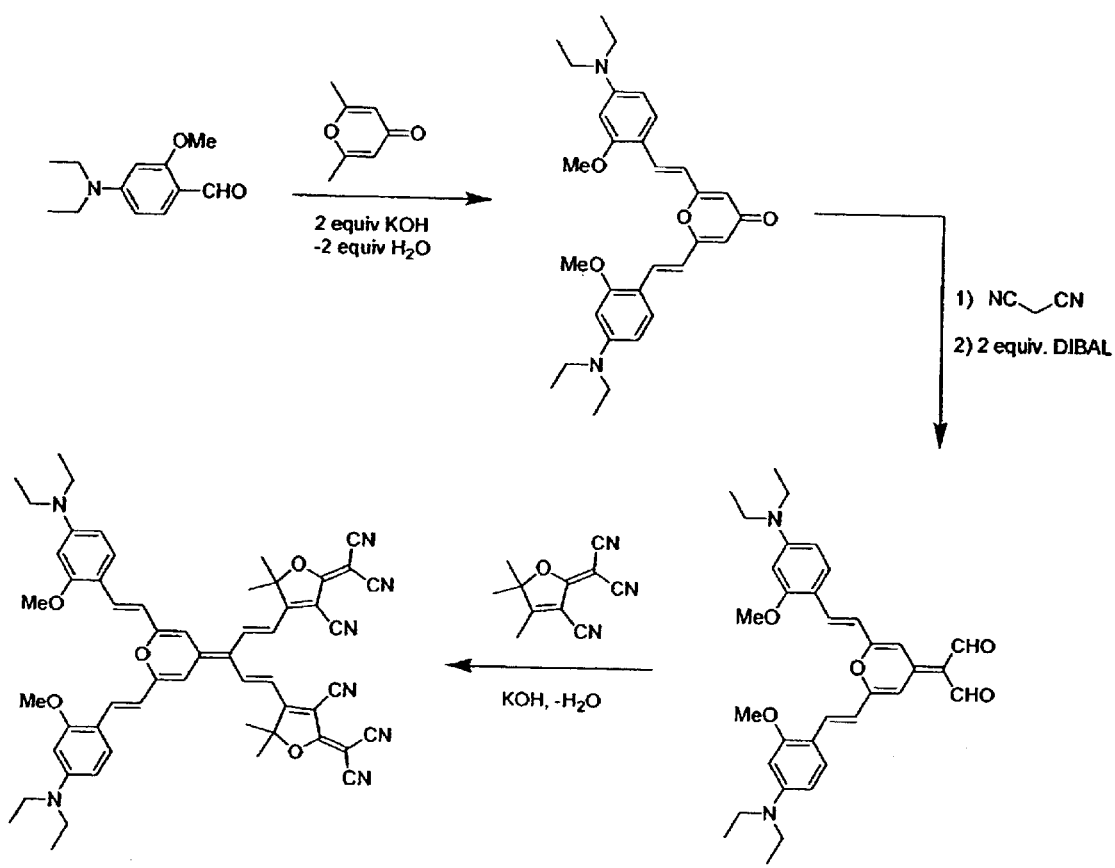
Figure 15B:
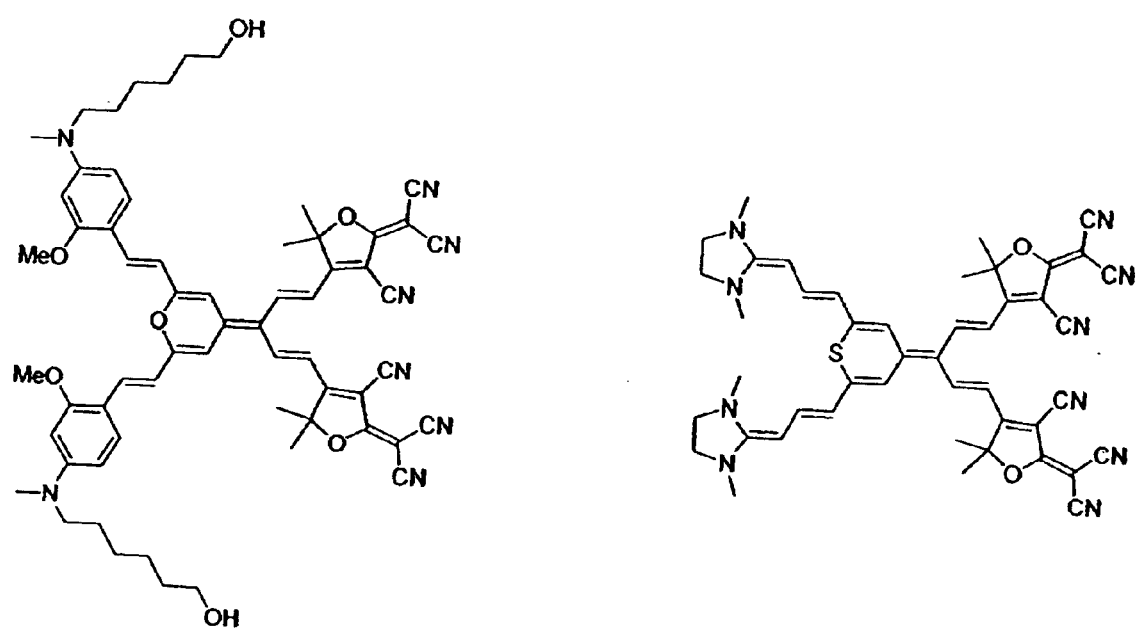

Chromophores according to formula MDAC may be synthesized using reactions like those shown, for instance, in FIG. 15A by: 1) double condensation of a selected aldehyde with doubly acidic π bridges; 2) Knoevenagel condensation of malononitrile and double reduction to the dialdehyde; and 3) coupling of a selected acceptor. Shown in FIG. 15B are exemplary structures, which are not meant to limit the scope of the invention, that are additional embodiments of the current invention. One skilled in the art would recognize that there are many possible variants of MDC chromophores within the scope of the current invention that may be synthesized by methods like those disclosed in FIG. 15A.

Thus, various embodiments according to the present invention are:

A tenth chromophore of $D-\pi(-\pi^1-A)_n$ connectivity according to the formula MAC:

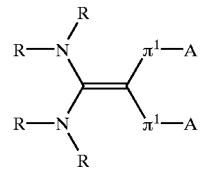

MAC wherein $\pi^1$ is independently at each occurrence optional, R is independently at each occurrence alkyl, aryl, or heteroalkyl; and π independently at each occurrence or A independently at each occurrence can be further substituted with halogen, alkyl, aryl, or heteroalkyl.

An eleventh chromophore of $(D-\pi^1-)_n\pi-A$ connectivity according to the formula MDC:

MDC wherein π and $\pi^1$ are independently at each occurrence optional, $R^1$ is independently at each occurrence hydrogen, halogen, alkyl, aryl, or heteroalkyl; X is a single bond, O, S, Se, $NR^2$ wherein $R^2$ is independently at each occurrence alkyl aryl, or heteroalkyl, or $C(R^3)_2$ wherein $R^3$ is independently at each occurrence hydrogen, alkyl, aryl, or heteroalkyl; and any of π, $\pi^1$, D, or A independently at each occurrence can be further substituted with halogen, alkyl, aryl, or heteroalkyl.

A twelfth chromophore of $(D-\pi^1-)_n\pi(-\pi^2-A)_m$ connectivity according to the formula MDAC:

MDAC wherein $\pi^1$ and $\pi^2$ are independently at each occurrence optional, $R^1$ is independently at each occurrence hydrogen, halogen, alkyl, aryl, or heteroalkyl; X is a single bond, O, S, Se, $NR^2$ wherein $R^2$ is independently at each occurrence alkyl, aryl, or heteroalkyl, or $C(R^3)_2$ wherein $R^3$ is independently at each occurrence hydrogen, alkyl, aryl, or heteroalkyl; and any of $\pi^1$, $\pi^2$, D, or A independently at each occurrence can be further substituted with halogen, alkyl, aryl, or heteroalkyl.

Those skilled in the art will recognize that there are many variations of the chromophores according to the present invention that may be processed into active EO materials through a method comprising general steps known to those skilled in the art, see U.S. Pat. Nos. 5,834,575; 5,736,592; 5,718,845; 5,688,906; 5,679,763; 5,410,630; *Macromolecules* 1996, 29(7), 2365; *Macromolecules* 2001, 34, 235; *Chem. Phys.* 1999, 245, 487; *Chem. Phys.* 1999, 245, 35; *Polymer* 1999, 40(17), 4923: 1) covalently or non-covalently incorporating the chromophore into a polymer matrix; 2) maintaining the polymer matrix at a selected temperature to allow effective chromophore mobility; and 3) applying an electric field sufficient to induce polar alignment of the chromophore in the polymer matrix.

It is further known in the art that crosslinking the polymer matrix improves long-term orientational stability (i.e., polar alignment) of chromophores in the matrix; and long-term orientational stability effectively increases the length of time during which the materials are EO active. The chromophores of the current invention may be incorporated into crosslinkable polymer matrices in any one of three ways: 1) non-covalently in incorporating the chromophore in a crosslinkable polymer; 2) covalently incorporating the chromophore in a polymer, wherein the polymer is independently crosslinkable; and 3) covalently incorporating a reactive chromophore in a polymer, thereby rendering the polymer crosslinkable. Suitable crosslinking processes that are induced by acids, bases, heat, UV light exposure, visible light exposure, and electron beam exposure are all well known to those skilled in the art.

Specific D groups that may be incorporated into a chromophore that also includes any acceptor, p-bridge and/or an additional donor as described above include, without limitation, each of the D groups illustrated in any of the Figures described herein, including D groups of the following structures,

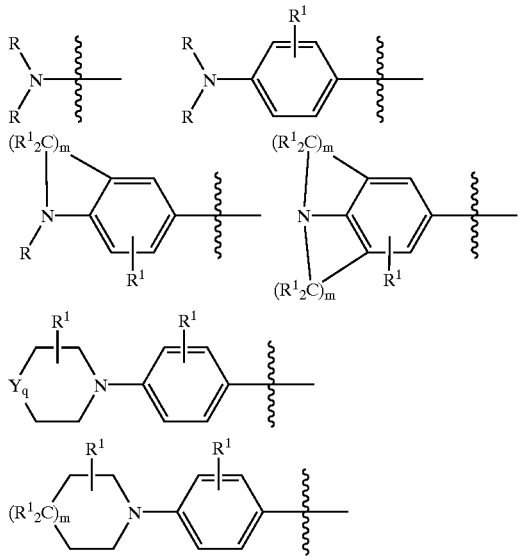

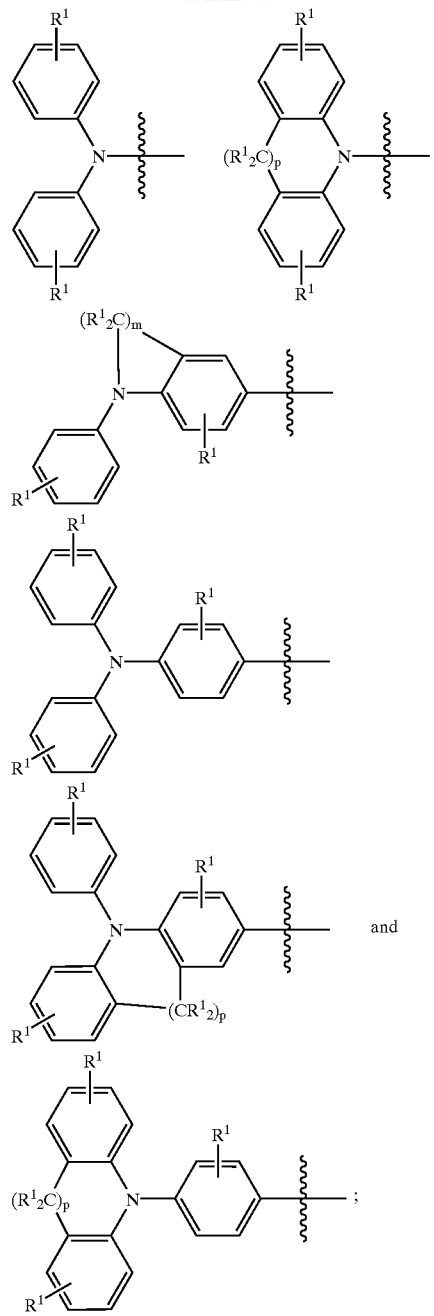

wherein, independently at each occurrence, R is alkyl, aryl or heteroalkyl; $R^1$ is hydrogen, alkyl, aryl or heteroalkyl; Y is O, S or Se; m is 2, 3 or 4; p is 0, 1 or 2; and q is 0 or 1. In one embodiment, R contains 1–12 carbons; $R^1$ is hydrogen or contains 1–12 carbons; Y is O or S; m is 2, 3 or 4; p is 0, 1 or 2; and q is 0 or 1. Some preferred D groups that may be present in a chromophore are of the structures:

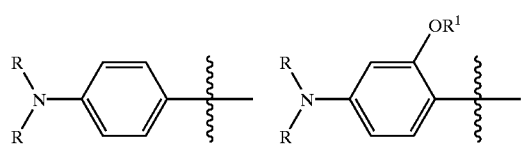

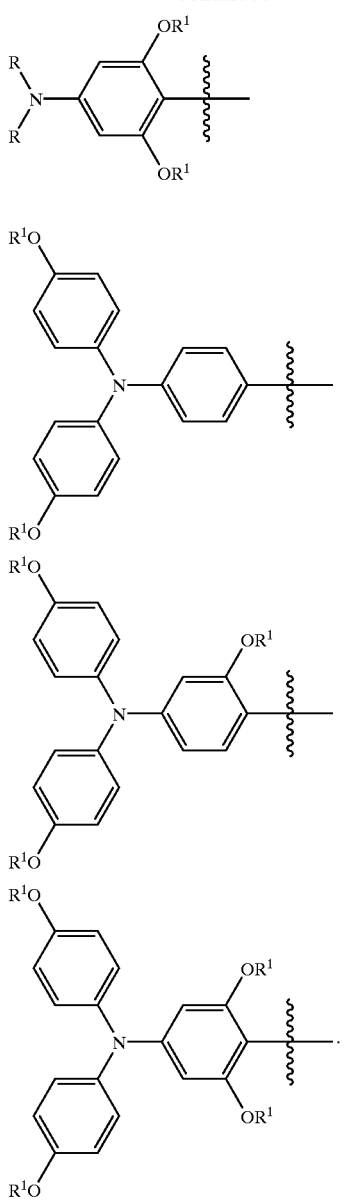

Specific p-bridges that may be incorporated into a chromophore that also includes any donors, acceptors or additional p-bridges as described herein include, without limitation, a p-bridge of the structure

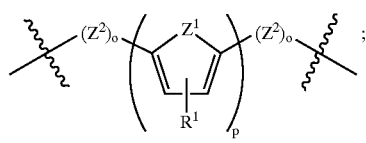

wherein, independently at each occurrence, $Z^1$ is O, S, Se, $NR^1$, $C(R^1)_2$ or $-C(R^1)=C(R^1)-$; p is 0, 1 or 2; o is 0, 1 or 2; o+p is at least 1; $R^1$ is hydrogen, alkyl, aryl or heteroalkyl;

$Z^2$ is

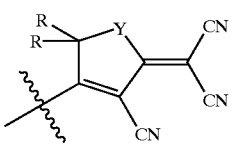

and q is 0 or 1.

Some specific structures for a p-bridge, including $\pi^1$ and $\pi^2$, are:

wherein, independently at each occurrence, $R^1$ is hydrogen, alkyl, aryl or heteroalkyl; $Z^1$ is O, S, Se, $NR^1$, $C(R^1)_2$ or $-C(R^1)=C(R^1)-$; p is 0, 1 or 2; o is 0, 1 or 2; o+p is at least 1; and q is 0 or 1. In one aspect each of $\pi^1$ and $\pi^2$ are $-CH=CH-$.

Specific A groups that may be incorporated into chromophores that also include one or more donors (D) and p-bridges as described herein include each of the A groups illustrated in any of the Figures described herein, including A groups of the following structures -continued

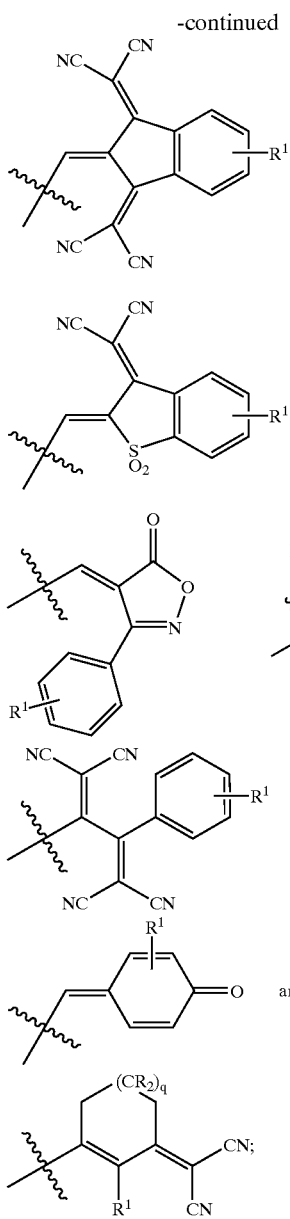

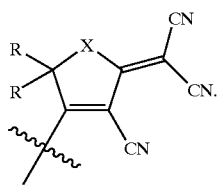

wherein, independently at each occurrence, R is alkyl, aryl or heteroalkyl; $R^1$ is hydrogen, alkyl, aryl or heteroalkyl; Y is O, S or Se; and q is 0 or 1. Optionally, R contains 1–12 carbons; $R^1$ is hydrogen or contains 1–12 carbons; Y is O or S; and q is 0 or 1. A specifically preferred A group is of the formula

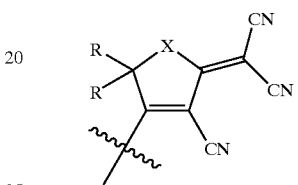

In various aspects a chromophore may specify that R is alkyl, and/or aryl, and/or heteroalkyl, and/or heteroaryl, including each and every combination thereof. Optionally, R is hydrophobic, while alternatively R is hydrophilic. Optionally, an R group is saturated, while alternatively an R group may be unsaturated. The R group may have, in various aspects of the invention, 1–6 carbons, or 7–12 carbons, or 13–22 carbons.

The value of n in a chromophore as described herein may be 1, or 2, or 3, or 4, or each and every combination thereof, e.g., 2 or 3. In one aspect, X in a chromophore is O, while in another aspect X is S.

In one chromophore according to the present invention, $\pi^1$ and $\pi^2$ are

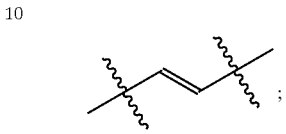

and A is any of the acceptors shown herein, including

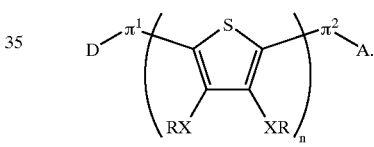

wherein R is independently at each occurrence alkyl, aryl or heteroalkyl.

Chromophore as described herein may have a specified structure where portions of the p-bridge, as well as the donor and acceptor groups, are optionally chosen, e.g., a chromophore of the structure $$D-\pi^1-\underset{RX\ XR}{\underset{|\ \ \ |}{\left(\ \ \ \overset{S}{\underset{}{\bigcirc}}\ \ \ \right)_n}}-\pi^2-A.$$

In this case, the D and A groups may be any of the donor and acceptors groups shown herein, and the p-bridge may be any of the p-bridges shown herein. For instance, D may be selected from the group consisting of

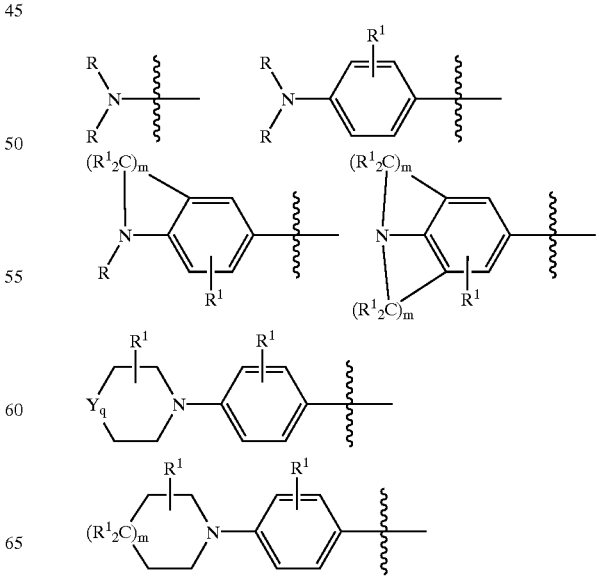

-continued
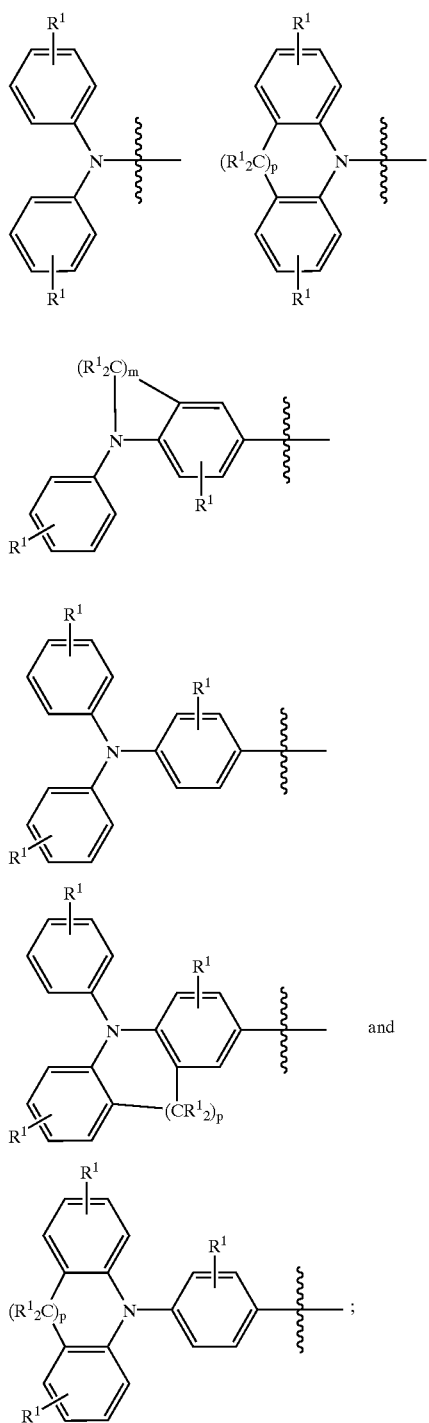
and
$\pi^1$ and $\pi^2$ may be independently
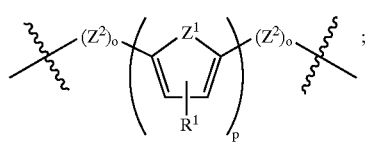
and A may be selected from the group consisting of
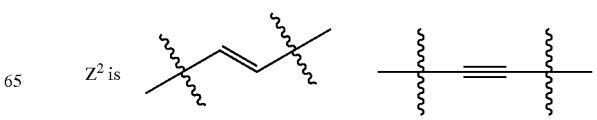
where X is O or S; R is alkyl, aryl or heteroalkyl; n is 1, 2, 3 or 4; $R^1$ is hydrogen, alkyl, aryl or heteroalkyl; Y is O, S or Se; $Z^1$ is O, S, Se, $NR^1$, $C(R^1)_2$ or —$C(R^1)$=$C(R^1)$—;
$Z^2$ is

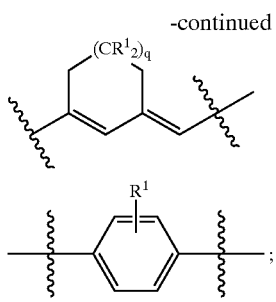

or

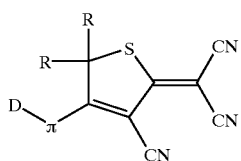

q is 0 or 1; p is 0, 1 or 2; o is 0, 1 or 2; o+p is at least 1; and m is 2, 3 or 4.

In some instances, the present invention describes chromophores as generally containing one or more A, D and/or p-bridges. For example, a chromophore may be described as having a structure

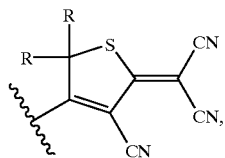

wherein, independently at each occurrence, D is an electron donating group having low electron affinity relative to the electron affinity of

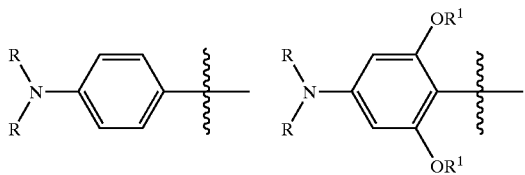

π is absent or a bridge that provides electronic conjugation between D and the double bond adjacent to π; and R is alkyl, aryl, heteroalkyl or heteroaryl. In this case, A, D and/or the p-bridge may be any of the A, D and/or the p-bridges described herein, including described in the Figures. As one example, in a chromophore defined as including D and one or more p-bridges, D may be selected from:

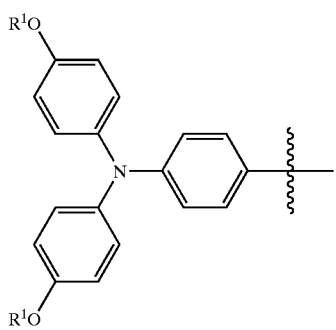

and

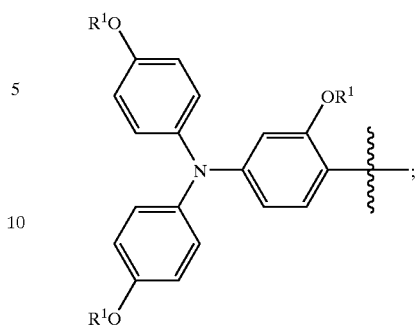

and π may be selected from:

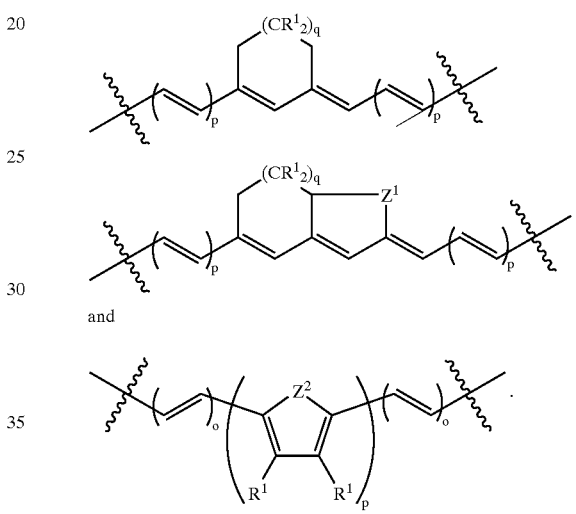

and

For instance, the present invention provides a chromophore that has the structure

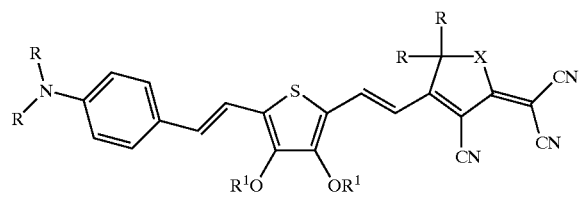

wherein, independently at each occurrence, R is alkyl, aryl or heteroalkyl; $R^1$ is alkyl, aryl or heteroalkyl; and X is O or S. For example, R may be —$(CH_2)_w$OH, —$(CH_2)_w$O$R^1$, —$(CH_2)_w$SH, —$(CH_2)_w$CO$_2$Et, —$(CH_2)_w$CO$_2$H, —$(CH_2)_w$NH$_2$, —$(CH_2)_w$CN, —$(CH_2)_w$halogen, or —COC$_6$H$_4$OCF=CF$_2$ where w is an integer selected from 1–12; and $R^1$ may be hydrogen, R, perfluoroalkyl, Si$R_3$, Si(CH$_3$)$_2$t-Bu, or Si(i-Pr)$_3$.

As another example, the present invention provides a chromophore that has the structure

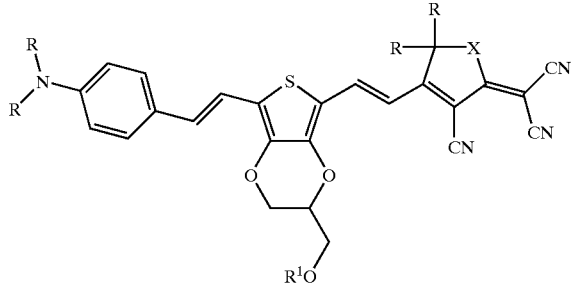

wherein, independently at each occurrence, R is alkyl, aryl or heteroalkyl; $R^1$ is alkyl, aryl or heteroalkyl; and X is O or S. For example, R may be —$(CH_2)_w$OH, —$(CH_2)_w$O$R^1$, —$(CH_2)_w$SH, —$(CH_2)_w$CO$_2$Et, —$(CH_2)_w$CO$_2$H, —$(CH_2)_w$NH$_2$, —$(CH_2)_w$CN, —$(CH_2)_w$halogen, or —COC$_6$H$_4$OCF=CF$_2$ where w is an integer selected from 1–12; and $R^1$ may be hydrogen, R, perfluoroalkyl, SiR$_3$, Si(CH$_3$)$_2$t-Bu, or Si(i-Pr)$_3$.

In yet another example, the present invention provides a chromophore having the structure

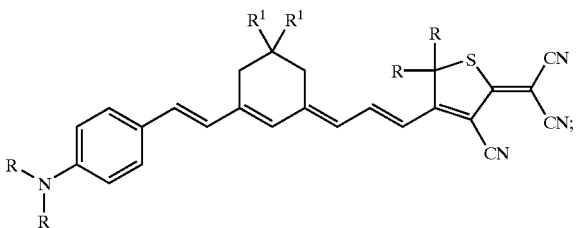

wherein R is alkyl, aryl, or heteroalkyl and $R^1$ is hydrogen, alkyl, aryl or heteroalkyl.

In still another example, the present invention provides a chromophore having the structure

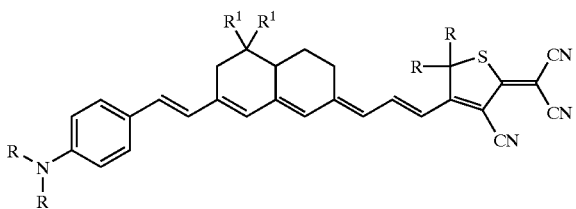

wherein R is alkyl, aryl, or heteroalkyl and $R^1$ is hydrogen, alkyl, aryl or heteroalkyl.

Chromophores according to the current invention that can be utilized in crosslinkable matrices are represented by the general formula CM:

   CM wherein E is a chromophore according to the current invention chosen from the group consisting of D1, D2, B1, B2, B3, B4, B5, B6, B7, A1, MAC, MDC, and MDAC; n=1–24; and at least one L includes a chemically reactive group that can be either incorporated into a crosslinkable polymer or utilized in a crosslinking process directly. The L group(s) is formally seen as being joined to the chromophore E through replacement of any hydrogen of E with a bond to L.

Preferably, the invention provides crosslinkable chromophoric matrices (CM1) wherein E is a chromophore according to the current invention chosen from the group consisting of D1, B1, B2, B3, B4, B5, B6, B7, A1, MAC, MDC, and MDAC; L includes a thermally crosslinkable —OCFCF$_2$ (TFVE) group; n=1–24; at least one of D, π, or A is attached to a polymer; and D, π, or A may be further substituted with L, halogen, alkyl, aryl, or heteroalkyl.

Matrices like CM1 may be prepared and crosslinked according the general process comprising the steps of: 1) polymerizing or copolymerizing the TFVE containing chromophore with or without a TFVE containing spacer/crosslinking agent to an extent that optical quality films may be obtained and that the chromophore may still be mobile in the polymer at temperatures below the crosslinking temperature of the TFVE group; 2) producing an optical quality film by methods known to those skilled in the art; 3) heating the film long enough to reduce residual solvents to selected levels; 4) heating the copolymer to a selected temperature to increase chromophore mobility; 5) applying a voltage across the polymer film sufficient to induce EO activity; and 6) heating the polymer to the thermoset temperature.

Materials like CM1 that contain TFVE groups may afford the following advantageous properties: 1) considerably high glass transition temperature when crosslinked; 2) high optical transparency due to the high concentration of C—F bonds, which minimizes optical loss caused by C—H overtones at 1.3 and 1.55 μm; and 3) enhancement of properties due to the synthetic versatility of the chromophores. Some embodiments according to the present invention include polymers having fluorination in the main chain and/or the groups pendant to the main chain of the polymer. Including fluorination in the main chain tends to improve both long-term temporal and thermal stability. The preparation, incorporation into molecules, and crosslinking chemistry of the TFVE group is known in the art, see U.S. Pat. Nos. 4,423,249, 5,021,602, J. Am. Chem. Soc. 2001, 121, 986, Organometallics 1996, 17, 783, Macromolecules 1996, 29, 852, and Chem. Mater. 2000, 12, 1187.

Figure 16A:
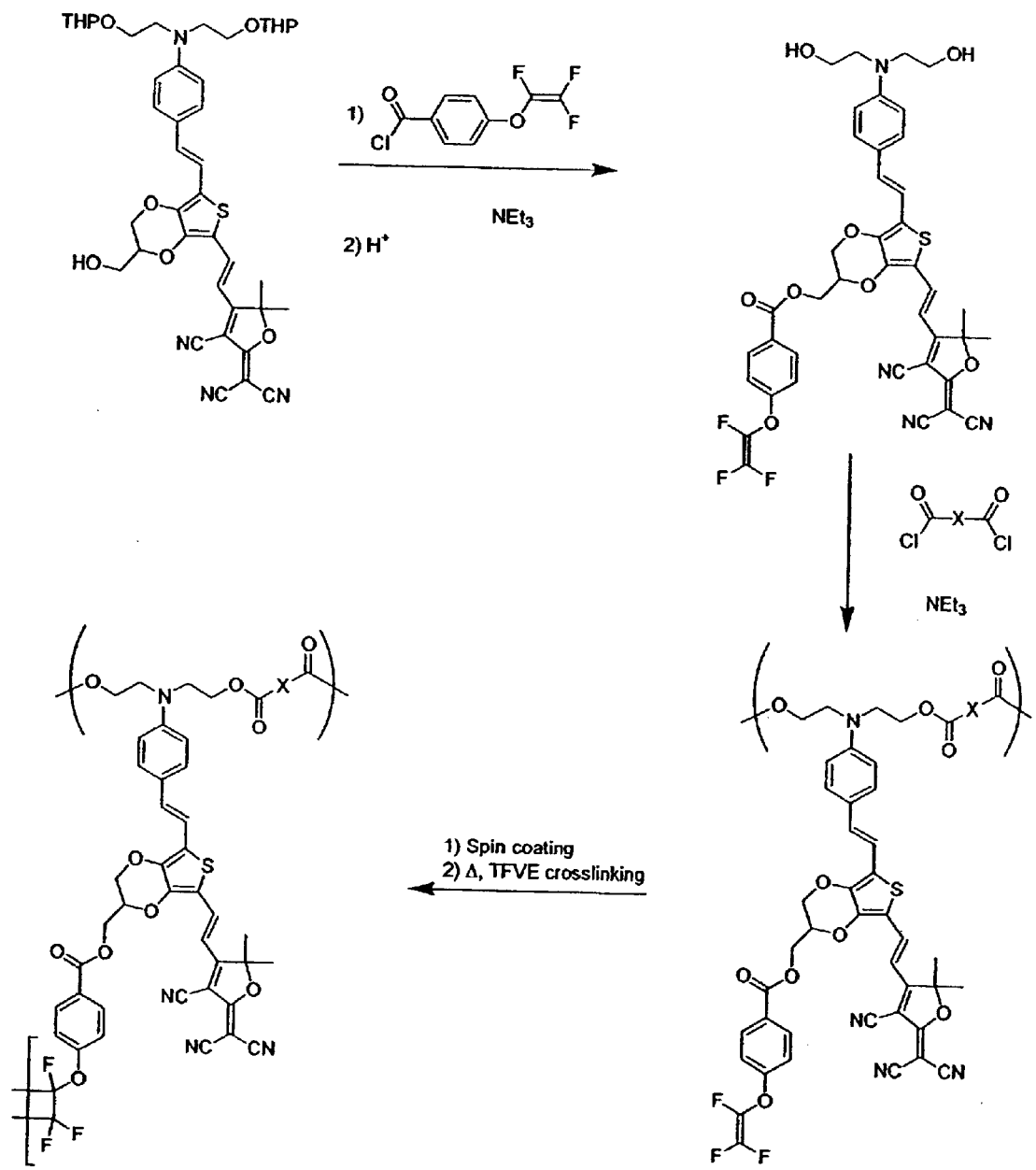
Figure 16B:
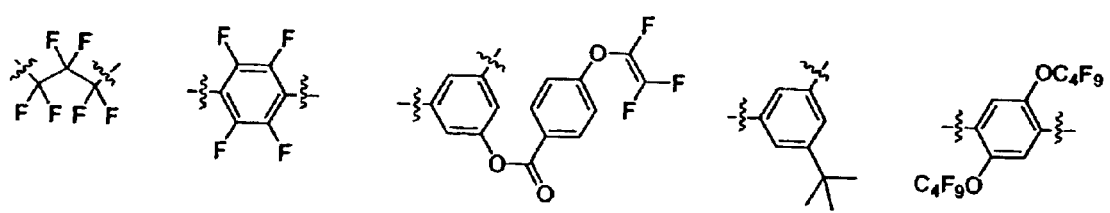

One embodiment of CM1 matrices may be prepared as shown in FIG. 16A, which is not meant to limit the scope of the invention: 1) a chromophore according to the formula B3 is esterified with a TFVE-containing acid chloride and then acid deprotected to give an diol; 2) the diol is polymerized with selected diacid chlorides to give a polymer with selected average molecular weight; and 3) crosslinking of the TFVE group by heating to the effective crosslinking temperature. Shown in FIG. 13B are exemplary diacid structures, which are not meant to limit the scope of the invention, that can be used in additional embodiments of the current invention. One skilled in the art would recognize that there are many possible variants of CM1 chromophoric matrices within the scope of the current invention that could be synthesized by methods like those disclosed in FIG. 16A.

Another embodiment of CM1 matrices may be prepared as shown in FIG. 14, which is not meant to limit the scope of the current invention: 1) a triol chromophore according to the formula B3 is triply esterified with a TFVE containing dendron acid chloride; 2) an optional prepolymerization step for the smaller generation dendrimers to a selected viscosity where the chromophore is effectively mobile at selected temperatures; 3) spin coating of the dendrimer or prepolymerized dendrimer; and 4) heating to the effective crosslinking temperature. One skilled in the art would recognize that there are many possible variants of CM1 chromophoric matrices within the scope of the current invention that could be synthesized by methods like those disclosed in FIG. 17.

Thus in various embodiments, the current invention provides:

Chromophoric matrices that are represented by the general formula CM

wherein E is a chromophore according to the current invention chosen from the group consisting of D1, B1, B2, B3, B4, B5, B6, B7, A1, MAC, MDC, and MDAC; n=1–24; and at least one L includes a chemically reactive group that can be either incorporated into a crosslinkable polymer or utilized in a crosslinking process directly;

Chromophoric matrices like CM (CM1) wherein E is a chromophore according to the current invention chosen from the group consisting of D1, B1, B2, B3, B4, B5, B6, B7, A1, MAC, MDC, and MDAC; L includes a thermally crosslinkable TFVE group; n=1–24; at least one of D, $\pi$, or A is attached to a polymer; and D, $\pi$, or A is further substituted with L, halogen, alkyl, aryl, or heteroalkyl;

A composition of matter comprising a chromophore covalently or non-covalently incorporated into a polymer matrix, wherein the chromophore is chosen from the group consisting of D1, D2, B1, B2, B3, B4, B5, B6, B7, A1, MAC, MDC, MDAC, CM and CM1;

A process, comprising the steps of: 1) covalently or non-covalently incorporating the chromophore into a polymer matrix, wherein the chromophore is chosen from the group consisting of D1, D2, B1, B2, B3, B4, B5, B6, B7, A1, MAC, MDC, and MDAC; 2) maintaining the polymer matrix at a selected temperature to allow effective chromophore mobility; and 3) applying an electric field sufficient to induce polar alignment of the chromophore in the polymer matrix; and A process, comprising the steps of: 1) providing a chromophore matrix according to the general formula CM or CM1; 2) maintaining the chromophore matrix at a selected temperature to allow effective chromophore mobility; 3) optionally applying an electric field sufficient to induce polar alignment of the chromophore in the polymer matrix; and 4) crosslinking reactive groups included in the chromophore matrix.

The materials and methods according to the present invention can be useful in a variety of electro-optic (EO) applications. In addition, these materials and methods may be applied to polymer transistors or other active or passive electronic devices, as well as OLED (organic light emitting diode) or LCD (liquid crystal display) applications.

The use of organic polymers in integrated optics and optical communication systems containing optical fibers and routers has been previously described. The compounds, molecular components, polymers, compositions etc. according to the present invention (hereinafter, "materials") may be used in place of currently used materials such as lithium niobate in most type of integrated optics devices, optical computing applications, and optical communication systems. For instance, the materials of the invention may be fabricated into switches, modulators, waveguides, or other electro-optical devices.

For example, in optical communication systems devices fabricated from the materials of the invention may be incorporated into routers for optical communication systems or waveguides for optical communication systems or for optical switching or computing applications. Because the materials are generally less demanding than currently used materials, devices made from such polymers may be more highly integrated, as described in U.S. Pat. No. 6,049,641, which is incorporated herein by reference. Additionally, such materials may be used in periodically poled applications as well as certain displays, as described in U.S. Pat. No. 5,911,018, which is incorporated herein by reference.

Techniques to prepare components of optical communication systems from optically transmissive materials have been previously described, and may be utilized to prepare such components from materials according to the present invention. Many articles and patents describe suitable techniques, and reference other articles and patents that describe suitable techniques, where the following articles and patents are exemplary:

Eldada, L. and Shacklette, L. "Advances in Polymer Integrated Optics" *IEEE Journal of Selected Topics in Quantum Electronics*, Vol. 6, No. 1, January/February 2000, pp. 54–68; Wooten, E. L. et al. "A Review of Lithium Niobate Modulators for Fiber-Optic Communication Systems" *IEEE Journal of Selected Topics in Quantum Electronics*, Vol. 6, No. 1, January/February 2000, pp. 69–82; Heismann, F. et al. "Lithium niobate integrated optics: Selected contemporary devices and system applications" *Optical Fiber Telecommunications* III B, Kaminow and Koch, Eds. New York: Academic, 1997, pp. 377–462; Murphy, E. "Photonic switching" *Optical Fiber Telecommunications* III B, Kaminow and Koch, Eds. New York: Academic, 1997, pp. 463–501; Murphy, E. *Integrated Optical Circuits and Components. Design and Applications*. New York: Marcel Dekker, Aug. 1999; Dalton, L. et al. "Polymeric Electro-optic Modulators: From Chromophore Design to Integration with Semiconductor Very Large Scale Integration Electronics and Silica Fiber Optics" *Ind. Eng. Chem. Res.* 1999, 38, 8–33; Dalton, L., et al. "From molecules to opto-chips: organic electro-optic materials" *J. Mater. Chem.*, 1999, 9, 1905–1920; Liakatas, I. et al. "Importance of intermolecular interactions in the nonlinear optical properties of poled polymers" *Applied Physics Letters* Vol. 76, No. 11 13 Mar. 2000 pp. 1368–1370; Cai, C. et al. "Donor-Acceptor-Substituted Phenylethenyl Bithiophenes: Highly Efficient and Stable Nonlinear Optical Chromophores" *Organic Letters* 1999, Vol. 1, No. 11 pp. 1847–1849; Razna J. et al. "NLO properties of polymeric Langmuir-Blodgett films of sulfonamide-substituted azobenzenes" *J. of Materials Chemistry*, 1999, 9, 1693–1698; Van den Broeck, K. et al. "Synthesis and nonlinear optical properties of high glass transition polyimides" *Macromol. Chem. Phys.* Vol. 200, pp. 2629–2635, 1999; Jiang, H. and Kakkar, A. K. "Functionalized Siloxane-Linked Polymers for Second-Order Nonlinear Optics" *Macromolecules* 1998, Vol. 31, pp. 2501–2508; Jen. A. K-Y. "High-Performance Polyquinolines with Pendent High-Temperature Chromophores for Second-Order Nonlinear Optics" *Chem. Mater*. 1998, Vol. 10, pp. 471–473; "Nonlinear Optics of Organic Molecules and Polymers" Edited by Hari Singh Nalwa and Seizo Miyata, CRC Press, 1997; Cheng Zhang, Ph.D. Dissertation, University of Southern California, 1999; Galina Todorova, Ph.D. Dissertation, University of Southern California, 2000; U.S. Pat. Nos. 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,408,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514, 799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091; 5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,966,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,322; and 6,091,879.

Thus, the foregoing references provide instruction and guidance to fabricate waveguides from materials according to the present invention using, e.g., direct photolithography, reactive ion etching, excimer laser ablation, molding, conventional mask photolithography, ablative laser writing, or embossing (e.g., soft embossing). The foregoing references also disclose electron acceptors, electron donors and electron bridges that may be incorporated into chromophores according to the present invention that also incorporate an electron acceptor and/or electron donor and/or electron bridge according to the present invention.

Components of optical communication systems that may be fabricated, in whole or part, with materials according to the present invention include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings. FIG. 18 illustrates one such component, which is a Mach Zehnder modulator (1) having an input (5), an output (20), two legs (10a, 10b) that are both coupled to the input and output, and an electrode (15) positioned near one of the legs. While the exemplified modulator or switch is based on a Mach-Zender type of structure, other modulator or switch structures, such as Y-branch structures, evanescent coupling structures, or controlled loss structures, may be within the scope of the invention.

The materials according to the present invention may be used with, for example, wafer-level processing, as applied in, for example, vertical cavity surface emitting laser (VCSEL) and CMOS technologies.

In many applications, the materials according to the present invention may be used in lieu of lithium niobate, gallium arsenide and other inorganic materials that currently find use as light-transmissive materials in optical communication systems.

The materials according to the present invention may be used in telecommunication, data communication, signal processing, information processing, and radar system devices and thus may be used in communication methods relying, at least in part, on the optical transmission of information. Thus, a method according to the invention includes transmitting information by light, where the light is transmitted at least in part through a material described herein.

In various embodiments, structures and devices according to the present invention can include:

An EO device comprising at least one of a chromophore, a composition, or a composition prepared by a process according to the present invention;

A waveguide comprising at least one of a chromophore, a composition, or a composition prepared by a process, according to the present invention;

An optical switch comprising at least one of a chromophore, a composition, or a composition prepared by a process, according to the present invention;

An optical modulator comprising at least one of a chromophore, a composition, or a composition prepared by a process, according to the present invention;

An optical coupler comprising at least one of a chromophore, a composition, or a composition prepared by a process, according to the present invention;

An optical router comprising at least one of a chromophore, a composition, or a composition prepared by a process, according to the present invention;

A communications system comprising at least one of a chromophore, a composition, or a composition prepared by a process, according to the present invention;

A method of data transmission comprising transmitting light through at least one of a chromophore, a composition, or a composition prepared by a process, according to the present invention;

A method of telecommunication comprising transmitting light through at least one of a chromophore, a composition, or a composition prepared by a process, according to the present invention;

A method of transmitting light comprising directing light through or via at least one of a chromophore, a composition, or a composition prepared by a process, according to the present invention;

A method of routing light through an optical system comprising transmitting light through or via at least one of a chromophore, a composition, or a composition prepared by a process, according to the present invention;

An interferometric optical modulator or switch, comprising: 1) an input waveguide; 2) an output waveguide; 3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end, wherein at least one of the first and second legs includes a composition of matter according to the present invention chosen from the group consisting of D1, B1, B2, B3, B4, B5, B6, B7, A1, MAC, MDC, MDAC, CM and CM1;

An optical modulator or switch, comprising: 1) an input; 2) an output; 3) a first waveguide extending between the input and output; and 4) a second waveguide aligned to the first waveguide and positioned for evanescent coupling to the first waveguide; wherein at least one of the first and second legs includes a composition of matter according to the present invention chosen from the group consisting of D1, B1, B2, B3, B4, B5, B6, B7, A1, MAC, MDC, MDAC, CM and CM1. The modulator or switch may further including an electrode positioned to produce an electric field across the first or second waveguide;

An optical router according to the invention includes a plurality of switches, wherein each switch includes: 1) an input; 2) an output; 3) a first waveguide extending between the input and output; and 4) a second waveguide aligned to the first waveguide and positioned for evanescent coupling to the first waveguide; wherein at least one of the first and second legs includes a composition of matter according to the present invention chosen from the group consisting of D1, D2, B1, B2, B3, B4, B5, B6, B7, A1, MAC, MDC, MDAC, CM and CM1. The plurality of switches may optionally be arranged in an array of rows and columns.

Additionally, the materials described herein may be applied to the devices or methods that control the phase of light waves passing through the material. In some applications, electrical fields are applied across a set of waveguides through which the light waves travel. Controlling the electrical fields allows the relative phases of the light waves to be controlled. Such approaches may be particularly useful in applications such as phased-array beam steering or phase matching of light waves passing through alternative waveguides.

The following examples are illustrative according to the present invention and are not intended as a limitation thereof.

EXAMPLES

EXAMPLE 1

Step A. As illustrated in Scheme 19, 3,4-dibutoxythiophene (12 g, 0.053 mol) (*Syn. Comm.* 1996, 26, 2205), DMF (8.14 mL, 0.105 mol) and 1,2-dichloroethane were placed in a flask and cooled to 0° C. $POCl_3$ (7.83 mL, 0.084 mol) was added dropwise. The reaction mixture was refluxed for 2 h, and then poured into sodium acetate solution (1 N). After work-up, the oil was purified by column chromatography with ethyl acetate/hexane. The aldehyde product, 12.17 g, was obtained with 90% yield.

Step B. [(4-N,N-Diethylaminophenyl)methyl] triphenylphosphonium bromide (17 g, 0.034 mol) and THF (300 mL) were placed in a flask and cooled to –40° C. BuLi solution in hexane (2.5 M, 13.5 mL, 0.034 mol) was added dropwise and the mixture was stirred at rt for 30 min. Then, a solution of the aldehyde prepared in Step A above (6.15 g, 0.024 mol) in 40 mL THF was added and stirred at RT for 4 h. After work-up, it was purified by column chromatography with ethyl acetate/hexane. The D-B3 product, 9.5 g, was obtained.

Step C. The D-B3 product (9.5 g, 0.024 mol), DMF (3.0 mL, 0.038 mol) and 1,2-dichloroethane were placed in a flask and cooled to 0° C. $POCl_3$ (5.1 g, 0.033 mol) was added dropwise and the mixture was refluxed for 2 h. It was then poured into sodium acetate solution. After work-up, the solid was purified by column chromatography with ethyl acetate/hexane. The D-B3 aldehyde product, 4.0 g, was obtained. The combined yield for the two steps is 39%.

Step D. D-B3 aldehyde as prepared in Step C (2 g, 4.66 mmol), the (dicyanovinylidene)cyanofuran acceptor (1.2 g, 6.05 mmol), piperidine (1 drop) and chloroform (10 mL) were placed in a flask and refluxed for 5 h. The solvent was removed under reduced pressure and the solid was purified by recrystallization with methylene chloride/hexane and column chromatography with ethyl acetate/methylene chloride/hexane. The D-B3-A chromophore, 1.5 g, was obtained in 53% yield.

EXAMPLE 2

Figure 20:
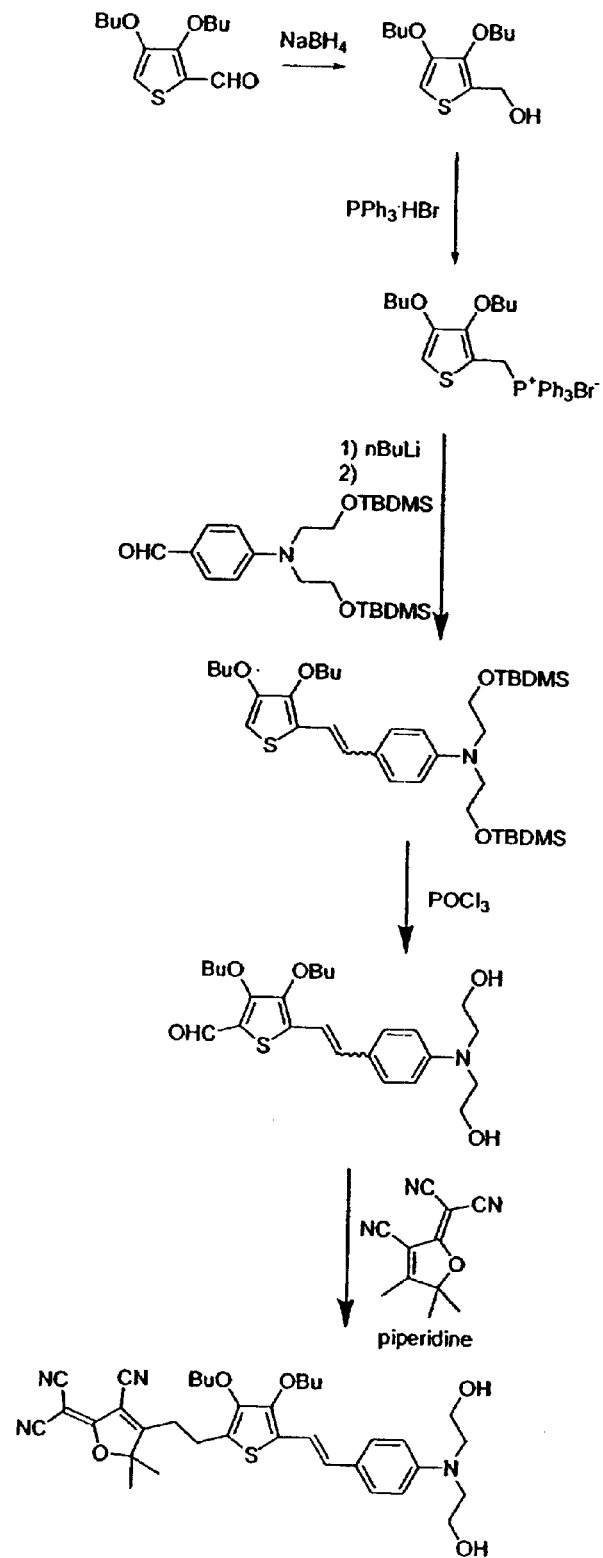

Step A. As illustrated in FIG. 20, 3,4-dibromo-2-thiophene carboxaldehyde (35 g, 0.137 mol) and methanol (120 mL) were placed in a flask. A solution was made by dissolving $NaBH_4$ (1.93 g, 0.051 mol) in 2 M NaOH solution (2.7 mL) and diluted with 25 mL water. At 0° C., the above solution was added dropwise into the flask and it was stirred at RT for 2 h. After work-up, the alcohol product, 34.5 g, was obtained with 98% yield.

Step B. The alcohol product from Step B (34.5 g, 0.134 mol), $PPh_3 \cdot HBr$ (41.3 g, 0.12 mol) and chloroform (140 mL) were placed in a flask equipped with Dean-Stark apparatus. The mixture was refluxed for 2 h and then the solvent was removed under reduced pressure. The solid was redissolved in chloroform and precipitated by ethyl ether. The phosphonium salt product, 48.6 g, was obtained with 69% yield.

Step C. The phosphonium product from Step B (30 g, 0.051 mol) and THF (600 mL) were placed in a flask and cooled to –40° C. BuLi solution in hexane (2.5 M, 22.6 mL, 0.057 mol) was added dropwise and the mixture was stirred at room temperature for 30 min. Then a solution of 4-N,N-Di[(2-tert-butyldimethylsilyloxy)ethyl]-aminobenzaldehyde (17.3 g, 0.040 mol) in 100 mL THF was added and stirred at RT for 4 h. After work-up, it was purified by column chromatography with ethyl acetate/hexane. The D-B3 product, 20 g, was obtained in 76% yield.

Step D. The D-B3 product above (19.5 g, 0.029 mol), DMF (4.1 mL, 0.053 mol) and 1,2-dichloroethane were placed in a flask and cooled to 0° C. $POCl_3$ (7.2 g, 0.047 mol) was added dropwise and the mixture was refluxed for 2 h. After the product mixture cooled to room temperature, an HCl solution was added and it was stirred for 2 h. It was then poured into sodium acetate solution. After work-up, the D-B3 aldehyde product, 13.5 g, was obtained.

Step E. The D-B3 aldehyde from Step D (9 g, 19.5 mmol), (dicyanovinylidene)cyanofuran (7.77 g, 39 mmol), piperidine (1 drop) and chloroform (30 mL) were placed in a flask and refluxed for 5 h. The solvent was removed under reduced pressure and the solid was purified by recrystallization with methylene chloride/hexane and column chromatography with ethyl acetate/methylene chloride/hexane. The D-B3-A chromophore, 6.0 g, was obtained in 48% yield.

EXAMPLE 3

Figure 21:
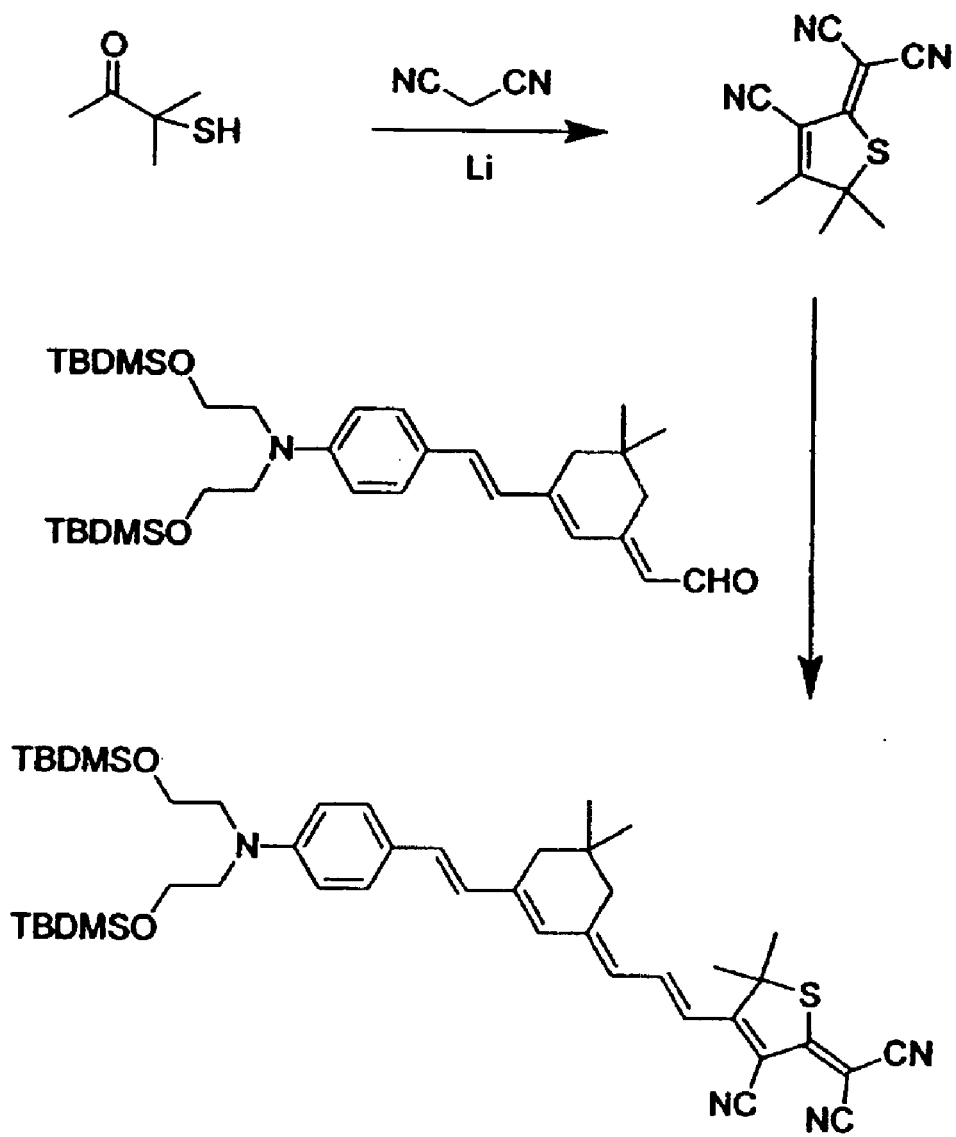
Figure 22:
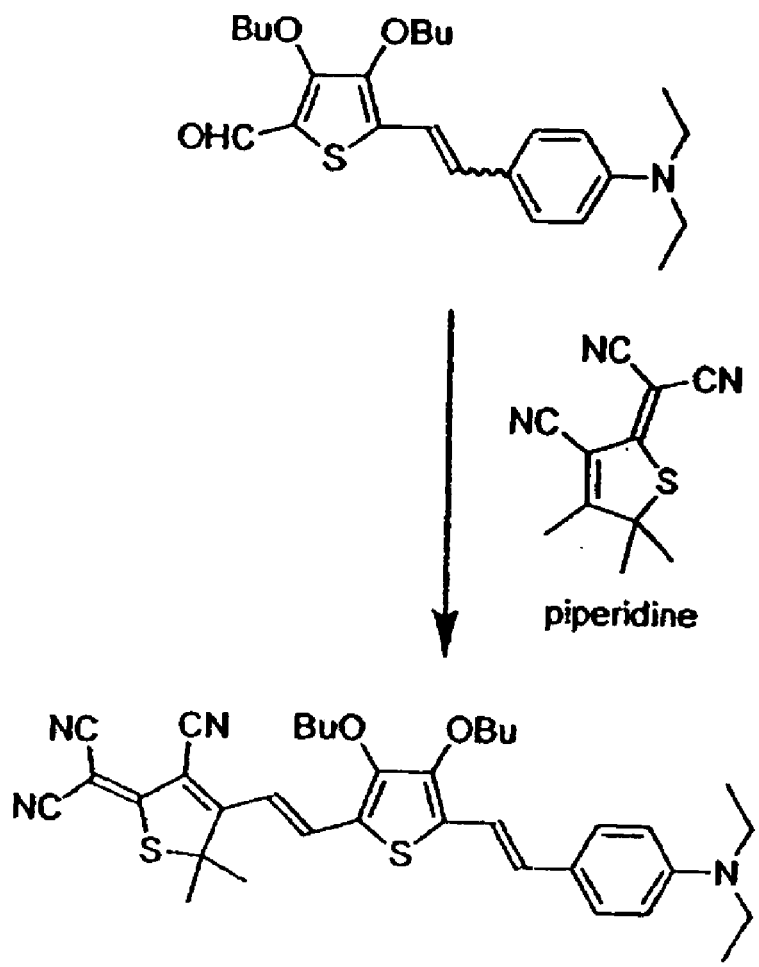
Figure 23:
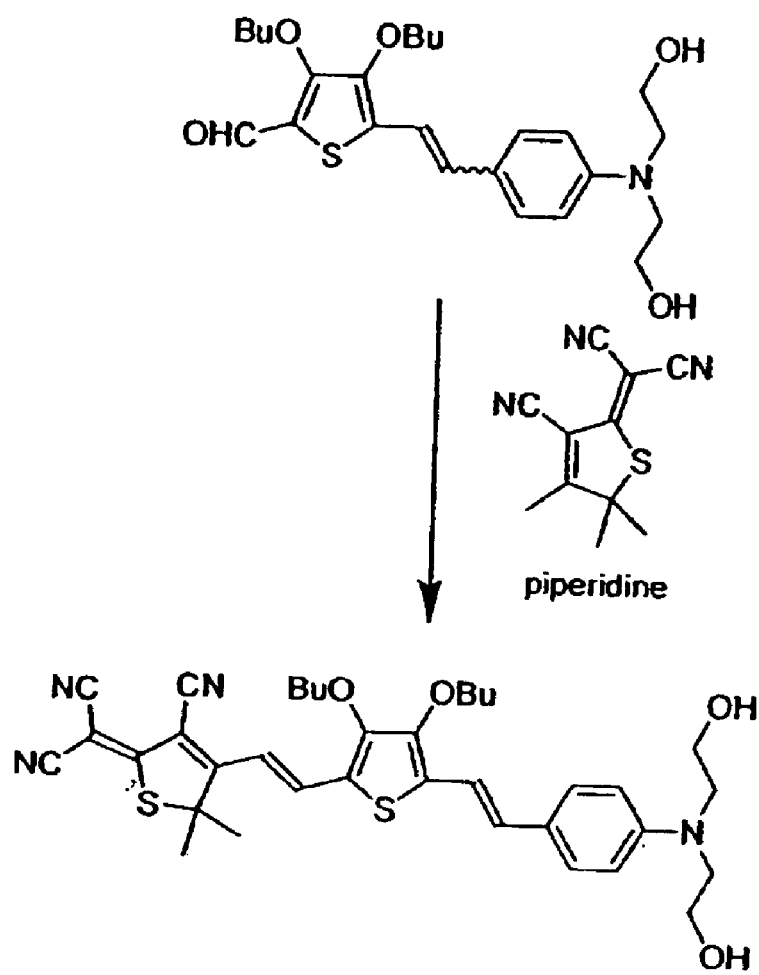

Step A. As illustrated in FIG. 21, 3-mercapto-3-methyl-2-butanone (5 g, 0.042 mol) (*Inorg. Chem.* 1998, 37, 5722), malononitrile (5.9 g, 0.089 mol) and ethanol (120 mL) were placed in a flask equipped with Soxlet that is charged with molecular sieves. A catalytic amount of Li was added and the mixture is refluxed for 8 h. It was then cooled to room temperature and solid precipitated out. The solid was collected by filtration. The filtrate was condensed and put into the freezer to collect more solid. Combined, 5.3 of the A1 acceptor was obtained with 58% yield.

Step B. The D-π aldehyde (2 g, 3.42 mmol), A1 acceptor (0.8 g, 3.72 mmol) and 15 mg of sodium ethoxide were dissolved in 40 ml of anhydrous ethanol. The mixture was stirred under reflux for 4 h. The precipitate was filtered off and washed with ethanol to give 1 g (35.7%) of the D-π-A1 chromophore.

EXAMPLE 4

As illustrated in FIG. 18, D-B3 aldehyde (1.8 g, 4.19 mmol), A1 acceptor (1.17 g, 5.45 mmol), piperidine (1 drop) and chloroform (10 mL) were placed in a flask and refluxed for 5 h. The solvent was removed under reduced pressure and the solid was purified by recrystallization with methylene chloride/hexane and column chromatography with ethyl acetate/methylene chloride/hexane. The D-B3-A1 chromophore, 1.8 g, was obtained in 69% yield.

EXAMPLE 5

Figure 19:
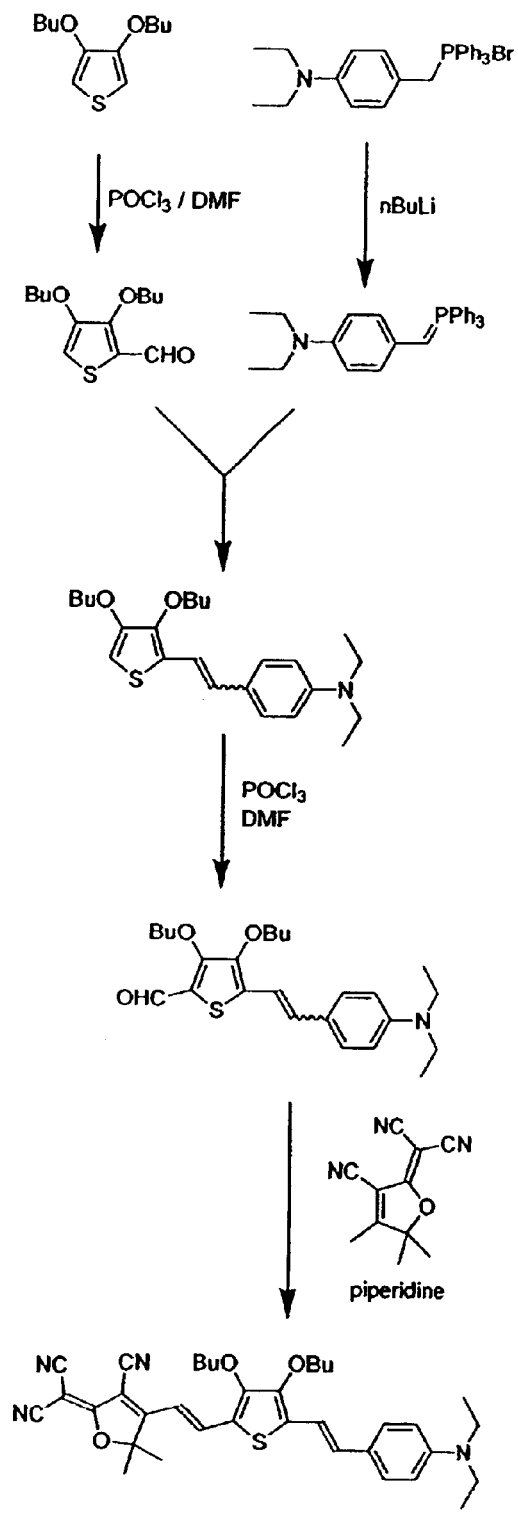

As illustrated in FIG. 19, D-B3 aldehyde (4.5 g, 9.75 mmol), A1 acceptor (4.2 g, 19.5 mmol), piperidine (1 drop) and chloroform (15 mL) were placed in a flask and refluxed for 5 h. The solvent was removed under reduced pressure and the solid was purified by recrystallization with methylene chloride/hexane and column chromatography with ethyl acetate/methylene chloride/hexane. The D-B3-A1 chromophore, 3.0 g, was obtained in 47% yield.

EXAMPLE 6

TABLE I: Photochemical stability data for "CLD chromophore" (Entry 1), currently invented D-π-A1 (Entry 2), and currently invented D-B3-A (Entry 3) chromophores. The studies were done in polycarbonate (PC) and poly (methyl)methacrylate (PMMA) matrices. The stability numbers are reported as the decrease in percent of the absorption maximum per minute when irradiated with a 400 watt halogen lamp (i.e., smaller numbers indicate greater photochemical stability).

TABLE I

| Entry | Structure | Polymer | Loading % by weight | Photochemical Stability % decrease in absorption/min (atmospheric) | % decrease in absorption/min (nitrogen) |
|---|---|---|---|---|---|
| 1 | 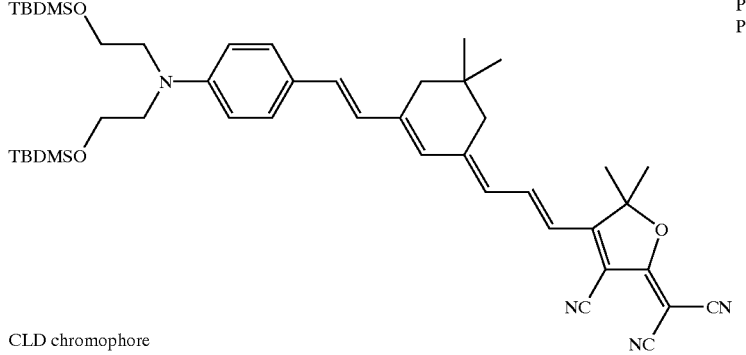 CLD chromophore | PC<br>PMMA | 30<br>30 | 4.6<br>4.1 | 0.074<br>0.059 |
| 2 | 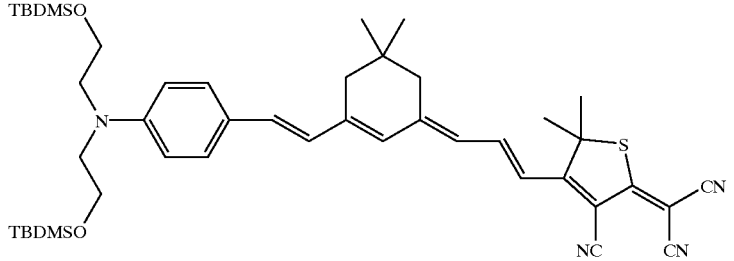 | PC<br>PMMA | 30<br>30 | 2.5<br>1.9 | 0.048<br>0.049 |

TABLE I-continued

| Entry | Structure | Polymer | Loading % by weight | Photochemical Stability % decrease in absorption/min (atmospheric) | % decrease in absorption/min (nitrogen) |
|---|---|---|---|---|---|
| 3 | 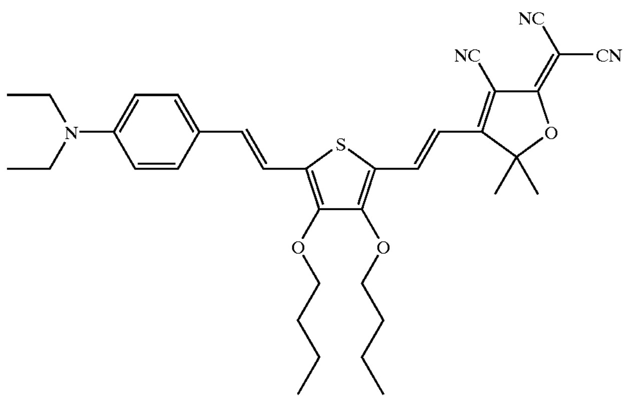 | PC | 20 | 0.6 | 0.0027 |
| | | PMMA | 20 | 0.70 | 0.0039 |

EXAMPLE 7

Figure 24:
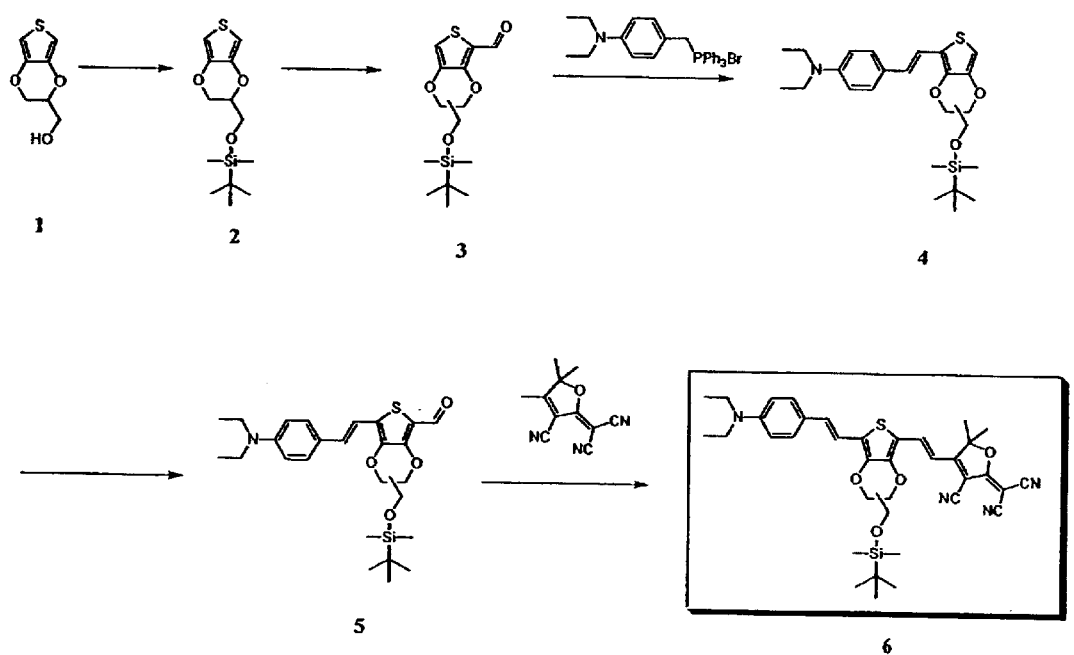

The following steps are illustrated in FIG. 24.

Step A. 2,3-dihydrothieno[3,4-b][1,4]dioxin-2-yl methanol (1) was prepared according to published literature (Stephan, O., et. al. *J. Electroanalytical Chem.* 443, 1998, 217).

Step B. Preparation of tert-Butyl-(2,3-dihydro-thieno[3,4-b][1,4]dioxin-2-ylmethoxy)-dimethyl-silane (2). 20 g (0.116 mole) of 1, 10.212 g (0.15 mole) of imidizole and 33.16 g (0.22 mole) of t-butyldimethylsilylchloride was dissolved in 100 ml of dry dimethylformamide. The reaction mixture was stirred at room temperature for 12 h at which point the precipitate is filtered from the mixture and discarded. The remaining solution is combined with 1 L of chloroform, and is added to 1 L of water. The organic layer is separated, and washed with water two more times. The organic layered is then dried with $MgSO_4$, filtered and the solvent is removed under reduced pressure. The product can be fractionally distilled to give 23 g of 2 (69% yield).

Step C. Preparation of 3-(tert-butyl-dimethyl-silanyloxymethyl)-2,3-dihydro-thieno[3,4-b][1,4]dioxine-5-carbaldehyde (3). 250 ml of dry tetrahydrofuran is added via syringe to 32 g (0.111 mole) of 2 contained in a nitrogen purged round bottom flask. The solution is cooled to –40° C., using a dry ice/acetone bath. The solution is stirred at –40° C. for 30 minutes, at which point 60 ml of 2.5 M BuLi in hexanes is added dropwise. The solution is allowed to stir for 30 min at 40° C., followed by the addition of 14.62 g (0.2 mole) dimethylformamide. The solution is warmed to room temperature, where it was stirred for 1 h. The solution is poured into an equal amount of chloroform, and extracted with water (3×). The organic phase is dried over $MgSO_4$, filtered, and solvent is removed under reduced pressure to yield a viscous red oil. The compound is purified on a silica column with a hexane/ethyl acetate mobile phase to yield 17 g (49% yield).

Step D. Preparation of (4-{2-[2-(tert-Butyl-dimethyl-silanyloxy-methyl)-2,3-dihydro-thieno[3,4-b][1,4]dioxin-5-yl]-vinyl}-phenyl)-diethyl-amine (4). To 10.47 g (0.021 mole) of diethyl-{4-[(triphenylphosphinebromide)-methyl]-phenyl}-amine was added 25 ml of dry tetrahydrofuran. The suspension was cooled to –40° C., and stirred for 30 min. 8.4 mL of 2.5 M BuLi was added dropwise to the suspension, which turned to a deep red solution over the course of 15 min. A 25 mL tetrahydrofuran solution of 3 (6.6 g, 0.021 mole) was added via an addition funnel over the course of 1 h at room temp. The solution was stirred for an additional two hours. The solution was poured into an equal amount of chloroform, and extracted with water (3×). The organic phase was dried over $MgSO_4$, filtered, and solvent was removed under reduced pressure to yield a viscous oil. The compound was purified on a silica column with a hexane/ethyl acetate mobile phase to yield 3.4 g of 4 (35% yield).

Step E. Preparation of 3-(tert-butyl-dimethyl-silanyloxymethyl)-7-[2-(4-diethylamino-phenyl)-vinyl]-2,3-dihydro-thieno[3,4-b][1,4]dioxine-5-carbaldehyde (5). 60 mL of dry tetrahydrofuran is added via syringe to 3.4 g (0.0074 mole) of 4 contained in a nitrogen purged round bottom flask. The solution is cooled to 0° C. The solution is stirred at 0° C. for 60 minutes, at which point 3.2 mL of 2.5 M BuLi in hexanes is added dropwise. The solution is allowed to stir for 15 min at 0° C., followed by the addition of 0.697 mL (0.009 mole) of anydrous dimethylformamide. The solution is warmed to room temperature, where it was stirred overnight. The tetrahydrofuran is removed under reduced pressure, and the resulting material is taken up in 500 mL of chloroform. The organic layer is washed with water three times, dried over $MgSO_4$, and solvent is then removed under reduced pressure. The compound is purified on a silica column with a hexane/ethyl acetate mobile phase.

Step F. Preparation of 2-[4-(2-{3-(tert-Butyl-dimethyl-silanyl-oxymethyl)-7-[2-(4-diethylamino-phenyl)-vinyl]-2,3-dihydro-thieno[3,4-b][1,4]dioxin-5-yl}-vinyl)-3-cyano-5,5-dimethyl-5H-furan-2-ylidene]-malononitrile (6). 20 mL of anhydrous chloroform was added to 0.318 g (0.0016 mole) of 2-(3-cyano-4,5,5-trimethyl-5H-furan-2-ylidene)-malononitrile, and 0.640 g (0.00131 mole) of 5. Once in solution, 10 mg of triethylamine were added and the reaction mixture was stirred at room temperature for 12 h. The solvent was removed under reduced pressure. The compound was purified on a silica column with a hexane/ethyl acetate mobile phase.

EXAMPLE 8

Figure 25:
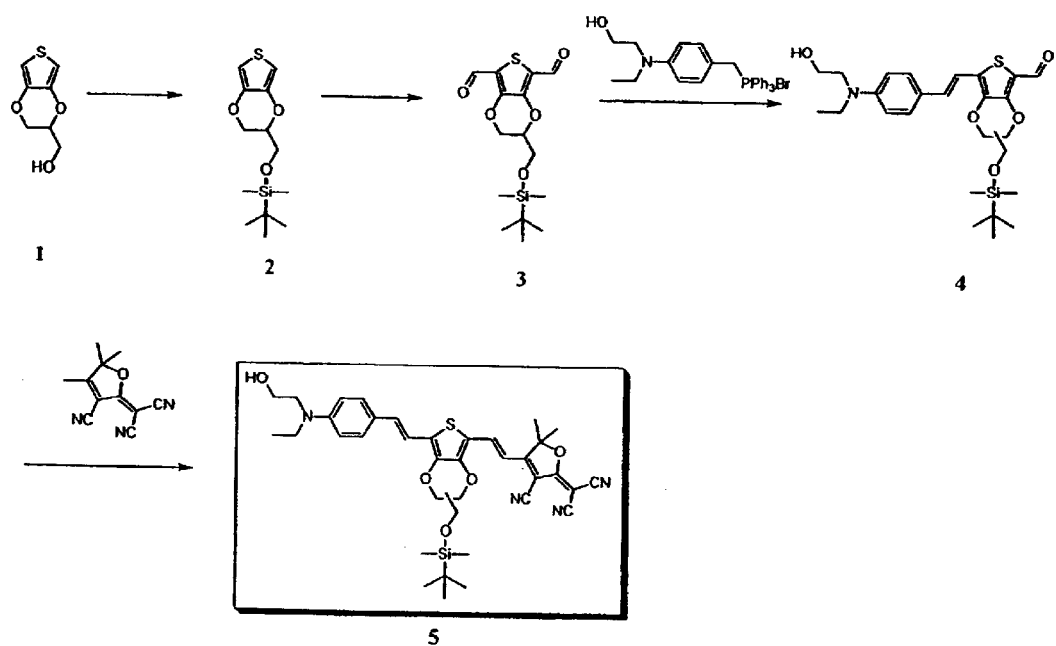

The following steps are illustrated in FIG. 25.

Step A. 2,3-dihydrothieno[3,4-b][1,4]dioxin-2-yl methanol (1, in FIG. 21) was prepared according to published literature (Stephan, O., et.al. J. Electroanalytical Chem 443, 1998, 217.)

Step B. Preparation of tert-butyl-(2,3-dihydro-thieno[3,4-b][1,4]-dioxin2-ylmethoxy)-dimethyl-silane (2). 20 g (0.116 mole) of 1 from Step A, 10.212 g (0.15 mole) of imidizole and 33.16 g (0.22 mole) of t-butyldimethylsilylchloride was dissolved in 100 mL of dry dimethylformamide. The reaction mixture was stirred at room temperature for 12 h at which point the precipitate was filtered from the mixture and discarded. The remaining solution was combined with 1 L of chloroform, and was added to 1 L of water. The organic layer was separated, and washed with water two more times. The organic layered was then dried with $MgSO_4$, filtered and the solvent was removed under reduced pressure. The product can be fractionally distilled to give 23 g of 2 (69% yield).

Step C. Preparation of 2-(tert-butyl-dimethyl-silanyloxymethyl)-2,3-dihydro-thieno[3,4-b][1,4]dioxine-5,7-dicarbaldehyde (3). 150 mL of dry tetrahydrofuran was added via syringe to 23 g (0.080 mol) of 2 contained in a nitrogen purged round bottom flask. The solution was cooled to 40° C. using a dry ice/acetone bath. The solution is stirred at −40° C. for 30 minutes, at which point 60 mL of 2.0 M BuLi in hexanes was added dropwise. The solution was allowed to stir for 30 min at −40° C., followed by the addition of 15.49 mL (0.2 mol) dimethylformamide. The solution was warmed to room temperature, where it was stirred for 1 h. The solution was poured into an equal amount of chloroform, and extracted with water (3×). The organic phase was dried over $MgSO_4$, filtered, and solvent was removed under reduced pressure to a yield viscous red oil. The compound was purified on a silica column with a hexane/ethyl acetate mobile phase to yield 10 g (36% yield).

Step D. Preparation of 3-(tert-butyl-dimethyl-silanyloxymethyl)-7-(2-{4-[ethyl-(2-hydroxy-ethyl)-amino]-phenyl}-vinyl)-2,3-dihydro-thieno[3,4-b][1,4]dioxine-5-carbaldehyde (4). To 9.97 g (0.019 mol) of 2-(ethyl-{4-[(triphenylphosphinebromide)-methyl]-phenyl}-amino)-ethanol was added 50 ml of dry tetrahydrofuran. The suspension was cooled to −40° C., and stirred for 30 min. 16 mL of 2.5 M BuLi was added dropwise to the suspension, which turned to a deep red solution over the course of 15 min. A 50 mL tetrahydrofuran solution of 3 (6.56 g, 0.019 mole) was added via an addition funnel over the course of 1 h at room temp. The solution was stirred for an additional two hours. The solution was poured into an equal amount of chloroform, and extracted with water (3×). The organic phase was dried over $MgSO_4$, filtered, and solvent was removed under reduced pressure to yield a viscous red oil. The compound was purified on a silica column with a hexane/ethyl acetate mobile phase to give 7.2 g (75% yield) of 4.

Step E. Preparation of 2-(4-{2-[3-(tert-butyl-dimethyl-silanyl-oxymethyl)7-(2-{4-[ethyl-(2-hydroxy-ethyl)-amino]-phenyl}-vinyl)-2,3-dihydro-thieno-[3,4-b][1,4]dioxin-5-yl]-vinyl}-3-cyano-5,5-dimethyl-5H-furan-2-ylidene)-malononitrile (5). 15 mL of anhydrous chloroform was added to 1.99 g (0.010 mol) of 2-(3-cyano-4,5,5-trimethyl-5H-furan-2-ylidene)-malononitrile, and 2.91 g of 4 (0.007 mol). Once in solution, 5 drops of piperidine were added and the reaction mixture was stirred at reflux. The reaction went to completion in 2 h. The crude reaction mixture was poured into water, and an equal amount of chloroform was added. The organic layered was washed three times with water, dried over $MgSO_4$, and filtered. The solvent was removed under reduced pressure. The compound was purified on a silica column with a hexane/ethyl acetate mobile phase to yield 1.5 g of 5 (37.5% yield).

From the foregoing it will be appreciated that, although specific embodiments of the invention have been described herein for purposes of illustration, various modifications may be made without deviating from the spirit and scope of the invention. Accordingly, the invention is not limited, except as by the appended claims.

What is claimed is:

1. A chromophore of the structure

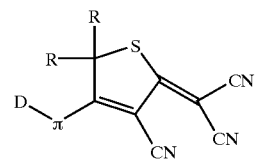

wherein, independently at each occurrence,

D is an electron donating group having low electron affinity relative to the electron affinity of

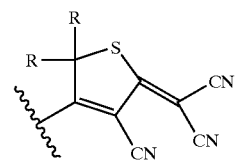

π is absent or a bridge that provides electronic conjugation between D and the double bond adjacent to π; and R is alkyl, aryl, heteroalkyl or heteroaryl.

2. The chromophore of claim 1 having the structure

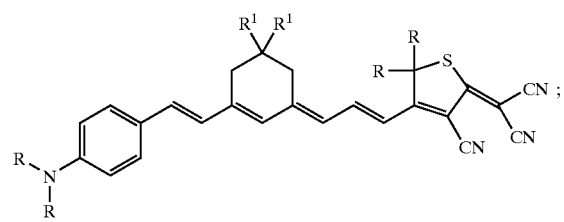

wherein R is alkyl, heteroalkyl or heteroaryl and $R^1$ is hydrogen, alkyl, aryl, heteroalkyl or heteroaryl.

3. The chromophore of claim 1 having the structure

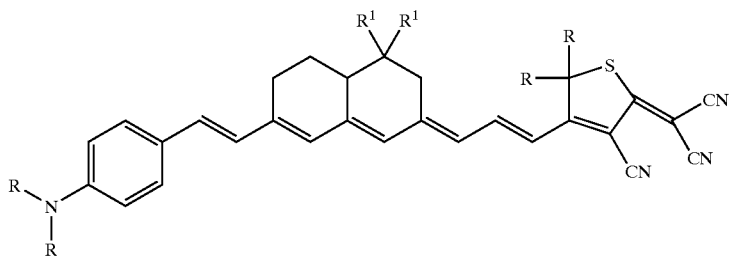

wherein R is alkyl, heteroalkyl or heteroaryl and $R^1$ is hydrogen, alkyl, aryl, heteroalkyl or heteroaryl.

4. A composition of matter comprising

E—L$_n$ wherein E is the chromophore of claim 1; L comprises a chemically reactive group that is crosslinkable; and n=1–24.

5. The composition of matter of claim 4, wherein L includes a thermally crosslinkable trifluorovinylether group; at least one of D, π, or A of the chromophore is covalently bound to a polymer; and D, π, or A is further substituted with L, halogen, alkyl, aryl, heteroalkyl or heteroaryl.

6. A composition of matter comprising the chromophore of claim 1 non-covalently incorporated into a crosslinkable polymer matrix.

* * * * *